US011034737B2

(12) United States Patent
Matschiner et al.

(10) Patent No.: US 11,034,737 B2
(45) **Date of Patent: *Jun. 15, 2021**

(54) PROTEINS SPECIFIC FOR CALCITONIN GENE-RELATED PEPTIDE

(71) Applicant: Pieris Pharmaceuticals GmbH, Freising (DE)

(72) Inventors: Gabriele Matschiner, Munich (DE); Christine Rothe, Dachau (DE); Alexander Wiedenmann, Ulm (DE); Rachida Siham Bel Aiba, Munich (DE); Marlon Hinner, Munich (DE); Andrea Allersdorfer, Wolnzach (DE); Bradley Lunde, Munich (DE); Kazufumi Kubota, Tokyo (JP); Mitsuhiro Makino, Tokyo (JP); Sakiko Takahashi, Tokyo (JP); Ryuji Hashimoto, Tokyo (JP); Tohru Takahashi, Tokyo (JP); Mamoru Otoyo, Tokyo (JP)

(73) Assignee: Pieris Pharmaceuticals GmbH, Hallbergmoos (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,761

(22) Filed: Jul. 8, 2019

(65) Prior Publication Data

US 2019/0338002 A1 Nov. 7, 2019

Related U.S. Application Data

(62) Division of application No. 15/371,698, filed on Dec. 7, 2016, now Pat. No. 10,400,016.

(60) Provisional application No. 62/265,792, filed on Dec. 10, 2015.

(51) Int. Cl.
*A61K 38/00* (2006.01)
*C07K 14/47* (2006.01)

(52) U.S. Cl.
CPC ............. *C07K 14/47* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS 5,728,553 A 3/1998 Goodey et al.
5,849,576 A 12/1998 Skerra et al.
6,099,517 A 8/2000 Daugherty
6,103,493 A 8/2000 Skerra et al.
6,123,936 A 9/2000 Platz et al.
6,177,074 B1 1/2001 Glue et al.
6,403,564 B1 6/2002 Ganguly et al.
6,500,930 B2 12/2002 Adamson
6,620,413 B1 9/2003 De Sauvage et al.
6,696,245 B2 2/2004 Winter et al.
7,250,297 B1 7/2007 Beste et al.
7,252,998 B2 8/2007 Skerra et al.
9,051,382 B2 6/2015 Trentmann et al.
9,260,492 B2 2/2016 Matschiner et al.
9,549,968 B2 1/2017 Skerra et al.
9,884,898 B2 2/2018 Corvey et al.
10,273,275 B2 4/2019 Hinner et al.
10,400,016 B2 9/2019 Matschiner et al.
2003/0069395 A1 4/2003 Sato et al.
2006/0058510 A1 3/2006 Skerra et al.
2006/0088908 A1 4/2006 Skerra et al.
2012/0294797 A1 11/2012 Kovacevich et al.
2013/0079286 A1 3/2013 Skerra et al.
2013/0085113 A1 4/2013 Hohlbaum et al.
2017/0114109 A1 4/2017 Skerra et al.
2017/0166615 A1 6/2017 Matschiner et al.
2017/0369542 A1 12/2017 Trentmann et al.
2018/0016312 A1 1/2018 Bel Aiba et al.
2018/0141988 A1 5/2018 Hinner et al.
2018/0148484 A1 5/2018 Hinner et al.

FOREIGN PATENT DOCUMENTS

DE 4417598 A1 12/1995
DE 19641876 A1 4/1998
DE 19742706 A1 4/1999

(Continued)

OTHER PUBLICATIONS

"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.
Altschul et al., Gapped Blast and PSI-Blast: a new generation of protein database search programs, Nucleic Acids Res., 25(17):3389-3402 (1997).
Altschul, S. et al., Basic Local Alignment Search Tool; J. Mol. Biol., 215:403-410 (1990).
Amstutz, P. et al., In vitro display technologies: novel developments and applications, Curr. Opin. Biotechnol., 2001, 12:400-405.

(Continued)

*Primary Examiner* — Jeanette M Lieb
(74) *Attorney, Agent, or Firm* — Choate, Hall & Stewart LLP; Brian E. Reese; Dana M. Daukss

(57) ABSTRACT

The present disclosure provides hNGAL muteins that bind CGRP and can be used in various application including pharmaceutical applications, for example, migraine. The present disclosure also concerns methods of making one or more muteins described herein as well as compositions and combinations comprising one or more of such muteins. The present disclosure further relates to nucleic acid molecules encoding such muteins and to methods for generation of such muteins and nucleic acid molecules. In addition, the application discloses therapeutic and/or diagnostic uses of these muteins as well as compositions and combinations comprising one or more of such muteins.

17 Claims, 20 Drawing Sheets

Specification includes a Sequence Listing.

(56) References Cited

FOREIGN PATENT DOCUMENTS

| | | | |
|---|---|---|---|
| DE | 19926068 | C1 | 1/2001 |
| EP | 0 330 451 | A2 | 8/1989 |
| EP | 0 361 991 | A2 | 4/1990 |
| JP | 2005503829 | A | 2/2005 |
| JP | 2007284351 | A | 11/2007 |
| WO | WO-96/23879 | A1 | 8/1996 |
| WO | WO-98/16873 | A1 | 4/1998 |
| WO | WO-99/16873 | A1 | 4/1999 |
| WO | WO-99/064016 | A1 | 12/1999 |
| WO | WO-00/075308 | A1 | 12/2000 |
| WO | WO-03/029462 | A1 | 4/2003 |
| WO | WO-03/029463 | A2 | 4/2003 |
| WO | WO-03/029471 | A1 | 4/2003 |
| WO | WO-2005/019254 | A1 | 3/2005 |
| WO | WO-2005/019255 | A1 | 3/2005 |
| WO | WO-2005/019256 | A2 | 3/2005 |
| WO | WO-2006/056464 | A2 | 6/2006 |
| WO | WO-2007/038619 | A2 | 4/2007 |
| WO | WO-2009/052390 | A1 | 4/2009 |
| WO | WO-2009/156456 | A1 | 12/2009 |

OTHER PUBLICATIONS

Bachmann, Barbara J., Linkage Map of *Escherichia coli* K-12. Edition 8, Microbial. Rev., Jun. 1990, 54(2):130-197.

Beck, et al., Nucleotide Sequence and Genome Organisation of Filamentous Bacteriophages f1 and fd, Gene, vol. 16, pp. 35-58, 1981.

Beste, G. et al., Small antibody-like proteins with prescribed ligand specificities derived from the lipocalin fold, Proc. Natl. Acad. Sci. USA, Mar. 1999, 96:1898-1903.

Bittker, J. et al., Nucleic acid evolution and minimization by nonhomologous random recombination, Nat. Biotechnol., Oct. 2002, 20:1024-1029.

Bos et al., OctoDEX.TM.—Controlled Release of Pharmaceutical Proteins from Hydrogels, Business Briefing: Pharmatech, 2003:1-6.

Breustedt, D. et al., Comparative ligand-binding analysis of ten human lipocalins, Biochim. Biophys. Acta, 2006, 1764:161-173.

Broders, O et al., Hyperphage. Improving antibody presentation in phage display, Methods Mol. Biol., 2003, 205:295-302.

Brody et al., Active and Passive Immunotherapy for Neurodegenerative Disorders, Annu. Rev. Neurosci., 2008, 31:175-193.

Bruckdorfer, T., et al., From Production of Peptides in Milligram Amounts for Research to Multi-Tons Quantities for Drugs of the Future, Curr. Pharm. Biotechnol., 2004, 5:29-43.

Bullock, W. et al., XL1-Blue: A High Efficiency Plasmid Transforming recA *Escherichia coli* Strain with Beta-Galactosidase Selection, Biotechniques, 1987, 5(4):376-378.

Bundgaard, J.R. et al., Molecular Cloning and Expression of A cDNA Encode NGAL: A Lipocalin Expressed in Human Neutrophils, Biochemical and Biophysical Research Communications, Aug. 15, 1994, pp. 1468-1475, vol. 202, No. 3, XP002036694.

Carnemolla et al., Phage Antibodies with PAN-Species Recognition of the Oncofoetal Angiogenesis Marker Fibronectin ED-B Domain, Int. J. Cancer, 1996, 68:397-405.

Chan et al., The primary structure of rat α 2μ globulin-related protein, Nucleic Acids Research, vol. 16, No. 23, pp. 11368, 1988.

Coles, et al., The Solution Structure and Dynamics of Human Neutrophil Gelatinase-associated Lipocalin, J. Mol. Biol., vol. 289, pp. 139-157, 1999.

Dennis, M. et al., Albumin Binding as a General Strategy for Improving the Pharmacokinetics of Proteins, J. Biol. Chem., Sep. 20, 2002, 277(38):35035-35043.

Dodel et al., Immunotherapy for Alzheimer's disease, Lancet Neurology, Apr. 2003, 2:215-220.

Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.

Fitzgerald, Kevin, In Vitro Display Technologies—New Tools for Drug Discovery, Reviews, vol. 5, No. 6, pp. 253-258, Jun. 2000.

Fling, S. and Gregerson, D., Peptide and Protein Molecular Weight Determination by Electrophoresis Using a High-Molarity Tris Buffer System without Urea, Anal. Biochem., 1986, 155:83-88.

Flower, Darren R., The lipocalin protein family: structure and function, Biochem. J., 1996, 318:1-14.

Frank, Ronald, The SPOT-synthesis technique Synthetic Peptide arrays on membrane supports—principles and applications, J. Immunol. Methods, 2002, 267:13-26.

Fuerteges, F. and Abuchowski, A., The Clinical Efficacy of Poly(Ethylene Glycol)-Modified Proteins,: J. Control. Release, 1990, 11:139-148.

Fujii, Phage display and beyond antibody—molecular target by antibody molecule, Seikagaku, 2010, vol. 82, No. 8, pp. 710-726, Abstract.

Gaillard, P. et al., Diphtheria toxin receptor-targeted brain drug delivery, International Congress Series., 2005, 1277:185-198.

Gaillard, P. et al., Targeted delivery across the blood-brain barrier, Expert Opin Drug Deliv., 2005, 2(2):299-309.

Gasteiger et al., ExPASy: the proteomics server for in-depth protein knowledge and analysis, Nucleic Acids Res., 2003, 31(13):3784-3788.

Goetz, D. et al., Ligand Preference Inferred from the Structure of Neutrophil Gelatinase Associated Lipocalin, Biochemistry, 2000, 39:1935-1941.

Gronwall et al., Selection and characterization of Affibody ligands binding to Alzheimer amyloid β peptides, J. Biotechnol., 2007, 128:162-183.

Haass et al., Soluble protein oligomers in neurodegeneration: lessons from the Alzheimer's amyloid β-peptide, Nat. Rev. Mol. Cell. Biol., Feb. 2007, 8:101-112.

Hengen, Paul N., Methods and Reagents, Trends Biochem. Sci., vol. 21, pp. 75-76, 1996.

Hoess, Ronald H., Phage Display of Peptides and Protein Domains, Structural Biology, vol. 3, pp. 572-279, 1993.

Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.

Hortschansky et al., The aggregation Kinetics of Alzheimer's β-amyloid peptide is controlled by stochastic nucleation, Protein Sci., 2005, 14:1753-1759.

Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.

Karlsson et al., Kinetic analysis of monoclonal antibody-antigen interactions with a new biosensor based analytical system, J. Immunol. Methods, 1991, 145:229-240.

Kaspar et al., Fibronectin as target for tumor therapy, Int. J. Cancer, 2006, 118:1331-1339.

Khurana et al., Mechanism of thioflavin T binding to amyloid fibrils, J. Struct. Biol., 2005, 151:229-238.

Kim, H. et al., High-Affinity Recognition of Lanthanide(III) Chelate Complexes by a Reprogrammed Human Lipocalin 2, J. Am. Chem. Soc., 2009, 131:3565-3576.

Kjelsden, L. et al., Human Neutrophil Gelatinase-Associated Lipocalin and Homologous Proteins in Rat and Mouse, Biochimica et Biophysica Acta, vol. 1482, pp. 272-283, 2000.

Konig, T. and Skerra, A., Use of an albumin-binding domain for the selective immobilization of recombinant capture antibody fragments on Elisa plates, J. Immunol. Methods, 1998, 218:73-83.

Korean Office Action issued in corresponding application No. 10-2012-7017730 dated Jul. 28, 2018 with English translation.

Kraulis, et al., The Serum Albumin-Binding Domain of *Streptococcal* Protein G is a Three-Helical Bundle: A Heteronuclear NMR Study, FEBS Letters, vol. 378, pp. 190-194, 1996.

Leahy et al., Crystallization of a Fragment of Human Fibronectin: Introduction of Methionine by Site-Directed Mutagenesis to Allow Phasing via Selenomethionine, Proteins, 1994, 19:48-54.

Lichtlen et al., Antibody-based approaches in Alzheimer's research: safety, pharmacokinetics, metabolism, and analytical tools, J. Neurochem., 2007, 104:859-874.

(56) References Cited

OTHER PUBLICATIONS

Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.
Murakami, H. et al., Random insertion and deletion of arbitrary number of bases for codon-based random mutation of DNAs, Nat. Biotechnol., Jan. 2002, 20:76-81.
Notice of Reasons for Rejections dated Jan. 20, 2015 issued in Japanese Application No. 2012-542505, with English translation.
Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.
Paine et al., The Lipocalin website, Elsevier Science B.V., Biochimica et Biophysica Acta 1482, pp. 351-352, 2000.
Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between α1-Acid Glycoprotein and Serum Retinol-Binding Protein and Its Relatives, 1987, The FASEB journal 1.3 (1987): 209-214.
Pini et al., Design and Use of a Phage Display Library, J. Biol. Chem., Aug. 21, 1998, 273(34):21769-21776.
Pini, A. et al., Phage Display and Colony Filter Screening for High-Throughput Selection of Antibody Libraries, Comb. Chem. High Throughput Screen., 2002, 5:503-510.
Pujuguet et al., Expression of Fibronectin ED-A+ and ED-B+ Isoforms by Human and Experimental Colorectal Cancer, Am. J. Pathol., Feb. 1996, 148(2):579-592.
Redl, Bernhard, Human tear lipocalin, Biochim. Biophys. Acta, 2000, 1482:241-248.
Roberts, Richard W., Totally In Vitro Protein Selection Using mRNA-Protein Fusions and Ribosome Display, Current Opinion in Chemical Biology, vol. 3, pp. 268-273, 1999.
Rodi, D. and Makowski, L., Phage-display technology—finding a needle in a vast molecular haystack, Curr. Opin. Biotechnol., 1999, 10:87-93.
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. et al., A Novel Type of Receptor Protein, Based on the Lipocalin Scaffold, with Specificity for Digoxigenin, J. Mol. Biol., 2000, 297:1105-1120.
Schliemann et al., Antibody-based targeting of the tumor vasculature, Biochim. Biophys. Acta, 2007, 1776:175-192.
Schmidt et al., The Strep-tag system for one-step purification and high-affinity detection of capturing of proteins, Nat. Protoc., 2007, 2(6):1528-1535.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Schonfeld, D. et al. An engineered lipocalin specific for CTLA-4 reveals a combining site with structural and conformational features similar to antibodies, PNAS, 106(20): 8198-8203 (2009).
Skerra et al., 'Anticalins': a new class of engineered ligand-binding proteins with antibody-like properties, Reviews in Molecular Biotechnology, 2001, 74:257-275.
Skerra, A., et al., Lipocalins as a scaffold, Elsevier Science B.V., Biochimica et Biophysica Acta 1482, pp. 337-350, 2000.
Skerra, Anticalins as alternative binding proteins for therapeutic use; Current Opinion in Molecular Therapeutics, 9(4): 336-344 (Aug. 2007).
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.
Uniprot—P80188 (NGAL_Human), Neutrophil gelatinase-associated lipocalin, retrieved from https://www.unitprot.org/uniprot/P80188, 15 pages (retrieved on Sep. 30, 2019).
Uniprot Database—Signal peptide, retrieved from https://www.uniprot.org/help/signal, 2 pages (retrieved on Aug. 27, 2019).
Vajo, Z. and Duckworth, W., Genetically Engineered Insulin Analogs: Diabetes in the New Millennium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Virnekas et al., Trinucleotide phosphoramidites: ideal reagents for the synthesis of mixed oligonucleotides for random mutagenesis, Nucleic Acids Res, 1994, 22(25):5600-5607.
Vogt, M. and Skerra, A., Construction of an Artificial Receptor Protein ("Anticalin") Based on the Human Apolipoprotein D, ChemBioChem, 5: 191-199 (2004).
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang et al., Expanding the Genetic Code of *Escherichia coli*, Science, Apr. 20, 2001, 292:498-500.
Wang et al., Expanding the genetic code, Chem. Comm., 2002, 1:1-11.
Wang, A. M. et al., Molecular Cloning of the Complementary DNA for Human Tumor Necrosis Factor, Science, vol. 228, pp. 149-154, 1985 (Abstract).
Wells, J. et al., Rapid Evolution of Peptide and Protein Binding Properties In Vitro, Current Opinion in Structural Biology, vol. 2, pp. 597-604, 1992.
Wilson, D. et al., The use of mRNA display to select high-affinity protein-binding peptides, Proc. Natl. Acad. Sci. USA, Mar. 27, 2001, 98(7):3750-3755.
Yanisch-Perron, C. et al., Improved M13 phage cloning vectors and host strains: nucleotide sequences of the M13mp18 and pUC19 vectors, Gene, 1985, 33:103-119.
Zaccolo, M.et al., An Approach to Random Mutagenesis of DNA Using Mixtures of Triphosphate Derivatives of Nucleoside Analogues, J. Mal. Biol., 1996, 255:589-603.
Zardi, L. et al., Transformed human cells produce a new fibronectin isoform by preferential alternative splicing of a previously unobserved exon, EMBO J, 6(8):2337-42 (1987).

Figure 1
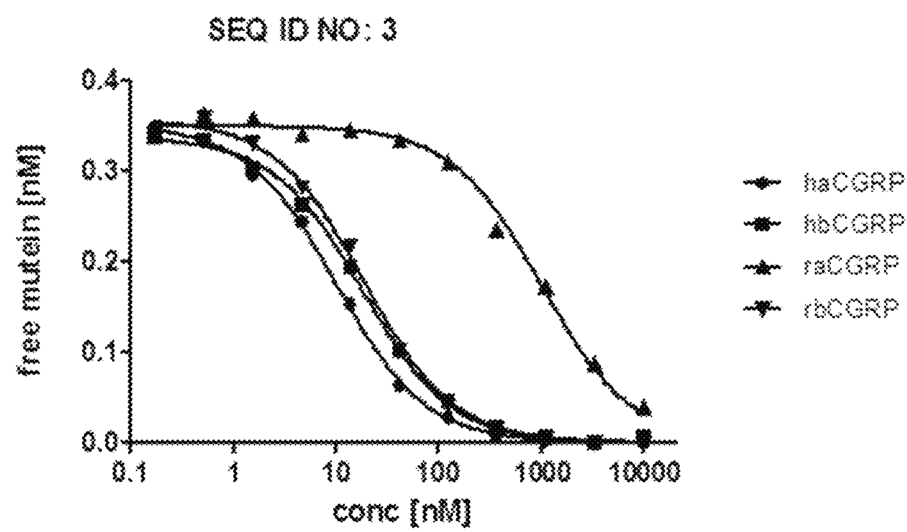
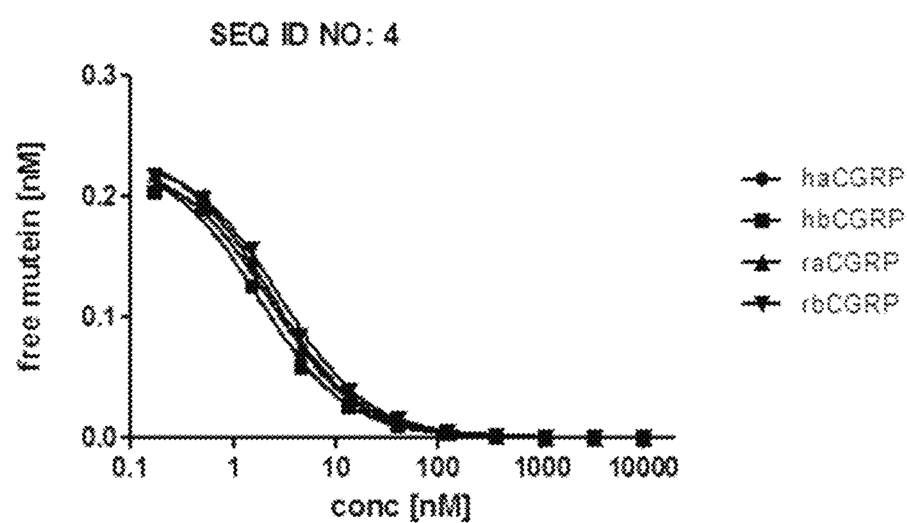

Figure 1 (contd)
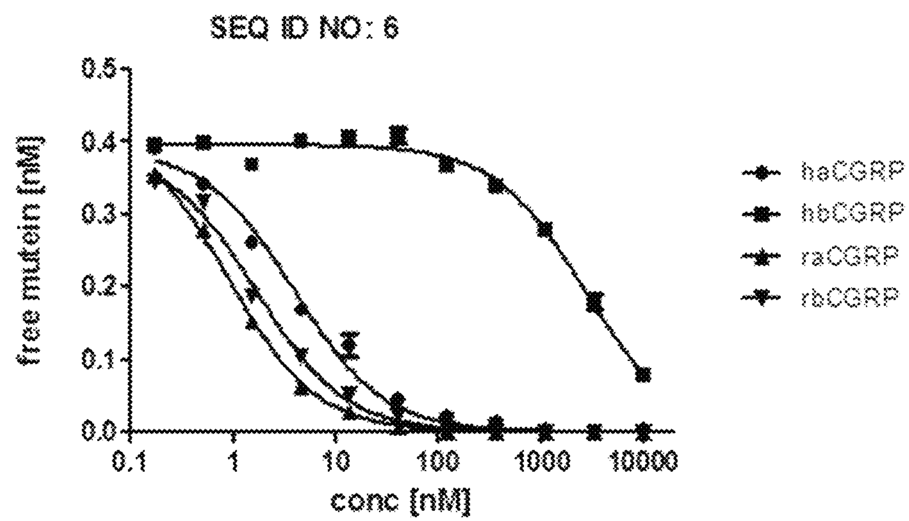
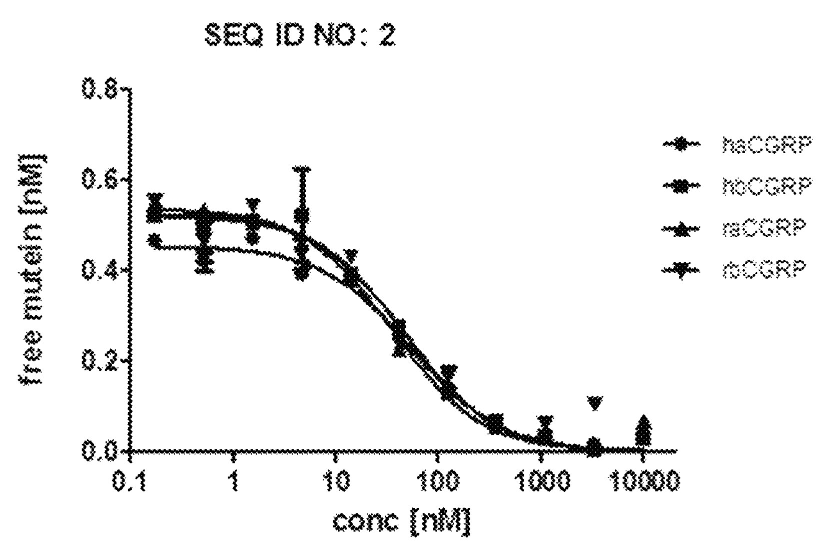

Figure 1 (contd)
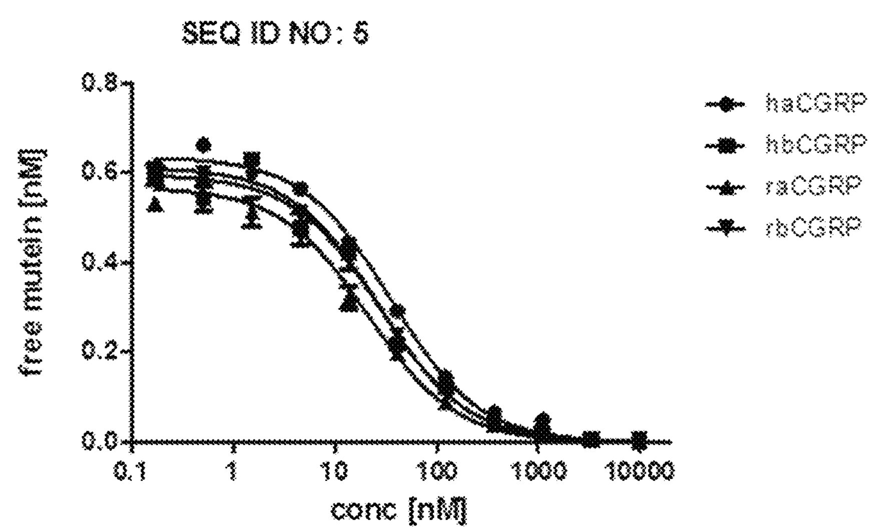

Figure 2A human alpha CGRP
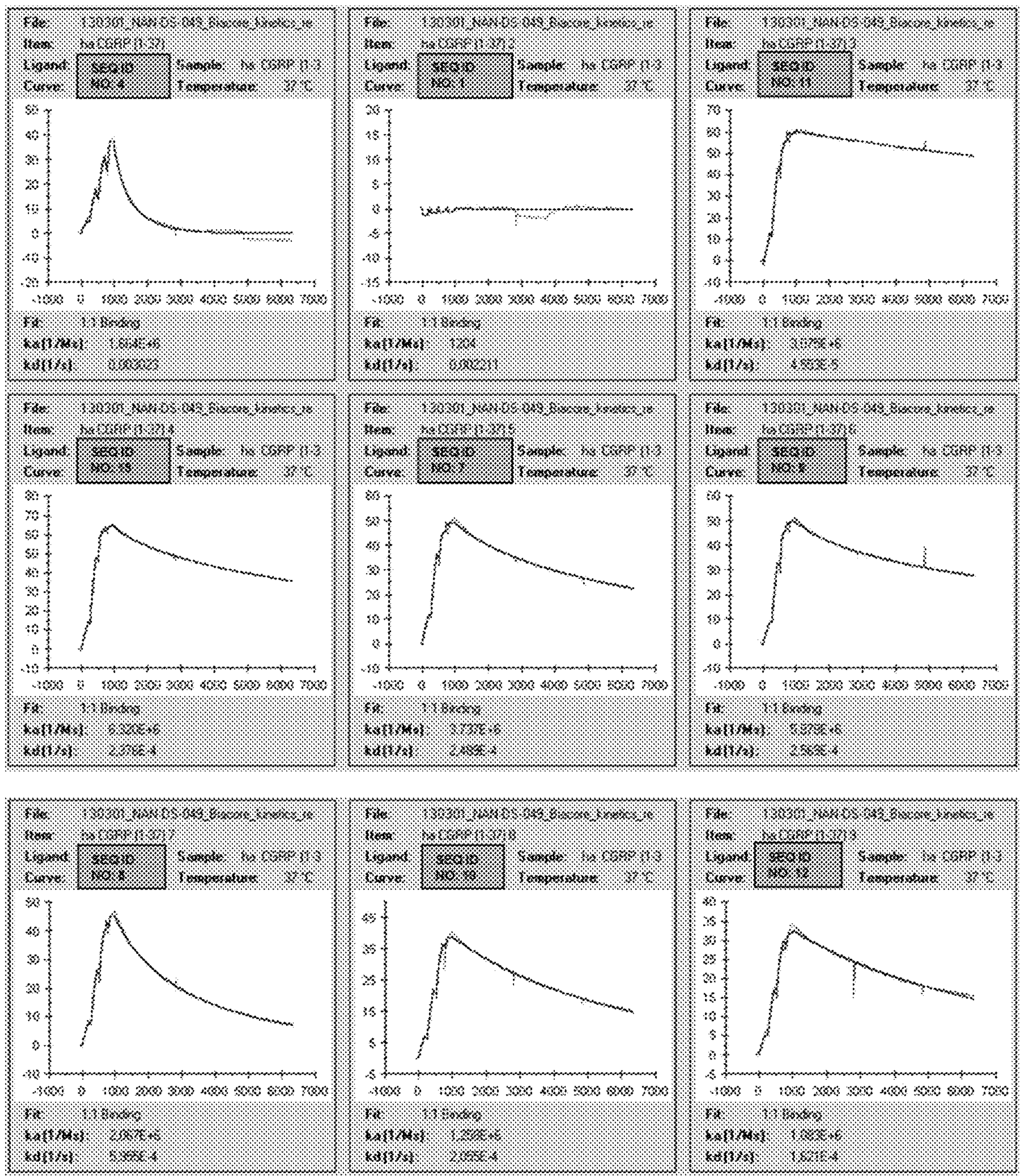

Figure 2A (contd)
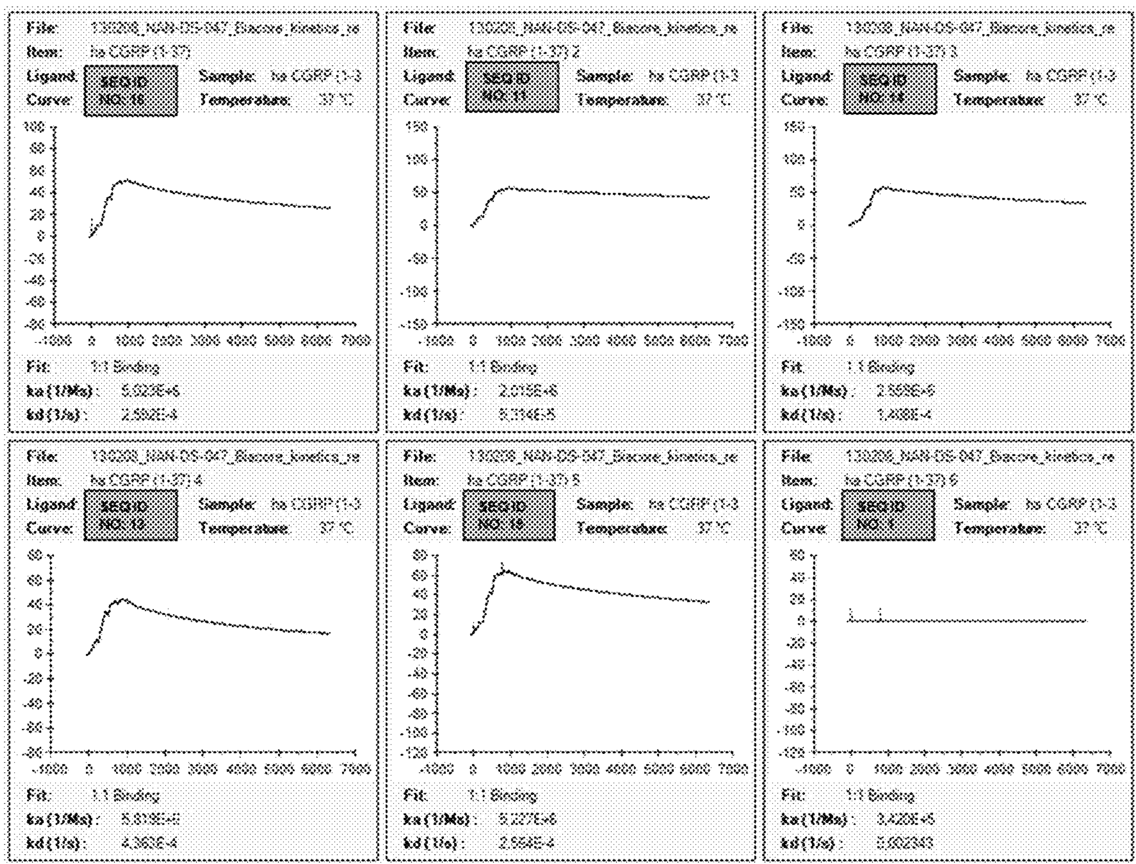

Figure 2A (contd)
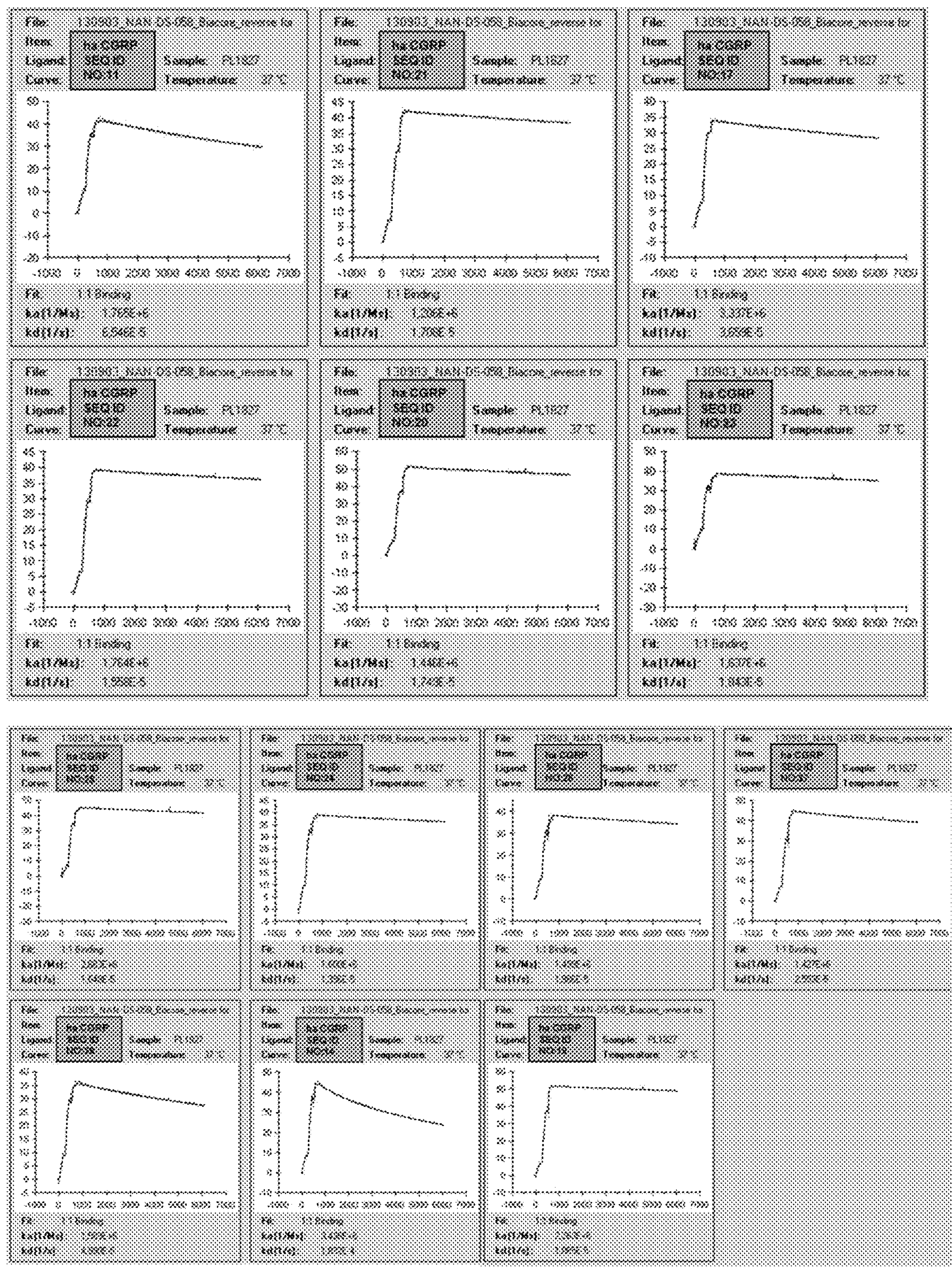

Figure 2B human beta CGRP
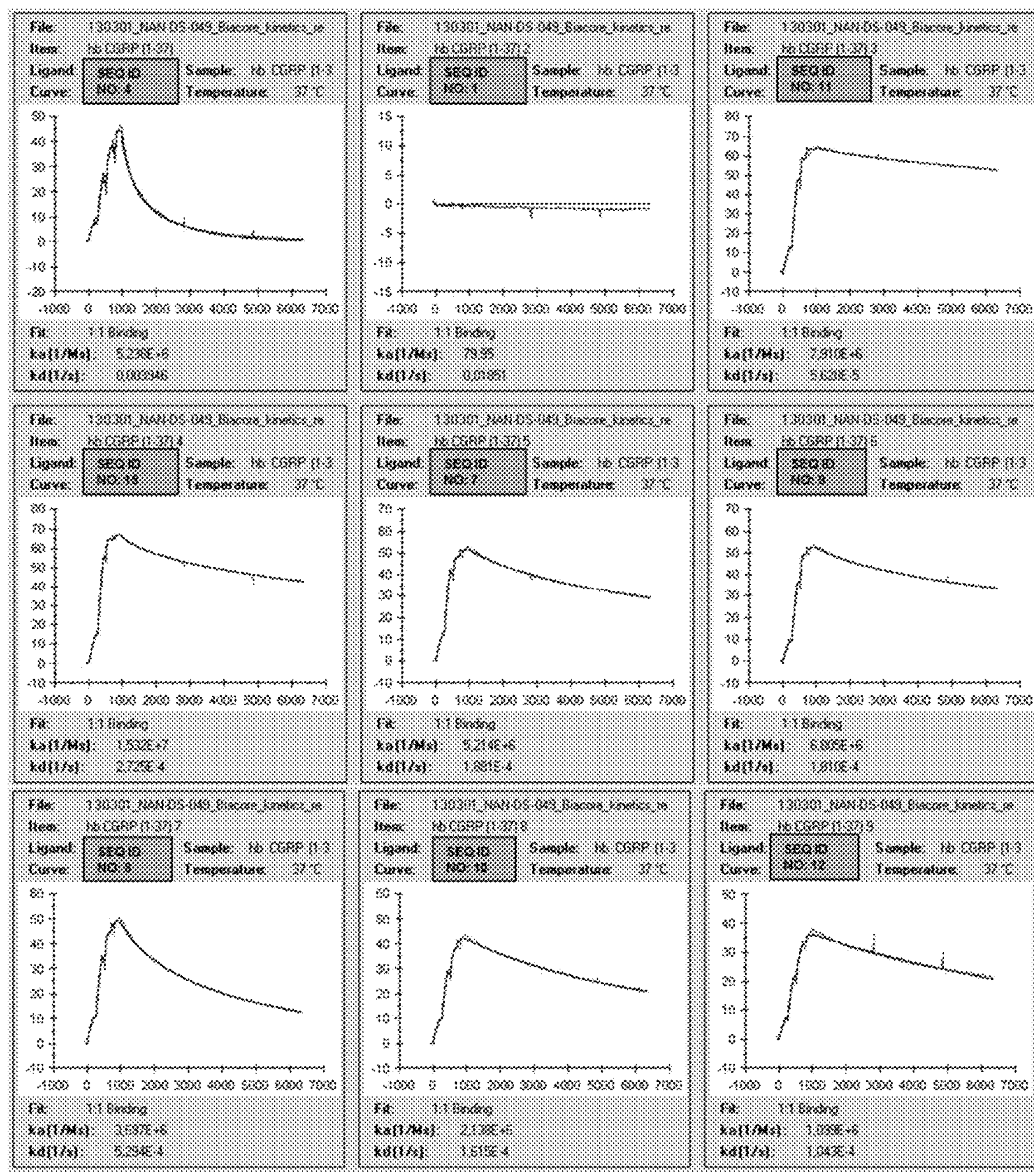

Figure 2B (contd)
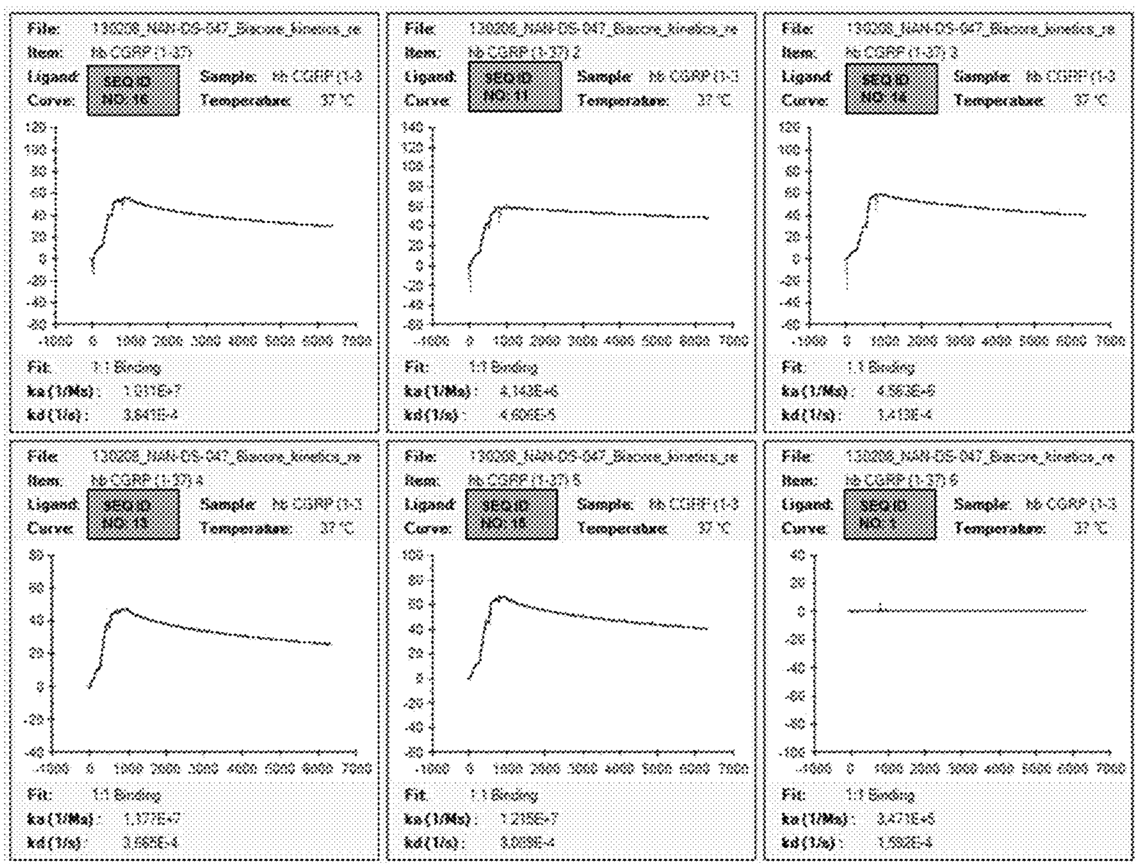

Figure 2B (contd)
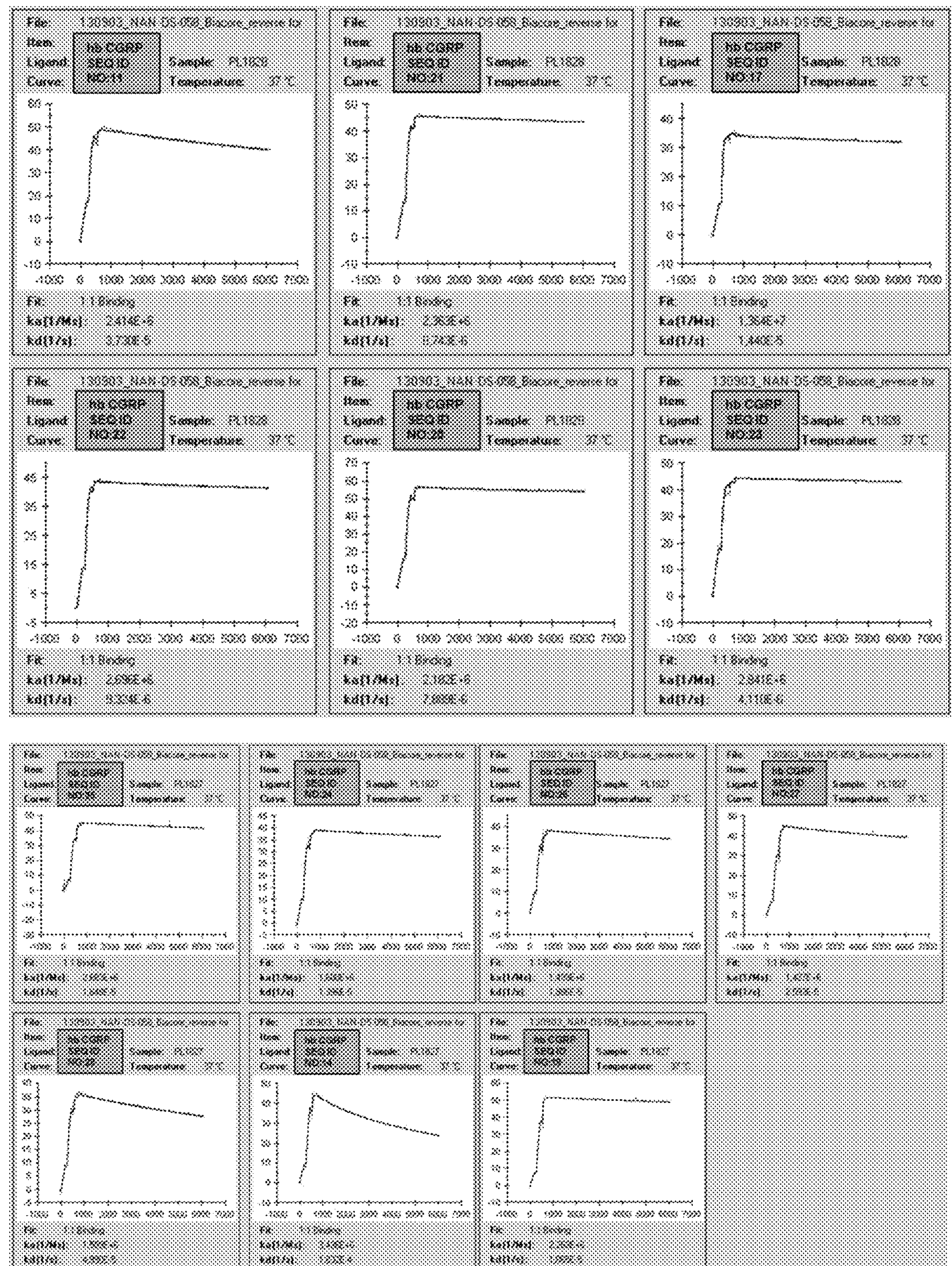

Figure 2C rat alpha CGRP
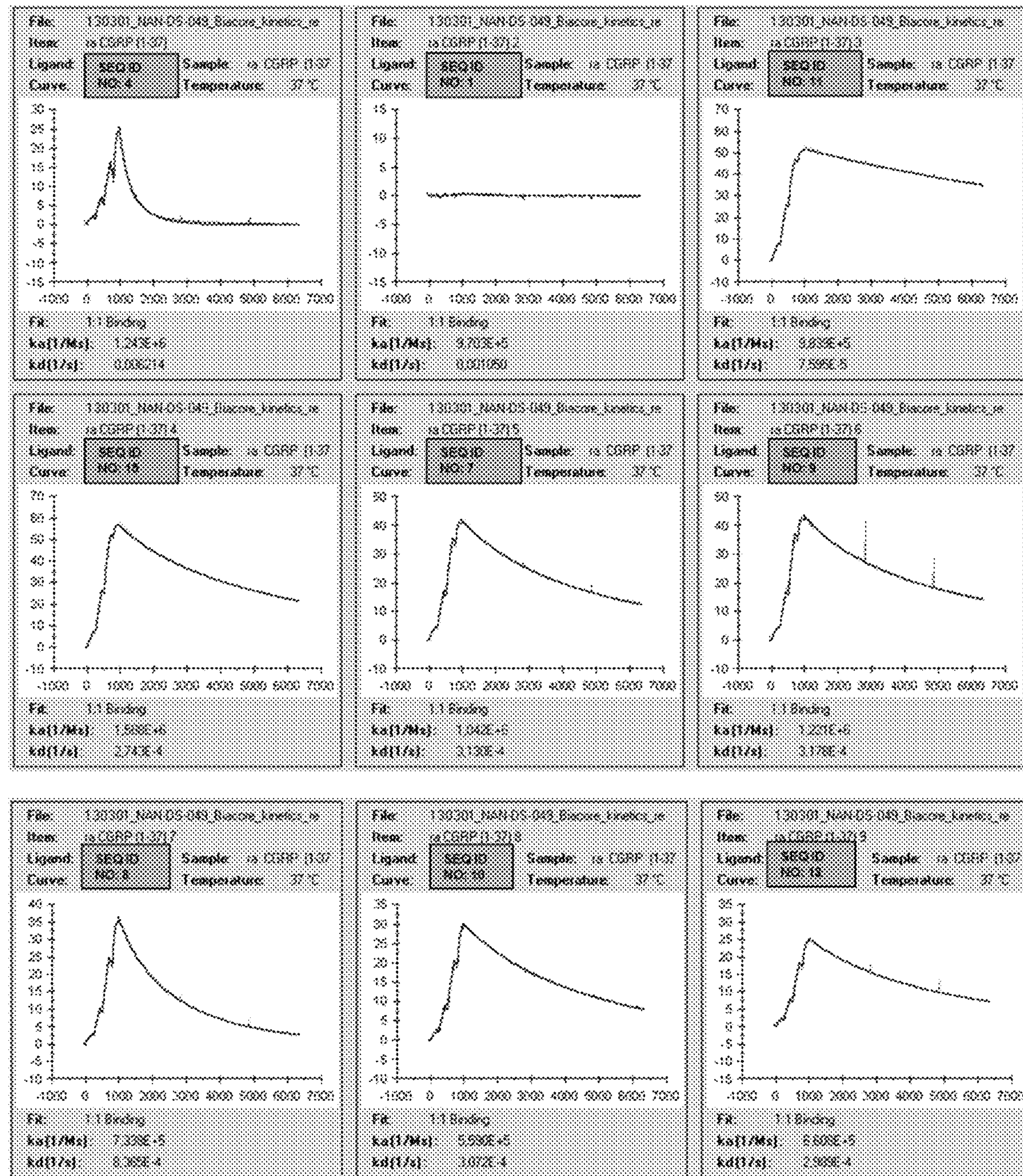

Figure 2C (contd)
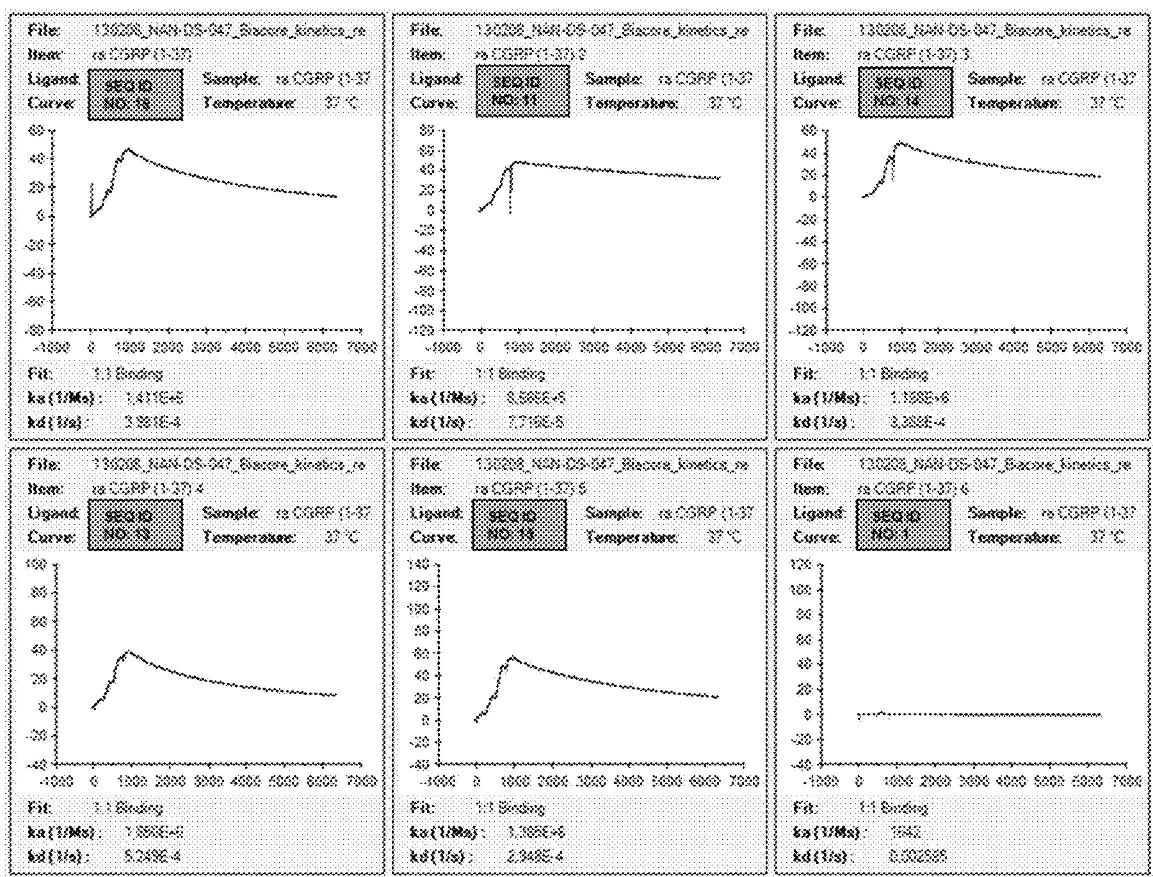

Figure 2C (contd)
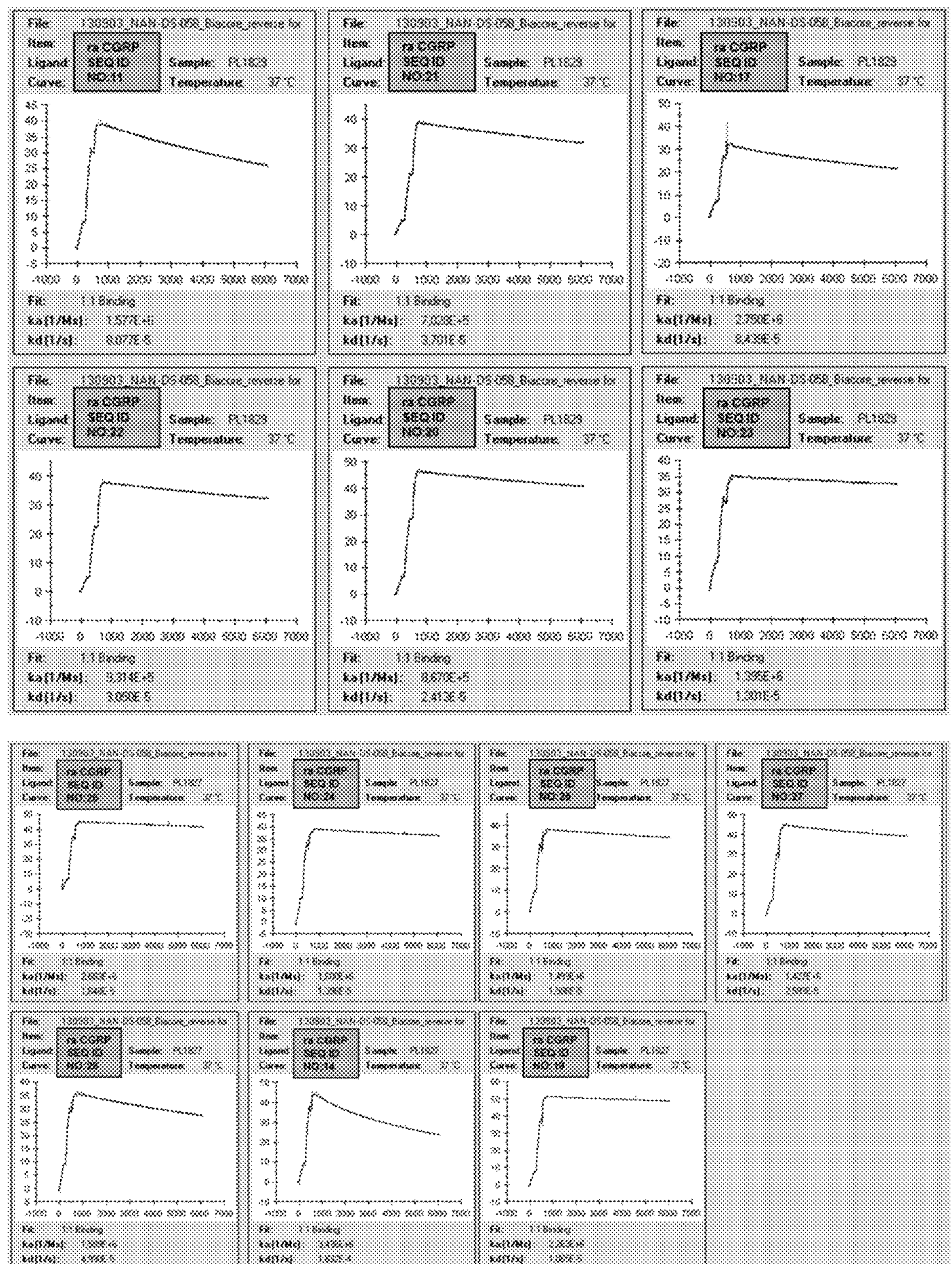

Figure 2D rat beta CGRP
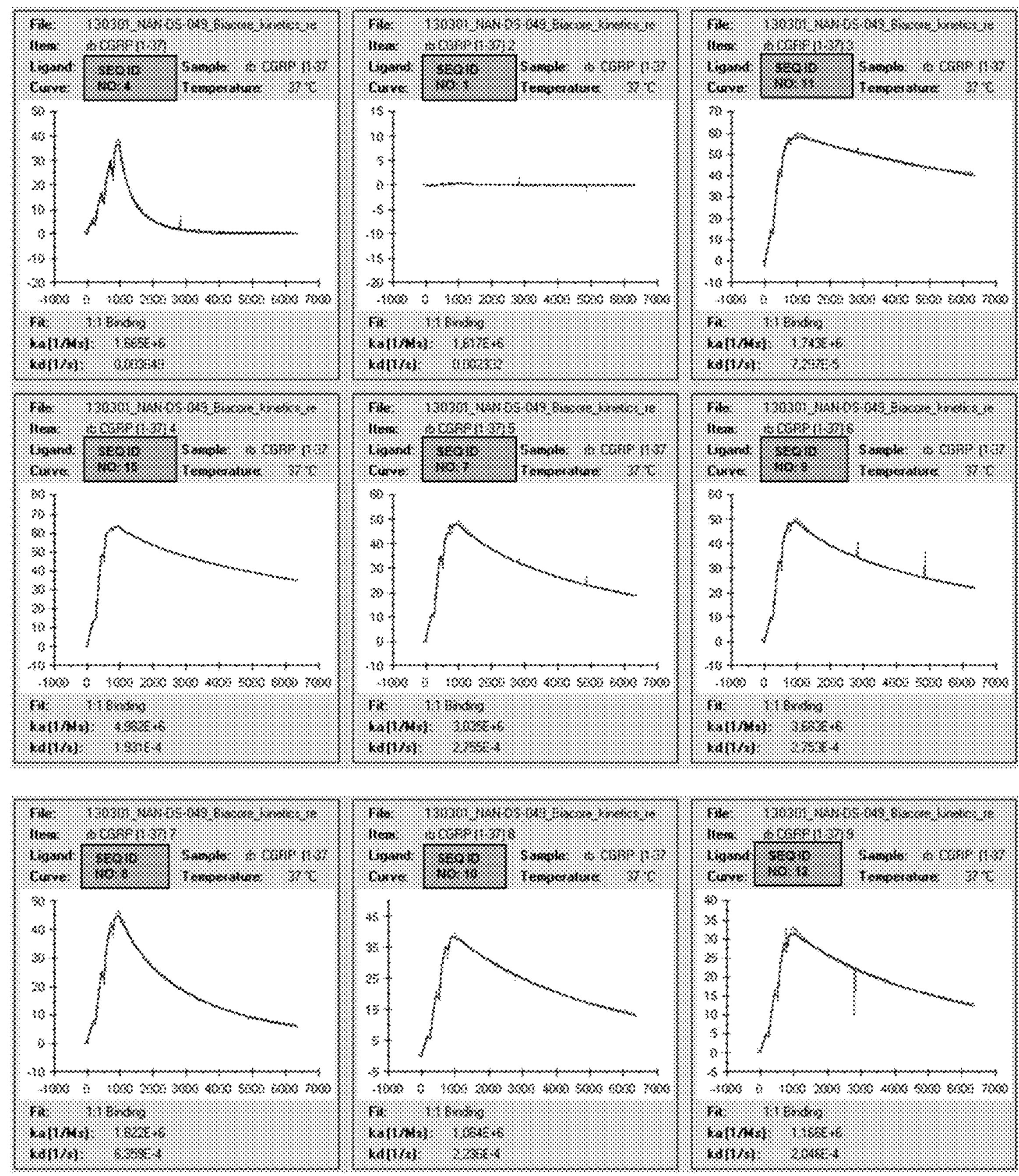

Figure 2D (contd)
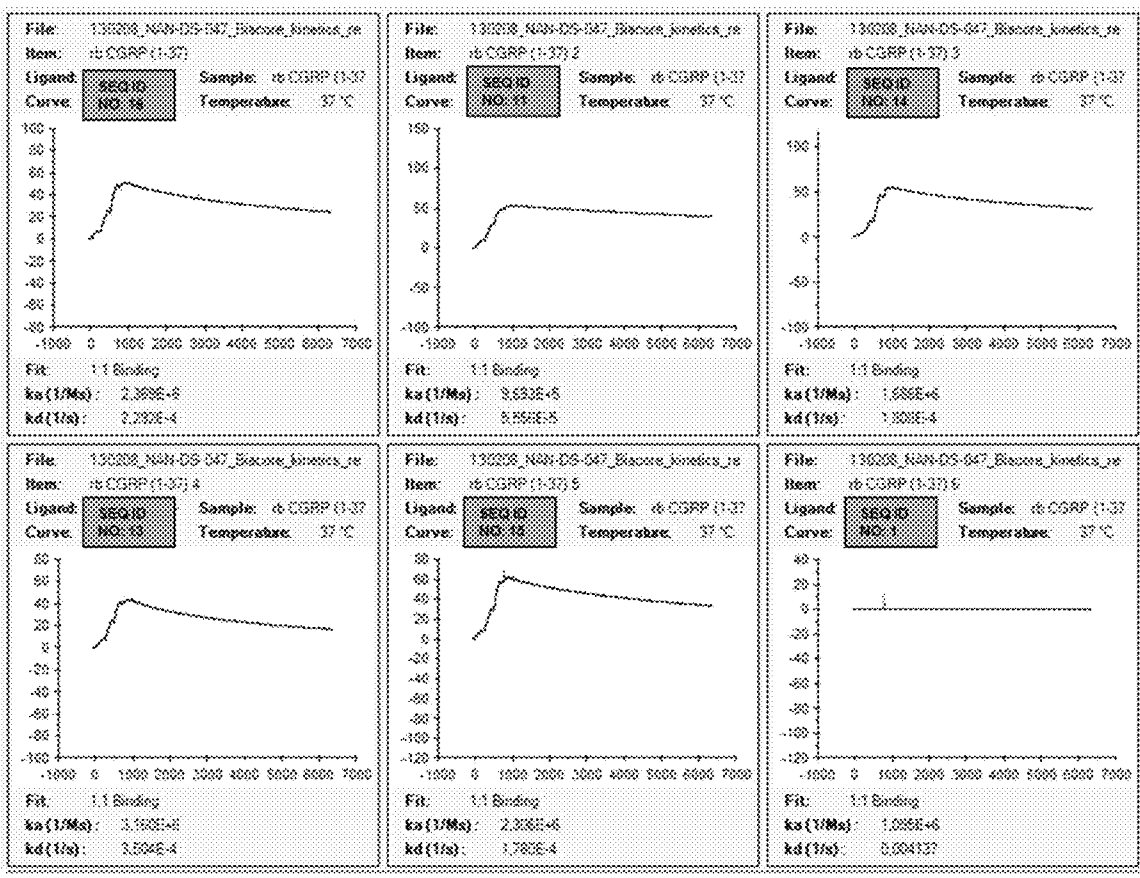

Figure 2D (contd)
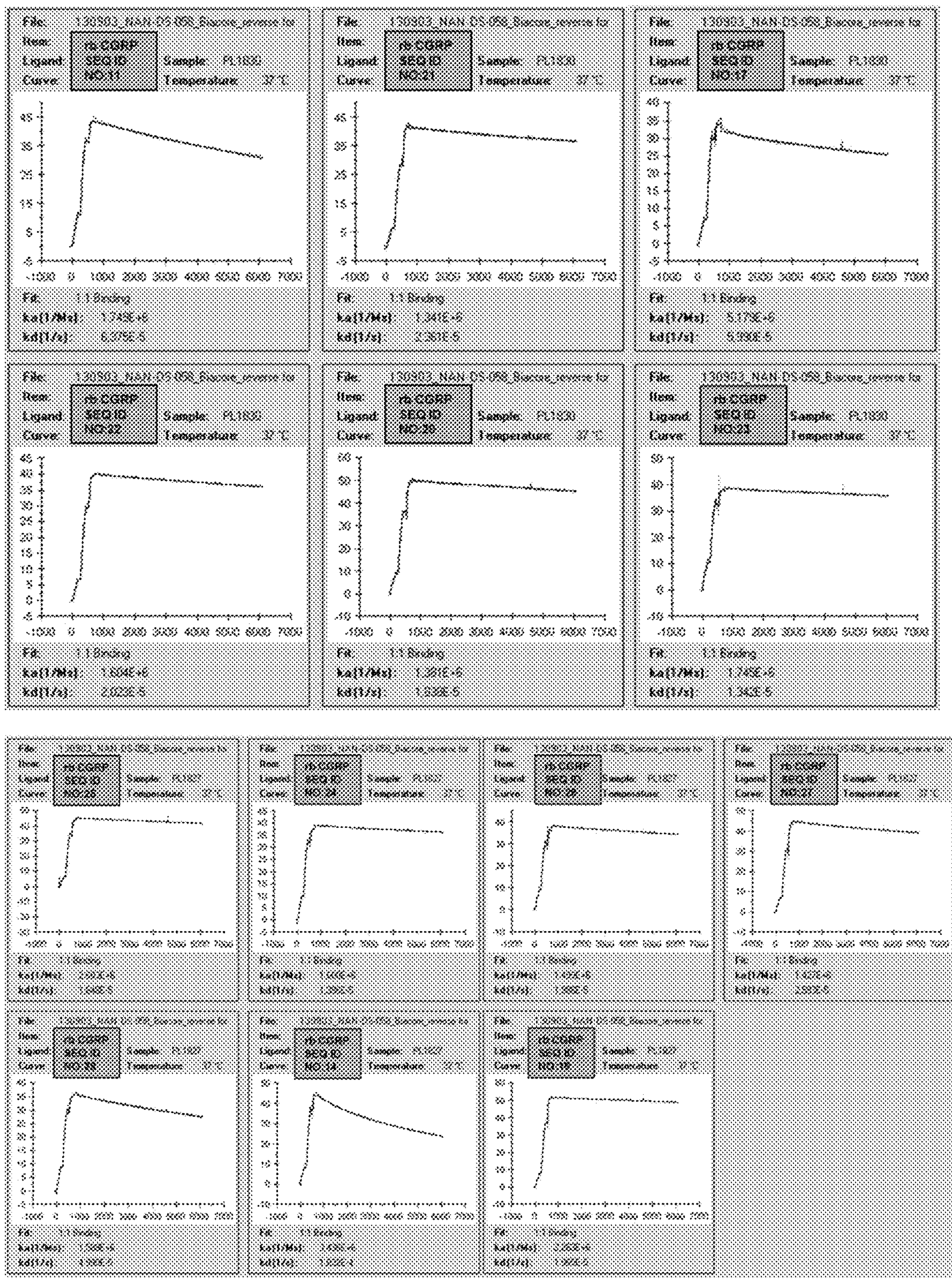

Figure 3
Figure 3A human alpha CGRP
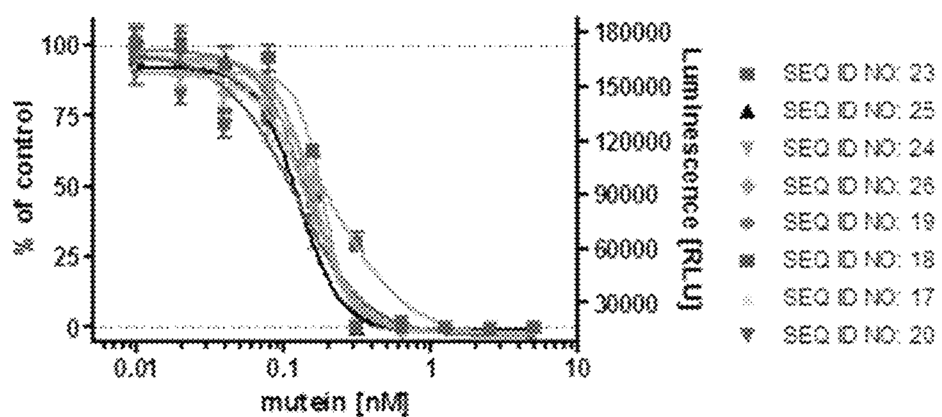
Figure 3B human beta CGRP
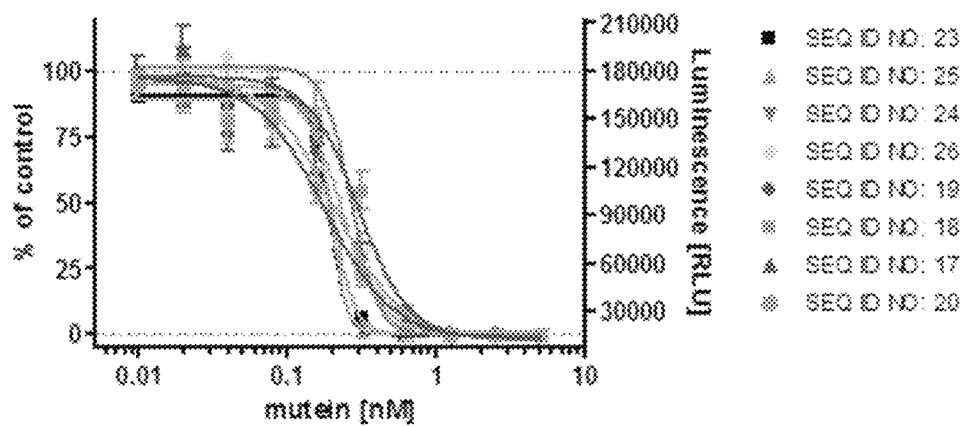

Figure 3C rat alpha CGRP
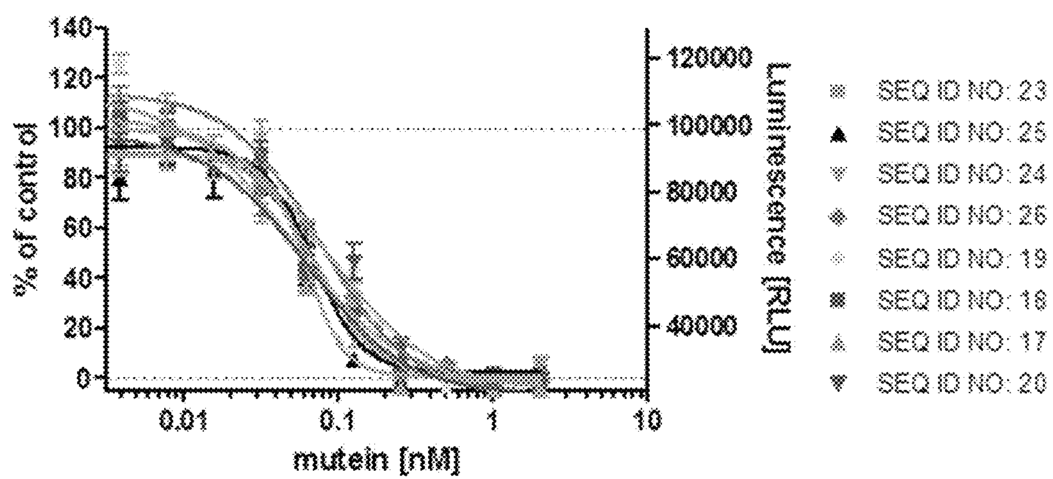
Figure 3D rat beta CGRP
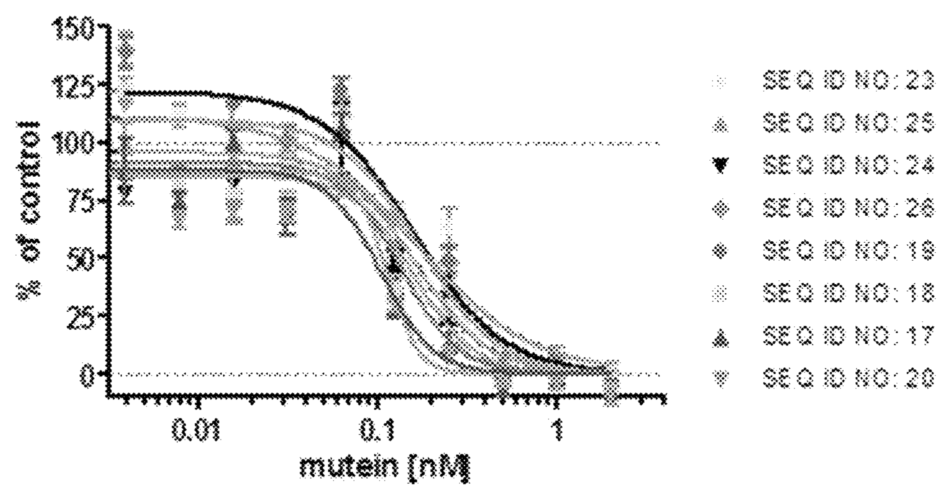

Figure 4A human alpha CGRP
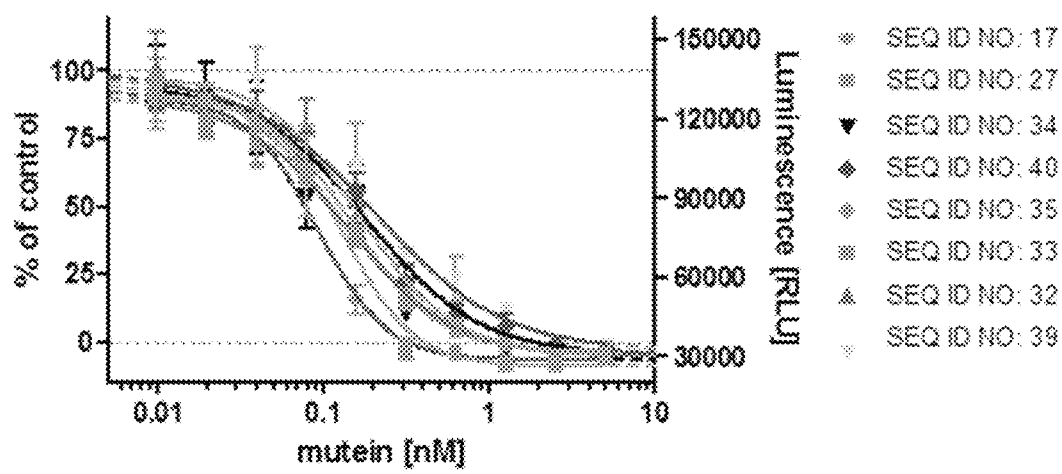
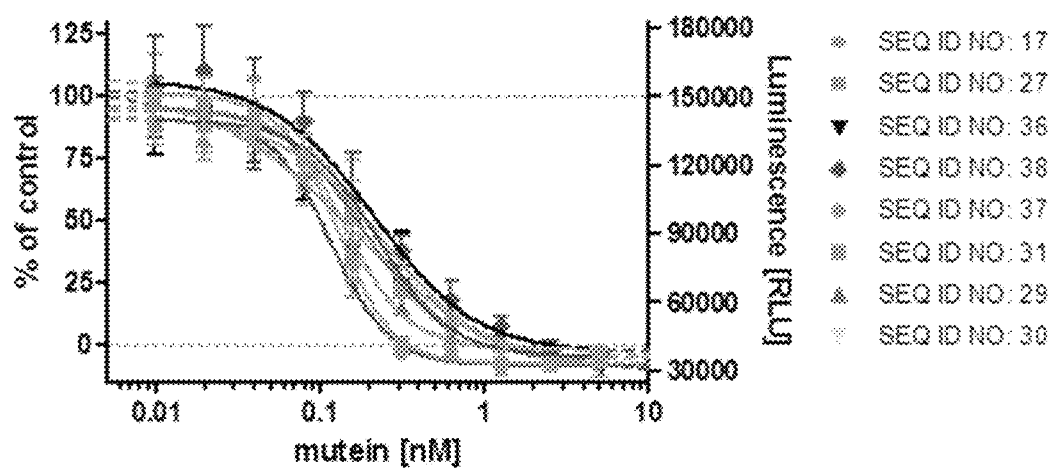

Figure 4B human beta CGRP
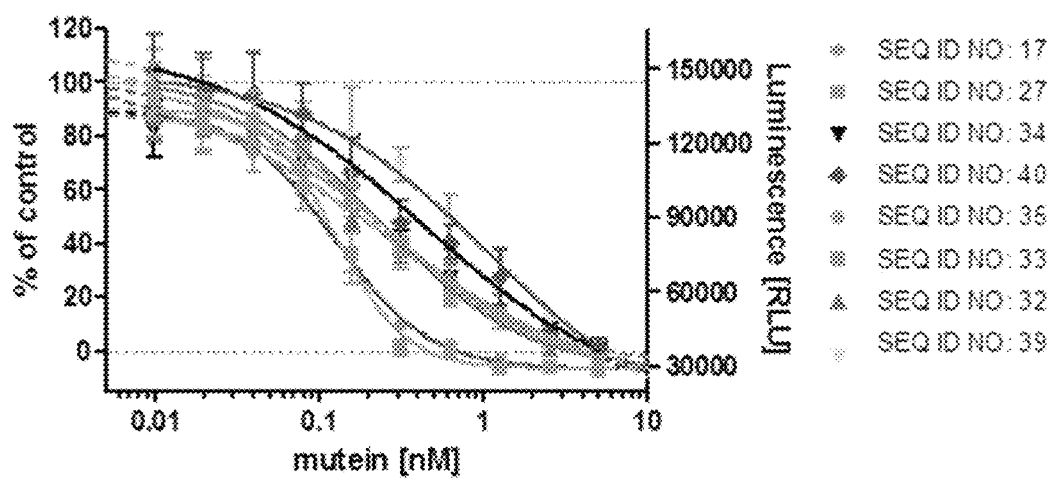
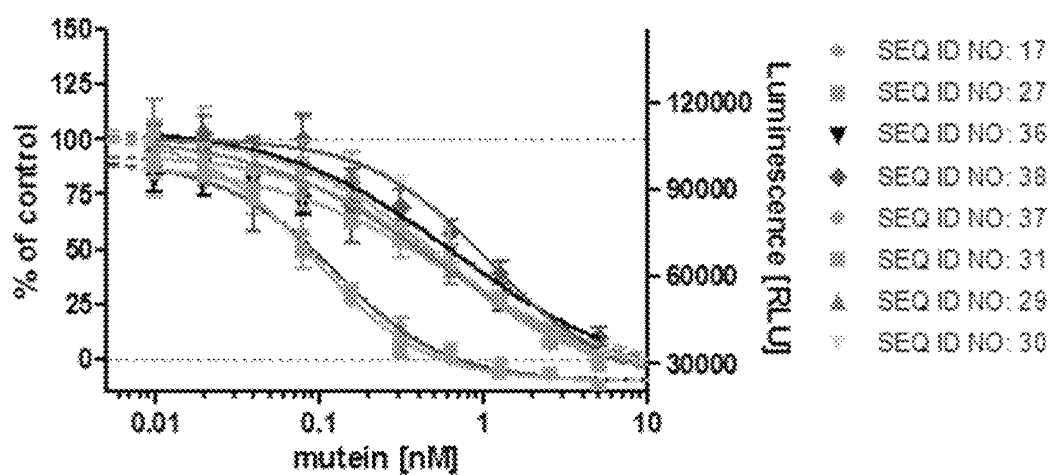

Figure 5
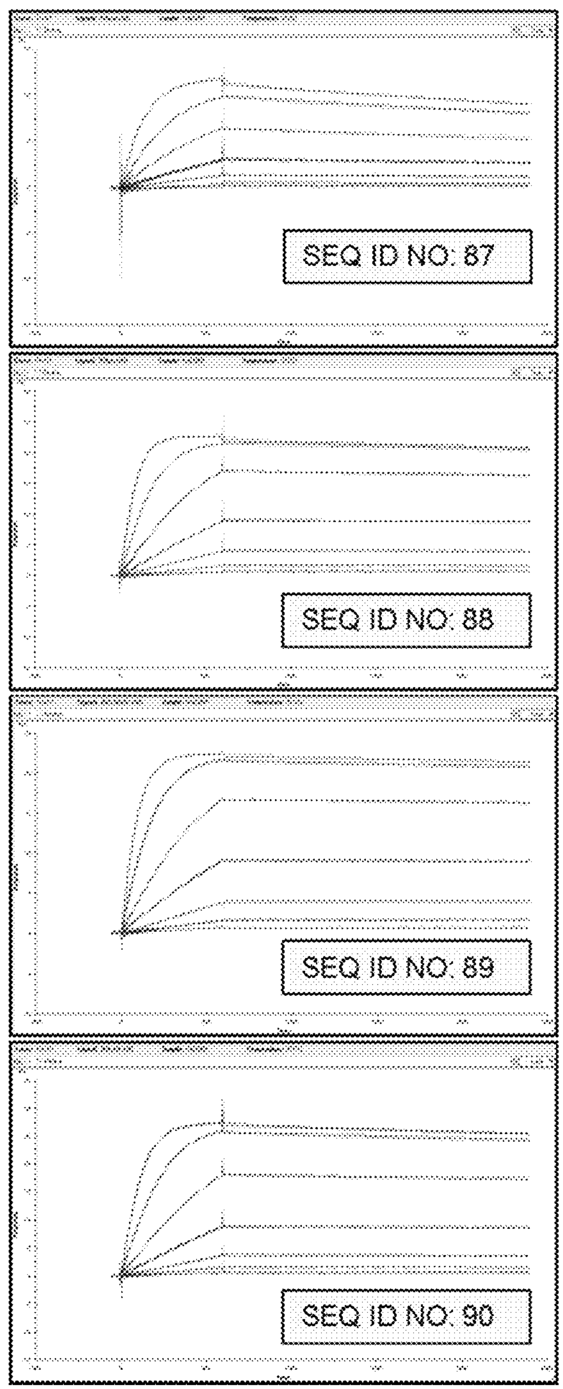
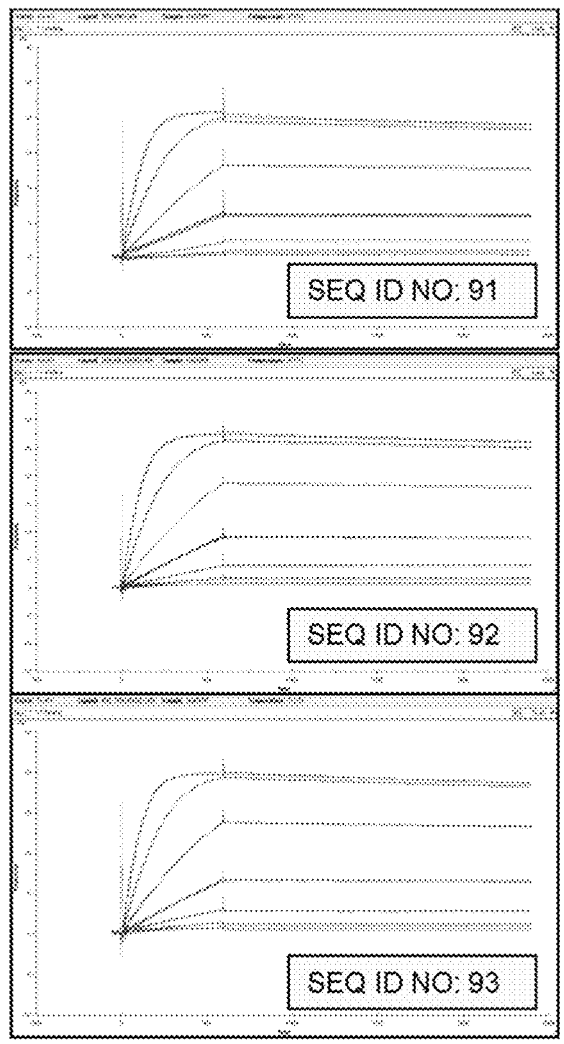

PROTEINS SPECIFIC FOR CALCITONIN GENE-RELATED PEPTIDE

CROSS-REFERENCE TO RELATED APPLICATIONS

This application is a division of U.S. application Ser. No. 15/371,698, filed Dec. 7, 2016, now U.S. Pat. No. 10,400,016, which claims priority to U.S. Provisional Application No. 62/265,792, filed Dec. 10, 2015, the entire contents of each of which are incorporated herein by reference.

SEQUENCE LISTING

The instant application contains a Sequence Listing which has been submitted in ASCII format via EFS-WEB and is hereby incorporated by reference in its entirety. Said ASCII copy, created on Oct. 1, 2019, is named 2013101-0097_SL.txt and is 119 KB.

I. BACKGROUND

Calcitonin gene-related peptide (CGRP) is a vasoactive neuropeptide secreted by the nerves of the central and peripheral nervous systems, where CGRP-containing neurons are closely associated with blood vessels. CGRP-mediated vasodilatation is also associated with neurogenic inflammation, as part of a cascade of events that results in extravasation of plasma and vasodilatation of the microvasculature and is present in migraines.

CGRP exists as highly homologous α and β isoforms in both human and rat although each is encoded by a distinct gene. The α and β isoforms of the CGRP peptides differ by three amino acids in humans and one amino acid in rats. The amino acid sequences of CGRP peptides are well conserved among species and are considered members of a family of peptides that includes amylin, calcitonin, and adrenomedullin.

CGRP is thus divided into at least two subtypes, denoted as α-CGRP or CGRP1 and β-CGRP or CGRP2 (Pharmacol. Rev 54:233-246, 2002). The existence of at least two CGRP subtypes had been proposed from differential antagonist affinities and agonist potencies in a variety of in vivo and in vitro bioassays. (Dennis et al., hCGRP8-37, A calcitonin gene-related peptide antagonist revealing calcitonin gene-related peptide receptor heterogeneity in brain and periphery, J. Pharmacol. Exp. Ther., 254:123-128 (1990); Dennis et al., Structure-activity profile of calcitonin gene-related peptide in peripheral and brain tissues. Evidence for receptor multiplicity, J. Pharmacol. Exp. Ther., 251:718-725 (1989); Dumont et al., A potent and selective CGRP agonist, [Cys(Et)2,7]hCGRP alpha: comparison in prototypical CGRP1 and CGRP2 in vitro bioassays, Can. J. Physiol. Pharmacol, 75:671-676 (1997)).

The CGRP1 subtype was found to be sensitive to the antagonist fragment CGRP(8-37). (Chiba et al., Calcitonin gene-related peptide receptor antagonist human CGRP-(8-37), Am. J. Physiol, 256:E331-E335 (1989); Dennis et al (1990); Mimeault et al, Comparative affinities and antagonistic potencies of various human calcitonin gene-related peptide fragments on calcitonin gene-related peptide receptors in brain and periphery, J. Pharmacol. Exp. Ther., 258:1084-1090 (1991)). By contrast, the CGRP was sensitive to linear human CGRP (hCGRP) analogs, in which the cysteine residues at positions 2 and 7 were derivatized (e.g., with acetoaminomethyl [Cys(ACM)2'7] or ethylamide [Cys(Et)2'7]) but CGRP receptor was insensitive to fragment CGRP (8-37). (Dennis et al (1989); Dennis et al (1990); Dumont et al (1997)). Three calcitonin receptor stimulating peptides (CRSPs) have also been identified in a number of mammalian species; the CRSPs may form a new subfamily in the CGRP family. (Katafuchi, T and Minamino, N, Structure and biological properties of three calcitonin receptor-stimulating peptides, novel members of the calcitonin gene-related peptide family, Peptides, 25(11):2039-2045 (2004)).

CGRP mediates its effects through a heteromeric receptor composed of a G protein-coupled receptor called calcitonin receptor-like receptor (CALCRL) and a receptor activity-modifying protein (RAMP1). CGRP receptors have been identified and pharmacologically evaluated in several tissues and cells, including brain, cardiovascular, endothelial and smooth muscle. Multiple CGRP receptors have been characterized based on distinct pharmacological properties. The calcitonin superfamily peptides act through seven-transmembrane-domain G-protein-coupled receptors (GPCRs). The calcitonin receptor ("CT", "CTR" or "CT receptor") and CGRP receptors are type II ("family B") GPCRs, which family includes other GPCRs that recognize regulatory peptides such as secretin, glucagon and vasoactive intestinal polypeptide (VIP). The best characterized splice variants of human calcitonin receptor differ depending on the presence (formerly CTRn+ or CTRI, now known as CTˆ)) or absence (the major splice variant, formerly CTRπ_ or CTR2, now known as CT(a)) of 16 amino acids in the first intracellular loop. (Gorn et al., Expression of two human skeletal calcitonin receptor isoforms cloned from a giant cell tumor of bone: the first intracellular domain modulates ligand binding and signal transduction, J. Clin. Invest., 95:2680-2691 (1995); Hay et al., Amylin receptors: molecular composition and pharmacology, Biochem. Soc. Trans., 32:865-867 (2004); Poyner et al., 2002).

CGRP is widely distributed in sensory nerves, both in the peripheral and central nervous system and displays a large number of different biological activities. When released from trigeminal and other nerve fibers, CGRP is thought to mediate its biological responses by binding to specific cell surface receptors. The biological activities of CGRP include the regulation of neuromuscular junctions, of antigen presentation within the immune system, of vascular tone and of sensory neurotransmission. (Poyner, D. R., Calcitonin gene-related peptide: multiple actions, multiple receptors, Pharmacol. Ther., 56:23-51 (1992); Muff et al., Calcitonin, calcitonin gene-related peptide, adrenomedullin and amylin: homologous peptides, separate receptors and overlapping biological actions, Eur. J. Endocrinol., 133: 17-20 (1995)).

There is a great need, therefore, to identify new compounds that specifically recognize and bind CGRP. Such compounds would be useful for diagnostic screening and therapeutic intervention in disease states that are associated with CGRP activity. Accordingly, it is an object of the present disclosure to provide specific binding compounds of CGRP for modulating CGRP activity. Such compounds disclosed herein take the form of muteins derived from human lipocalin 2 (also known as neutrophil gelatinase associated lipocalin, "hNGAL").

II. DEFINITIONS

The following list defines terms, phrases, and abbreviations used throughout the instant specification. All terms listed and defined herein are intended to encompass all grammatical forms.

As used herein, "CGRP", unless specified as being from a non-human species (e.g., "rat CGRP," "monkey CGRP," etc.), means human α-CGRP and/or human β-CGRP.

As used herein, "α-CGRP" or "alpha CGRP", unless specified as being from a non-human species (e.g., "rat α-CGRP," "monkey α-CGRP," etc.), means human CGRP1, a full-length protein defined by Swiss Prot P06881 or a biologically active fragment thereof (e.g., a fragment of the CGRP1 protein which is capable of inducing plasma protein extravasation in vitro or in vivo).

As used herein, "β-CGRP" or "beta CGRP", unless specified as being from a non-human species (e.g., "rat β-CGRP," "monkey β-CGRP," etc.), means human CGRP2, a full-length protein defined by Swiss Prot P10092 or a biologically active fragment thereof (e.g., a fragment of the CGRP2 protein which is capable of inducing plasma protein extravasation in vitro or in vivo).

As used herein, "rat CGRP" means rat α-CGRP and/or rat β-CGRP. Rat α-CGRP (alpha CGRP) or rat CGRP1 is a full-length protein defined by Swiss Prot P01256 or a biologically active fragment thereof. Rat β-CGRP (beta CGRP) or rat CGRP2 is a full-length protein defined by Swiss Prot P10093 or a biologically active fragment thereof.

As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of human lipocalin 2) to a selected target (in the present case, CGRP), can be measured (and thereby KD values of a mutein-ligand complex be determined) by a multitude of methods known to those skilled in the art. Such methods include, but are not limited to, fluorescence titration, direct ELISA, competition ELISA, calorimetric methods, such as isothermal titration calorimetry (ITC), and surface plasmon resonance (SPR). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, direct ELISA, competition ELISA or SPR, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular mutein for a given ligand. This means that there may be a slight deviation in the measured $K_D$ values or a tolerance range depending, for example, on whether the $K_D$ value was determined by SPR, by competition ELISA, or by direct ELISA.

As used herein, a compound such as a mutein of the disclosure "specifically binds" a target (for example, CGRP) or has "binding specificity" for a target if it is able to discriminate between that target and one or more reference targets, since binding specificity is not an absolute, but a relative property. "Specific binding" can be determined, for example, in accordance with Western blots, ELISA-, RIA-, ECL-, IRMA-tests, IHC and peptide scans.

The term "human lipocalin 2" or "human Lcn 2" or "human NGAL" or "hNGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 1 is used as reference sequence.

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. The term "mutein," as used herein, also includes its functional fragments or variants. Fragments or variants of particular muteins described in the present disclosure preferably retain the function of binding to CGRP, e.g. with detectable or even higher affinity, and such fragments or variants are "functional fragments or variants" of the reference mutains disclosed herein.

The term "fragment" as used herein in connection with the muteins of the disclosure relates to proteins or peptides derived from full-length mature human lipocalin 2 that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature human lipocalin 2 and are usually detectable in an immunoassay of the mature human lipocalin 2.

In general, the term "fragment", as used herein with respect to the corresponding protein ligand of a mutein of the disclosure or of the combination according to the disclosure, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature human lipocalin 2 can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the disclosure.

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any mutein of the disclosure).

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to 10) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a mutein different from the wild-type human lipocalin 2 corresponds to a certain position in the amino acid sequence of the wild-type human lipocalin 2, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, the wild-type human lipocalin 2 can serve as "subject sequence" or "reference sequence", while the amino acid sequence of a mutein different from the wild-type human lipocalin 2 described herein serves as "query sequence". The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By a "native sequence" human lipocalin 2 is meant human lipocalin 2 that has the same amino acid sequence as the corresponding polypeptide derived from nature. Thus, a native sequence human lipocalin 2 can have the amino acid sequence of the respective naturally-occurring human lipocalin 2. Such native sequence polypeptide can be isolated from nature or can be produced by recombinant or synthetic means. The term "native sequence" polypeptide specifically encompasses naturally-occurring truncated or secreted forms of the human lipocalin 2, naturally-occurring variant forms such as alternatively spliced forms and naturally-occurring allelic variants of human lipocalin 2. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) human lipocalin 2. Similarly, the position of a given nucleotide in accordance with the present disclosure which may be substituted may vary due to deletions or additional nucleotides elsewhere in a mutein or wild type human lipocalin 2 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a mutein based on a reference scaffold in accordance with the disclosure, it is preferably to be understood that the positions of nucleotides/amino acids are structurally corresponding to the positions elsewhere in a mutein or wild-type human lipocalin 2, even if they may differ in the indicated number.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

The term "metastasis" according to the disclosure refers to the transmission of cancerous cells from the primary tumor to one or more sites elsewhere in a patient where secondary tumors develop. Means to determine if a cancer has metastasized are known in the art and include bone scan, chest X-ray, CAT scan, MRI scan, and tumor marker tests. The term "prevention of metastasis" means that the metastasis of the primary, tumor or cancer is prevented, delayed, or reduced and thus the development of secondary tumors is prevented, delayed, or reduced. Preferably the metastasis i.e secondary tumors of the lung are prevented or reduced, which means that metastatic transmission of cancerous cells from the primary tumor to the lung is prevented or reduced.

The term "cancer" as used herein refers to proliferative diseases, such as lymphomas, lymphocytic leukemias, lung cancer, non-small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "vascular diseases" includes Cancer, Inflammatory diseases, Atherosclerosis, Ischemia, Trauma, Sepsis, chronic obstructive pulmonary disease (COPD), Asthma, Diabetes, age-related macular degeneration (AMD), Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes (such as proliferative retinopathies or AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A., Vascular diseases, In: Pathobiology of ocular disease, A dynamic approach, Garner, A., and Klintworth, G. K. (eds.), 2nd edition, Marcel Dekker, New York (1994), pp 1625-1710).

The term "antibody", as used herein, is intended to refer to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_1$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-CGRP antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Non-limiting examples of antigen-binding fragments include: (i) Fab fragments; (ii) $F(ab')_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments comprising a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

III. DESCRIPTIONS OF FIGURES

FIG. 1: shows binding of selected CGRP-specific lipocalin muteins (SEQ ID NOs: 2 to 6) to human and to rat CGRP alpha and beta as measured in a solution binding competition ELISA. Muteins bind to all four CGRP species with low nanomolar to double digit nanomolar EC50 values, except for SEQ ID NO: 3 and SEQ ID NO: 6 having lower affinity to rat alpha and human beta CGRP, respectively. The resulting EC50 values are summarized in Table 1 of Example 4.

FIGS. 2A, 2B, 2C and 2D provide typical measurements of on-rate and off-rate by SPR for the lipocalin muteins SEQ ID NO: 4, SEQ ID NOs: 7 to 17, and SEQ ID NOs: 19 to 28. The association rates (ka), the dissociation rates (kd) and the resulting dissociation constants (KD) to human and rat CGRP species (alpha and beta), respectively, are summarized in Table 2 of Example 5.

FIGS. 3A, 3B, 3C and 3D are graphical representations of the functional activity of selected CGRP-specific lipocalin muteins. The binding of the lipocalin muteins to CGRP leads to reduction of CGRP-induced cAMP production by SK-N-MC cells (human brain neuroepithelioma) or by L6 cells (rat skeletal muscle myoblasts) for human and rat CGRP species (alpha and beta), respectively. The IC50 values for all four CGRP species are in the subnanomolar to low nanomolar range and are summarized in Table 3 of Example 6.

FIGS. 4A and 48 show the inhibition of human alpha and beta CGRP-induced cAMP production by SK-N-MC cells (human brain neuroepithelioma) through binding of CGRP-specific muteins, from which the natural occurring cysteine bridge was removed by protein-engineering. The IC50 values of the cysteine-free muteins (SEQ ID NOs: 29 to 40) remain unaffected compared to those of their respective parental muteins with the cysteine bridge (SEQ ID NO: 17 and SEQ ID NO: 27) and are summarized in Table 4 of Example 7.

FIG. 5: provides typical measurements of on-rate and off-rate by SPR for the lipocalin muteins (SEQ ID NOs: 87 to 93). The resulting dissociation constants (KD) to human alpha CGRP are summarized in Table 5 of Example 9.

IV. DETAILED DESCRIPTION OF THE DISCLOSURE

The current disclosure provides a polypeptide having binding specificity for CGRP, wherein the polypeptide comprises an hNGAL mutein that binds CGRP with detectable affinity.

In some embodiments, an hNGAL mutein binding CGRP with detectable affinity may include at least one amino acid substitution of a native cysteine residue by another amino acid, for example, a serine residue. In some other embodiments, a mutein binding CGRP with detectable affinity may include one or more non-native cysteine residues substituting one or more amino acids of wild-type hNGAL. In a further particular embodiment, an hNGAL mutein according to the disclosure includes at least two amino acid substitutions of a native amino acid by a cysteine residue, hereby to form one or more cysteine bridges. In some embodiments, said cysteine bridge may connect at least two loop regions. The definition of these regions is used herein in accordance with Flower (Flower, 1996, supra, Flower, et al., 2000, supra) and Breustedt et al. (2005, supra).

A mutein or a composition thereof has specificity for CGRP as disclosed herein may have antagonist, or neutralizing or blocking activity with respect to at least one biological activity of CGRP.

In one aspect, the present disclosure includes various hNGAL muteins that bind CGRP with at least detectable affinity. In this sense, CGRP is regarded as a non-natural ligand of the reference wild-type hNGAL, where "non-natural ligand" refers to a compound that does not bind to wild-type human lipocalin 2 under physiological conditions. By engineering wild-type hNGAL with one or more mutations at certain sequence positions, the present inventors have demonstrated that high affinity and high specificity for the non-natural ligand, CGRP, is possible. In some embodiments, at 1, 2, 3, 4, 5, 6, 7, 8, 9, 10, 11, 12 or even more nucleotide triplet(s) encoding certain sequence positions on wild-type I human lipocalin 2, a random mutagenesis may be carried out through substitution at these positions by a subset of nucleotide triplets.

Further, the muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of hNGAL, such as sequence positions 8, 9, 28, 36, 38, 40, 41, 42, 44, 46, 47, 49, 52, 54, 62, 65, 66, 68, 70, 71, 72, 73, 75, 76, 77, 79, 80, 81, 83, 87, 96, 97, 98, 100, 103, 105, 106, 108, 111, 112, 114, 123, 125, 126, 127, 129, 132, 134, 135, 136, 145, 146, 175, 176, 177 and 178 of the linear polypeptide sequence of human NGAL (SEQ ID NO: 1).

A mutein of the disclosure may include the wild type (natural) amino acid sequence of the "parental" protein scaffold (such as hNGAL) outside the mutated amino acid sequence positions. In some embodiments, an hNGAL mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine: 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human lipocalin 2 as long as these deletions or insertion result in a stable folded/functional mutein (for example, hNGAL muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature hNGAL.

The amino acid sequence of an hNGAL mutein disclosed herein has a high sequence identity to the mature hNGAL (SEQ ID NO: 1) when compared to sequence identities with other lipocalins. In this general context, the amino acid sequence of a mutein of the disclosure is at least substantially similar to the amino acid sequence of the natural wild-type hNGAL, with the proviso that possibly there are gaps (as defined below) in an alignment that are the result of additions or deletions of amino acids. A respective sequence of a mutein of the disclosure, being substantially similar to the sequences of the mature hNGAL, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the mature hNGAL, with the proviso that the altered position or sequence is retained and that one or more gaps are possible.

As used herein, a mutein of the disclosure "specifically binds" a target (for example, CGRP) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the muteins of the disclosure are fused at its N-terminus and/or its C-terminus to a fusion partner, which, in some particular embodiments, is a protein, or a protein domain or a peptide. In some embodiments, the protein domain may extend the serum half-life of the mutein. In further particular embodiments, the protein domain is an Fc part of an immunoglobulin, a CH3 domain of an immunoglobulin, a CH4 domain of an immunoglobulin, an albumin binding peptide, or an albumin binding protein.

In another embodiment, the muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immoglobulin, a CH4 domain of an immunoglobulin, an albumin binding peptide, and an albumin binding protein.

In yet another embodiment, the current disclosure relates to a nucleic acid molecule comprising a nucleotide sequence encoding a mutein disclosed herein.

In another embodiment, the current disclosure relates to an expression vector comprising said nucleic acid molecule.

In another embodiment, the disclosure encompasses a host cell or a transformed cell comprising said nucleic acid molecule.

In another embodiment, the disclosure encompasses a method for producing a mutein disclosed herein using a host cell or a transformed cell comprising said nucleic acid molecule.

In another embodiment, the disclosure encompasses a pharmaceutical composition comprising a mutein disclosed herein as an active ingredient.

A. Exemplary Muteins Specific for CGRP

In one aspect, the present disclosure relates to a novel, specific-binding human lipocalin 2 (human Lcn2 or hNGAL) mutein specific for CGRP.

One embodiment of the current disclosure relates to an hNGAL mutein that is capable of binding at least one of human α-CGRP (SEQ ID NO: 80) and human β-CGRP (SEQ ID NO: 81) with detectable affinity, such as an affinity measured by a $K_D$ of about 200 nM or lower, such as about 150 nM or lower, for example, when measured in a competition ELISA assay essentially described in Example 4.

In one aspect, the current disclosure provides an hNGAL mutein that may be further capable of binding CGRP with a $K_D$ of about 5 nM or lower, such as about 2 nM or lower, for example, when measured by Biacore T200 instrument in a SPR based assay essentially described in Example 5.

In some other embodiments, an hNGAL mutein of this disclosure may be further capable of inhibiting or reducing CGRP induced cAMP production with an IC50 value of about 5 nM or lower, such as about 1.7 nM or lower, in a SK-N-MC cell-based functional assay essentially described in Example 6.

In some particular embodiments, an hNGAL mutein of the disclosure may be further capable binding at least one of rat α-CGRP (SEQ ID NO: 82) and rat β-CGRP (SEQ ID NO: 83) with detectable affinity, such as an affinity measured by a $K_D$ of about 200 nM or lower, such as about 150 nM or lower, for example, when measured in a competition ELISA assay essentially described in Example 4.

In another aspect, the current disclosure provides an hNGAL mutein that may be further capable of binding rat CGRP with a $K_D$ of about 5 nM or lower, for example, when measured by a SPR based assay essentially described in Example 5.

In some still further embodiments, an hNGAL mutein of the disclosure may be further capable of inhibiting or reducing rat CGRP induced cAMP production with an IC50 value of about 5 nM or lower, such as about 0.2 nM or lower, in a L6 cell-based functional assay essentially described in Example 6.

In some embodiments, an hNGAL mutein of this disclosure may be further crossreactive with both human CGRP and rat CGRP.

In some other embodiments, an hNGAL mutein of this disclosure may be further crossreactive with both human α-CGRP and human β-CGRP.

In some other embodiments, an hNGAL mutein of this disclosure may be further crossreactive with both rat α-CGRP and rat β-CGRP.

In this regard, the disclosure relates to one or more hNGAL muteins, wherein said hNGAL muteins in comparison with the linear polypeptide sequence of the mature hNGAL, may further comprise at least 1, 2, 3, 4, 5, 6, 7, 8, 9, 10, 11, 12, 13, 14, 15, 16, 17, 18, 19, 20, 21, or even more, a mutated amino acid residue at one or more positions corresponding to the sequence positions 8, 9, 28, 36, 38, 40, 41, 42, 44, 46, 47, 49, 52, 54, 62, 65, 66, 68, 70, 71, 72, 73, 75, 76, 77, 79, 80, 81, 83, 87, 96, 97, 98, 100, 103, 105, 106, 108, 111, 112, 114, 123, 125, 126, 127, 129, 132, 134, 135, 136, 145, 146, 175, 176, 177 and 178 of the linear polypeptide sequence of the mature hNGAL (SEQ ID NO: 1), and wherein said hNGAL muteins bind CGRP with detectable affinity.

In some embodiments, an hNGAL mutein of the disclosure may further comprise a mutated amino acid residue at any one or more positions corresponding to the sequence positions 36, 40, 41, 49, 52, 68, 70, 72, 73, 77, 79, 81, 96, 100, 103, 106, 125, 127, 132 and 134 of the linear polypeptide sequence of the mature hNGAL (SEQ ID NO: 1).

In some embodiments, an hNGAL mutein of the disclosure may further comprise at least one of the following mutated amino acid residue in comparison with the linear polypeptide sequence of the mature hNGAL: Leu 36→Ile, Phe, Trp, Arg or Glu; Ala 40→Met, Trp or Thr; Ile 41→Leu, Trp, Gly or Glu; Gln 49→Leu, Phe, Lys, Glu or Thr; Tyr 52→Ala, Gly, Glu or Gln; Ser 68→Trp, His or Asp; Leu 70→Met, Trp, Tyr, Gly or Gln; Arg 72→Met, Ile, Trp, Glu or Ser; Lys 73→Ala, Glu, Thr or Gln; Asp 77→Ile or Asn; Trp 79→Val, Gly, His or Thr; Arg 81→Gly, His, Glu or Asn; Asn 96→Ala, Gly or Thr; Tyr 100→Ile, Pro or Glu; Leu 103→Met, Glu, Thr or Gln; Tyr 106→Leu, Ile, Ala, His or Asn; Lys 125 Val, Phe, Gly or Glu; Ser 127→Phe, Trp or Arg; Tyr 132→Leu, Ile or Trp; Lys 134→Trp, His or Glu.

In some embodiments, an hNGAL mutein of the disclosure may further comprise two or more, such as 3, 4, 5, 6, 7, 8, 9, 10, 11, 12, 13, 14, 15, 16, or even more or all mutated amino acid residues at these sequence positions of the mature hNGAL.

Additionally, an hNGAL mutein according to the disclosure may also comprise the following substitution in comparison with the linear polypeptide sequence of the mature hNGAL: Gln 28→His and Cys 87→Ser.

In some additional embodiments, an hNGAL mutein of the disclosure, which binds to CGRP, may further comprise one of the following sets of amino acid substitutions in comparison with the linear polypeptide sequence of the mature hNGAL:

(a) Gln 28→His; Leu 36→Glu; Ala 40→Trp; Ile 41→Gly; Gln 49→Lys; Tyr 52→Ala; Ser 68→Asp; Leu 70→Gln; Arg 72→Ile; Lys 73→Glu; Arg 81→Gly; Cys 87→Ser; Asn 96→Ala; Tyr 100→Glu; Leu 103→Gln; Tyr 106→Asn; Lys 125→Glu; Ser 127→Trp; Tyr 132→Leu; Lys 134→Trp;

(b) Gln 28→His; Leu 36→Phe; Ala 40→Met; Ile 41→Trp; Gln 49→Phe; Tyr 52→Gly; Ser 68→Trp; Leu 70→Trp; Arg 72→Glu; Lys 73→Ala; Trp 79→Gly; Arg 81→Asn; Cys 87→Ser; Asn 96→Gly; Tyr 100→Pro; Leu 103→Met; Tyr 106→His; Lys 125→Glu; Ser 127→Phe; Tyr 132→Trp; Lys 134→Trp;

(c) Gln 28→His; Leu 36→Trp; Ala 40→Thr; Ile 41→Leu; Gln 49→Thr; Tyr 52→Gln; Ser 68→Trp; Leu 70→Tyr; Arg 72→Ser; Lys 73→Glu; Asp 77→) Asn; Trp 79→His; Arg 81→Glu; Cys 87→Ser; Asn 96→Thr; Leu 103→Glu; Tyr 106→Ile; Lys 125→Gly; Tyr 132→Ile; Lys 134→Glu;

(d) Gln 28→His; Leu 36→Arg; Ile 41→Glu; Gln 49→Glu; Tyr 52→Glu; Ser 68→Asp; Leu 70→Gly; Arg 72→Trp; Lys 73→Gln; Asp 77→Ile; Trp 79→Val; Arg 81→His; Cys 87→Ser; Leu 103→Thr; Tyr 106→Ala; Lys 125→Val; Ser 127→Arg; Tyr 132→Trp; Lys 134→Glu; or (e) Gln 28→His; Leu 36→Ile; Ala 40→Trp; Ile 41→Trp; Gln 49→Leu; Ser 68→His; Leu 70→Met; Arg 72→Met; Lys 73→Thr; Trp 79→Thr; Cys 87→Ser; Tyr 100→Ile; Leu 103→Met; Tyr 106→Leu; Lys 125→Phe; Ser 127→Trp; Tyr 132→Trp; Lys 134→His.

Moreover, an hNGAL mutein according to the disclosure may further comprise the following substitution in comparison with the linear polypeptide sequence of the mature hNGAL: Gln 28→His; Leu 36→Trp; Ala 40→Thr; Ile 41→Leu; Leu 42→Arg; Asp 47→Asn; Gln 49→Ile, Pro or Thr; Tyr 52-4 Gln; Thr 54→Met, Ile or Lys; Lys 62→Arg; Asn 65→Asp; Val 66→Ala; Ser 68→Trp; Leu 70→Tyr; Phe 71→Leu; Arg 72→Ala or Ser; Lys 73→Asp or Glu; Lys 75→Arg; Asp 77→Arg or Asn; Trp 79→His; Arg 81→Glu; Phe 83→Ser; Cys 87→Ser; Asn 96→Leu or Thr; Ile 97→Thr; Lys 98-4 Gln; Tyr 100→His; Leu 103→Glu; Ser 105→Pro; Tyr 106→Ile; Val 111→Met; Lys 125→Gly; Val 126→Met; Ser 127→Gly or Asn; Tyr 132→Ile; Lys 134→Glu; Thr 136→Ile or Val; Thr 145→Ala and Ser 146→Asn.

In some particular embodiments, an hNGAL mutein of the disclosure, which binds to CGRP, may further comprise one of the following sets of amino acid substitutions in comparison with the linear polypeptide sequence of the mature hNGAL:

(a) Gln 28→His; Leu 36→Trp; Ala 40→Thr; Ile 41→Leu; Gln 49→Ile; Tyr 52→Gln; Ser 68→Trp; Leu 70→Tyr; Arg 72→Ser; Lys 73→Glu; Lys 75→Arg; Asp 77→Asn; Trp 79→His; Arg 81→Glu; Phe 83→Ser; Cys 87→Ser; Asn 96→Thr; Leu 103→Glu; Tyr 106→Ile; Lys 125→Gly; Tyr 132→Ile; Lys 134→Glu;

(b) Gln 28→His; Leu 36→Trp; Ala 40→Thr; Ile 41→Leu; Leu 42→Arg; Asp 47→Asn; Gln 49→Thr; Tyr 52→Gln; Ser 68→Trp; Leu 70→Tyr; Arg 72→Ser; Lys 73→Glu; Asp 77→Asn; Trp 79→His; Arg 81→Glu; Phe 83→Ser; Cys 87→Ser; Asn 96→Thr; Leu 103→Glu; Tyr 106→Ile; Lys 125→Gly; Tyr 132→Ile; Lys 134→Glu;

(c) Gln 28→His; Leu 36→Trp; Ala 40→Thr; Ile 41→Leu; Gln 49→Ile; Tyr 52→Gln; Asn 65→Asp; Ser 68→Trp; Leu 70→Tyr; Phe 71→Leu; Arg 72→Ser; Lys 73→Glu; Asp 77→Asn; Trp 79→His; Arg 81→Glu; Phe 83→Ser; Cys 87→Ser; Asn 96→Thr; Leu 103→Glu; Tyr 106→Ile; Lys 125→Gly; Val 126→Met; Tyr 132→Ile; Lys 134→Glu; Thr 145→Ala;

(d) Gln 28→His; Leu 36→Trp; Ala 40→Thr; Ile 41→Leu; Asp 47→Asn; Gln 49→Thr; Tyr 52→Gln; Val 66→Ala; Ser 68→Trp; Leu 70→Tyr; Phe 71→Leu; Arg 72→Ser; Lys 73→Glu; Asp 77→Asn; Trp 79→His; Arg 81→Glu; Phe 83→Ser; Cys 87→Ser; Asn 96→Thr; Ile 97→Thr; Leu 103→Glu; Ser 105→Pro; Tyr 106→Ile; Lys 125→Gly; Tyr 132→Ile; Lys 134→Glu;

(e) Gln 28→His; Leu 36→Trp; Ala 40→Thr; Ile 41→Leu; Gln 49→Ile; Tyr 52→Gln; Thr 54→Ile; Lys 62→Arg; Ser 68→Trp; Leu 70→Tyr; Arg 72→Ser; Lys 73→Glu; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(f) Gln 28→His; Leu 36→Trp; Ala 40→Thr; Ile 41→Leu; Gln 49→Pro; Tyr 52→Gln; Lys 62→Arg; Ser 68→Trp; Leu 70→Tyr; Arg 72→Ser; Lys 73→Glu; Asp 77→Asn; Trp 79→His; Arg 81→Glu; Phe 83→Ser; Cys 87→Ser; Asn 96→Thr; Lys 98→Gln; Tyr 100→His; Leu 103→Glu; Ser 105→Pro; Tyr 106→Ile; Lys 125→Gly; Val 126→Met; Ser 127→Gly; Tyr 132→Ile; Lys 134→Glu;

(g) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Asp; Asp 77→Asn; Trp 79→His; Arg 81→Glu; Cys 87→Ser; Asn 96→Leu; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(h) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala;

Lys 73→Glu; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(i) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Asp; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(j) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Asp; Asp 77→Arg; Trp 79→His; Arg 81→Glu; Cys 87→Ser; Asn 96→Thr; Tyr 100→His; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(k) Gln 28→His; Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; or (l) Gln 28→His; Leu 36→Trp; Ala 40→Thr; Ile 41→Leu; Gln 49→Ile; Tyr 52→Gln; Thr 54→Ile; Lys 62→Arg; Ser 68→Trp; Leu 70→Tyr; Arg 72→Ser; Lys 73→Glu; Asp 77→Asn; Trp 79→His; Arg 81→Glu; Cys 87→Ser; Asn 96→Thr; Leu 103→Glu; Ser 105→Pro; Tyr 106→Ile; Val 111→Met; Lys 125→Gly; Ser 127→Asn; Tyr 132→Ile; Lys 134→Glu; Thr 136→Ile; Ser 146→Asn.

Additionally, an hNGAL mutein according to the disclosure may also comprise the following substitution in comparison with the linear polypeptide sequence of the mature hNGAL: Cys 76→Leu, Met, Val, Ile, Phe, Arg, Lys or Asn and Cys 175→Leu, Val, Phe, Trp, Tyr, Asp or Glu.

In some particular embodiments, an hNGAL mutein of the disclosure, which binds to CGRP, may further comprise one of the following sets of amino acid substitutions in comparison with the linear polypeptide sequence of the mature hNGAL:

(a) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Arg; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Phe;

(b) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Met; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Tyr;

(c) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Leu; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Trp;

(d) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Ile; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Glu;

(e) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Val; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Tyr;

(f) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Arg; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Trp;

(g) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Asn; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Leu;

(h) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Arg; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Val;

(i) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Lys; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Asp; or (j) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Phe; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Asp.

In addition, an hNGAL mutein according to the disclosure may further comprise the following substitution in comparison with the linear polypeptide sequence of the mature hNGAL: Gln 28→His; Leu 36→Arg; Gly 38→Ala; Ala 40→Asp or Glu; Ile 41→Val, Thr, Ala, Arg or Glu; Glu 44→Lys or Asp; Lys 46→Asn; Gln 49→Glu; Tyr 52→Glu; Ser 68→Asp; Leu 70→Gly; Phe 71→Leu; Arg 72→Val or Ser; Lys 73→Arg, Glu or Gln; Lys 75→Arg; Asp 77→Met or Ile; Trp 79→Val; Ile 80→Val or Thr; Arg 81→His; Cys 87→Ser or Gly; Lys 98→Glu; Leu 103→Val or Thr; Tyr 106→Ala or Gly; Val 108→Ile; Ser 112→Asn; Asn 114→Asp; Phe 123→Val; Lys 125→Leu or Val; Ser 127→Gly, Arg or Lys; Asn 129→Ser; Tyr 132→Leu or Ser; Lys 134→Glu and Ile 135→Val.

In some particular embodiments, an hNGAL mutein of the disclosure, which binds to CGRP, may further comprise one of the following sets of amino acid substitutions in comparison with the linear polypeptide sequence of the mature hNGAL:

(a) Gln 28→His; Leu 36→Arg; Ala 40→Glu; Ile 41→Glu; Tyr 52→Glu; Ser 68→Asp; Leu 70→Gly; Arg 72→Ser; Lys 73→Glu; Asp 77→Ile; Trp 79→Val; Arg 81→His; Cys 87→Ser; Leu 103→Val; Tyr 106→Ala; Lys 125→Val; Ser 127→Lys; Tyr 132→Leu; Lys 134→Glu;

(b) Gln 28→His; Leu 36→Arg; Ala 40→Asp; Ile 41→Ala; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Ala; Lys 125→Leu; Ser 127→Lys; Tyr 132→Leu; Lys 134→Glu;

(c) Gln 28→His; Leu 36→Arg; Gly 38→Ala; Ala 40→Asp; Ile 41→Arg; Gln 49→Glu; Tyr 52→Glu; Ser 68→Asp; Leu 70→Gly; Arg 72→Ser; Lys 73→Arg; Asp 77→Ile; Trp 79→Val; Arg 81→His; Cys 87→Ser; Leu 103→Thr; Tyr 106→Gly; Lys 125→Val; Ser 127→Gly; Tyr 132→Ser; Lys 134→Glu;

(d) Gln 28→His; Leu 36→Arg; Ala 40→Asp; Ile 41→Glu; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Gly; Lys 125→Val; Ser 127→Arg; Tyr 132→Leu; Lys 134→Glu;

(e) Gln 28→His; Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu;

(f) Gln 28→His; Leu 36→Arg; Gly 38→Ala; Ala 40→Asp; Ile 41→Val; Glu 44→Asp; Lys 46→Asn; Gln 49→Glu; Tyr 52→Glu; Ser 68→Asp; Leu 70→Gly; Arg 72→Val; Lys 73→Gln; Asp 77→Met; Trp 79→Val; Ile 80→Val; Arg 81→His; Cys 87→Ser; Leu 103→Val; Tyr 106→Ala; Lys 125→Leu; Ser 127→Lys; Tyr 132→Leu; Lys 134→Glu; Ile 135→Val;

(g) Gln 28→His; Leu 36→Arg; Ala 40→Asp; Ile 41→Thr; Gln 49→Glu; Tyr 52→Glu; Ser 68→Asp; Leu 70→Gly; Phe 71→Leu; Arg 72→Val; Lys 73→Gln; Asp 77→Met; Trp 79→Val; Arg 81→His; Cys 87→Ser; Leu 103→Val; Tyr 106→Ala; Phe 123→Val; Lys 125→Leu; Ser 127→Lys; Asn 129→Ser; Tyr 132→Leu; Lys 134→Glu;

(h) Gln 28→His; Leu 36→Arg; Ala 40→Asp; Ile 41→Thr; Glu 44→Lys; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Ala; Phe 123→Val; Lys 125→Leu; Ser 127→Lys; Tyr 132→Leu; Lys 134→Glu;

(i) Gln 28→His; Leu 36→Arg; Ala 40→Asp; Ile 41→Ala; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Ala; Val 108→Ile; Ser 112→Asn; Phe 123→Val; Lys 125→Leu; Ser 127→Lys; Tyr 132→Leu; Lys 134→Glu; or (j) Gln 28→His; Leu 36→Arg; Ala 40→Asp; Ile 41→Ala; Gln 49→Glu; Tyr 52→Glu; Ser 68→Asp; Leu 70→Gly; Phe 71→Leu; Arg 72→Val; Lys 73→Gln; Asp 77→Met; Trp 79→Val; Arg 81→His; Cys 87→Gly; Leu 103→Val; Tyr 106→Ala; Phe 123→Val; Lys 125→Leu; Ser 127→Lys; Tyr 132→Leu; Lys 134→Glu.

Additionally, an hNGAL mutein according to the disclosure may also comprise the following substitution in comparison with the linear polypeptide sequence of the mature hNGAL: Cys 76→Leu or Tyr; Cys 175→Ile; Ile 176→Asp and Asp 177→Gly.

In some particular embodiments, an hNGAL mutein of the disclosure, which binds to CGRP, may further comprise one of the following sets of amino acid substitutions in comparison with the linear polypeptide sequence of the mature hNGAL:

(a) Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Cys 76→Leu; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Cys 175→Ile; Ile 176→Asp; Asp 177→Gly; or (b) Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Cys 76→Tyr; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Cys 175→Ile; Ile 176→Asp; Asp 177→Gly.

In addition, an hNGAL mutein according to the disclosure may further comprise the following substitution and addition in comparison with the linear polypeptide sequence of the mature hNGAL: Ile 8→Lys; Pro 9→His; Gln 28→His; Leu 36→Trp or Arg; Ala 40→Thr or Asp; Ile 41→Leu or Val; Gln 49→Ile or Glu; Tyr 52→Gln or Glu; Thr 54→Met; Asn 65→Gln; Ser 68→Trp or Asp; Leu 70→Tyr or Gly; Arg 72→Ala or Val; Lys 73→Asp or Gln; Lys 75→Arg; Cys 76→Ile; Asp 77→Asn or Met; Trp 79→His or Val; Ile 80→Thr; Arg 81→Glu or His; Cys 87→Ser; Asn 96→Thr; Lys 98→Glu; Leu 103→Glu or Val; Ser 105→Pro; Tyr 106→Ile or Ala; Asn 114→Asp; Phe 123→Val; Lys 125→Gly or Leu; Ser 127→Asn or Lys; Tyr 132→Ile or Leu; Lys 134→Glu; Thr 136→Val; Ser 146→Asn; Cys 175→Glu; Gly 178→Asp and Gly is added to N-terminal amino acid (Gln 1).

In some particular embodiments, an hNGAL mutein of the disclosure, which binds to CGRP, may further comprise one of the following sets of amino acid substitutions and additions in comparison with the linear polypeptide sequence of the mature hNGAL:

(a) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Ile; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile;

Lys 134→Glu; Thr 136→Val; Ser 146→Asn; Cys 175→Glu and Gly is added to N-terminal amino acid (Gln 1) (SEQ ID NO: 87);

(b) Gln 28→His; Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu and Gly is added to N-terminal amino acid (Gln 1) (SEQ ID NO: 88);

(c) Gln 28→His; Leu 36→Arg; Ala 40→Asp; Ile 41→Val; Gln 49→Glu; Tyr 52→Glu; Asn 65→Gln; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Gly 178→Asp and Gly is added to N-terminal amino acid (Gln 1) (SEQ ID NO: 89);

(d) Ile 8→Lys; Gln 28→His; Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu and Gly is added to N-terminal amino acid (Gln 1) (SEQ ID NO: 90);

(e) Pro 9→His; Gln 28→His, Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu and Gly is added to N-terminal amino acid (Gln 1) (SEQ ID NO: 91);

(f) Ile 8→Lys; Gln 28→His; Leu 36→Arg; Ala 40→Asp; Ile 41→Val; Gln 49→Glu; Tyr 52→Glu; Asn 65→Gln; Ser 68→Asp; Leu 70→Gly; Arg 72→Val; Lys 73 Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Gly 178→Asp and Gly is added to N-terminal amino acid (Gln 1) (SEQ ID NO: 92); or (g) Pro 9→His; Gln 28→His; Leu 36→Arg; Ala 40→Asp; Ile 41→Val; Gln 49→Glu; Tyr 52→Glu; Asn 65→Gln; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Gly 178→Asp and Gly is added to N-terminal amino acid (Gln 1) (SEQ ID NO: 93).

In the residual region, i.e. the region differing from sequence positions 8, 9, 28, 36, 38, 40, 41, 42, 44, 46, 47, 49, 52, 54, 62, 65, 66, 68, 70, 71, 72, 73, 75, 76, 77, 79, 80, 81, 83, 87, 96, 97, 98, 100, 103, 105, 106, 108, 111, 112, 114, 123, 125, 126, 127, 129, 132, 134, 135, 136, 145, 146, 175, 176, 177 and 178, an hNGAL mutein of the disclosure may include the wild type (natural) amino acid sequence outside the mutated amino acid sequence positions.

In further particular embodiments, a mutein according to the current disclosure comprises an amino acid sequence selected from the group consisting of SEQ ID NOs: 2-40, 87-93 or a functional fragment or variant thereof. In some embodiments, such fragment or variant is a structural homologue of a mutein defined in any one of SEQ ID NOs: 2-40, 87-93.

The amino acid sequence of an hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 2-40, 87-93.

In some still embodiments, an hNGAL mutein is cross-reactive with or binding to human CGRP and/or rat CGRP according to the disclosure comprises an amino acid sequence selected from the group consisting of SEQ ID NOs: 2-40, 87-93 and functional fragments or variants thereof.

The disclosure also includes structural homologues of an hNGAL mutein comprising an amino acid sequence selected from the group consisting of SEQ ID NOs: 2-40, 87-93, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein and bind to CGRP.

An hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to CGRP, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188, SEQ ID NO: 1).

The present disclosure also relates to a pharmaceutical composition that includes at least one hNGAL mutein disclosed herein, or conjugate or fusion protein thereof as described herein, and a pharmaceutically acceptable excipient.

Accordingly, the hNGAL muteins of the disclosure can be formulated into compositions using pharmaceutically acceptable ingredients as well as established methods of preparation (Gennaro and Gennaro (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used.

B. Applications of Muteins Specific for CGRP

Recently, Arulmozhi and colleagues have reported, various theories on migraines (Vascular Pharmacology 43; 176-187, 2005). One of the theories proposes that the currently unknown triggers of migraine stimulate trigeminal nerves and ganglia that innervate cephalic tissue, giving rise to release of neuropeptide messenger molecules from axons on the vasculature. Release of these neuropeptides then activates a series of events, a consequence of which is migraine pain. In addition, release of these neuropeptides changes vascular permeability resulting in subsequent leakage of plasma proteins in tissues innervated by stimulated trigeminal fibers. This leakage results in neurogenic inflammation which leads to migraines.

Of these neuropeptides, CGRP has been reported to play a role in migraines as CGRP is released upon stimulation of sensory nerves and has potent vasodilatory activity. (Vascular Pharmacology 43; 176-187, 2005). Further, the release of CGRP increases vascular permeability and subsequent plasma protein leakage (plasma protein extravasation) in tissues innervated by trigeminal nerve fibers upon stimulation of these fibers. (Vascular Pharmacology 43; 176-187, 2005). In addition, studies have reported that infusion of CGRP in patients who suffer from migraines has resulted in migraine-like symptoms. (Cephalagia 22(1): 54-61, 2002).

Historically, small molecule agonists of serotonin 5-HT1B and 5-HT1D receptors have been used as treatments for migraines. These so-called triptans are potent vasoconstrictors and have been shown to inhibit plasma protein extravasation due to stimulation of trigeminal nerve fibers in an experimental animal migraine model. In addition, doses of a triptan that decreased plasma protein extravasation also attenuated CGRP levels in the same experimental animal model. (Br. J. Pharmacology 99; 202-206, 1990; Neuropharmacology 30(11): 1193-1200, 1991).

Although triptans have been found to be efficacious, many patients who respond to triptan treatment suffer from recurrent headaches within several hours after treatment. Further, since triptans are potent vasoconstrictors, they are contraindicated in certain patient populations, such as populations of patients suffering from hypertension or suffering from ischemic heart disease. There is therefore a need for therapeutic compounds to prevent and/or treat migraines without unwanted side effects such as cardiovascular-related effects.

Numerous possible applications for the muteins with binding-affinity for CGRP of the disclosure, therefore, exist in medicine, for example, in migraine, temporomandibular joint disorder as well as a variety of other diseases such as cardiac failure, hypertension, and sepsis. In one further aspect, the disclosure relates to the use of such a mutein disclosed herein for detecting CGRP in a sample as well as a respective method of diagnosis.

The present disclosure also involves the use of one or more muteins with binding-affinity for CGRP as described for complex formation with CGRP.

Therefore, in another aspect of the disclosure, the disclosed muteins are used for the detection of CGRP. Such use may include the steps of contacting one or more said muteins, under suitable conditions, with a sample suspected of containing CGRP, thereby allowing formation of a complex between the muteins and CGRP, and detecting the complex by a suitable signal.

The detectable signal can be caused by a label, as explained above, or by a change of physical properties due to the binding, i.e. the complex formation, itself. One example is SPR, the value of which is changed during binding of binding partners from which one is immobilized on a surface such as a gold foil.

The muteins disclosed herein may also be used for the separation of CGR. Such use may include the steps of contacting one or more said muteins, under suitable conditions, with a sample supposed to contain CGRP, thereby allowing formation of a complex between the muteins and CGRP, and separating the complex from the sample.

In the use of the disclosed muteins for the detection of CGRP as well as the separation of CGRP, the muteins and/or CGRP or a domain or fragment thereof may be immobilized on a suitable solid phase.

Accordingly, the presence or absence of a molecule such as CGRP, e.g., in a sample, as well as its concentration or level may be determined.

The muteins of the present disclosure, therefore, may be used to detect and/or measure CGRP in a sample, e.g., for diagnostic purposes. For example, the muteins may be used to diagnose a condition or disease characterized by aberrant expression (e.g., over-expression, under-expression, lack of expression, etc.) of CGRP. Exemplary diagnostic assays for CGRP may comprise, e.g., contacting a sample, obtained from a patient, with the muteins, wherein the muteins are labeled with a detectable label or reporter molecule. Alternatively, unlabeled the muteins can be used in diagnostic applications in combination with a secondary molecule which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure CGRP in a sample include enzyme-linked immunosorbent assay (ELISA), radioimmunoassay (RIA), and fluorescence-activated cell sorting (FACS).

In still another aspect, the present disclosure features a diagnostic or analytical kit comprising a mutein with binding-affinity for CGRP according to the disclosure.

In a further aspect, the disclosure also encompasses the use of disclosed hNGAL muteins or combinations comprising such muteins described herein for the manufacture of a pharmaceutical composition. The pharmaceutical composition thus obtained may be suited to decrease circulating levels of free CGRP which is useful for the treatment or prevention of migraines in subjects, preferably humans. The pharmaceutical composition may be used as monotherapy or as combination therapy. Accordingly, the disclosure also provides hNGAL muteins for the treatment of a disease or disorder associated with deregulated protein plasma extravasation.

In addition to their use in diagnostics, in yet another aspect, the disclosure encompasses the use of such a mutein of the disclosure or a composition or a combination comprising such mutein for the binding of CGRP in a subject and/or reducing the amount of protein extravasation in a subject. In some embodiments, such subject may suffer from diseases or disorders caused by a release of neuropeptides, which changes vascular permeability resulting in subsequent leakage of plasma proteins in tissues innervated by stimulated trigeminal fibers.

In still another aspect, the present disclosure features a method of binding CGRP in a subject, comprising administering to said subject an effective amount of one or more muteins with binding-affinity for CGRP of the disclosure or of one or more compositions or combinations comprising such the mutein.

In still another aspect, the present disclosure involves a method for inhibiting or reducing migraines in a subject, comprising administering to said subject an effective amount of one or more muteins of the disclosure with binding-affinity for CGRP or fragments of CGRP or of one or more compositions or combinations comprising such muteins. In some embodiments, such subject may suffer from diseases or disorders associated with deregulated levels of free CGRP.

The muteins of the disclosure or compositions or combinations comprising such muteins are useful, inter alia, for the treatment, prevention and/or amelioration of any disease or disorder associated with CGRP activity, including diseases or disorders associated with deregulated levels of free CGRP.

In still another aspect, the present disclosure involves a method for inhibiting or reducing plasma protein extravasation in a subject, comprising administering to said subject an effective amount of one or more muteins of the disclosure with binding-affinity for CGRP or fragments of CGRP or of one or more compositions or combinations comprising such muteins.

For example, the muteins or compositions or combinations comprising such muteins of the disclosure may be used to decrease circulating levels of free CGRP.

In some other embodiments, the muteins or compositions or combinations comprising such muteins of the present disclosure may also be useful for the treatment, prevention and/or amelioration of migraines.

The hNGAL muteins according to the disclosure or compositions or combinations comprising such muteins can be administered via any parenteral or non-parenteral (e.g. enteral) route that is therapeutically effective. A therapeutically effective route provides for delivery of an agent to a desired compartment, system, or location. For example, a therapeutically effective route is one through which an agent can be administered to provide at the desired site of action an amount of the agent sufficient to effectuate a beneficial or desired clinical result.

C. Muteins of the Disclosure

When used herein in the context of the muteins of the present disclosure that bind to CGRP, the term "specific for" includes that the mutein is directed against, binds to, or reacts with CGRP. Thus, being directed to, binding to or reacting with includes that the mutein specifically binds to CGRP. The term "specifically" in this context means that the mutein reacts with a CGRP, as described herein, but essentially not with another target. Whether the mutein specifically reacts as defined herein above can easily be tested, inter alia, by comparing the reaction of a hNGAL mutein of the present disclosure with CGRP and the reaction of said mutein with (an) other target(s). "Specific binding" can also be determined, for example, in accordance with Western blots, ELISA-, RIA-, ECL-, IRMA-tests, FACS, IHC and peptide scans.

The amino acid sequence of a mutein according to the disclosure has a high sequence identity to human lipocalin 2 when compared to sequence identities with another lipocalin (see also above). In this general context the amino acid sequence of a mutein of the combination according to the disclosure is at least substantially similar to the amino acid sequence of the corresponding lipocalin (the wild-type hNGAL). A respective sequence of a mutein of the combination according to the disclosure, being substantially similar to the sequence of mature hNGAL, such as at least 65%, at least 70%, at least 75%, at least 80%, at least 82%, at least 85%, at least 87%, at least 90% identity, including at least 95% identity to the sequence of mature hNGAL. In this regard, a mutein of the disclosure of course may contain, in comparison substitutions as described herein which renders the mutein capable of binding to CGRP. Typically a mutein of hNGAL includes one or more mutations—relative to the native sequence of hNGAL—of amino acids in the four loops at the open end of the ligand binding site of hNGAL. As explained above, these regions are essential in determining the binding specificity of a mutein for CGRP. A mutein derived hNGAL or a homologue thereof, may have one, two, three, four or more mutated amino acid residues at any sequence position in the N-terminal region and/or in the three peptide loops BC, DE, and FG arranged at the end of the β-barrel structure that is located opposite to the natural binding pocket. In some particular embodiments, an hNGAL mutein according to the present disclosure comprises four loops of one of SEQ ID NOs: 2-40, 87-93 which together define a binding pocket for CGRP.

A mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native hNGAL, provided that such a mutein should be capable of binding to CGRP. For example, a mutein can have a substitution at a position corresponding to a distinct position (i.e. at a corresponding position) of hNGAL. In some embodiments a mutein of the combination according to the disclosure includes at least two amino acid substitutions, including 2, 3, 4, 5, or even more, amino acid substitutions of a native amino acid by an arginine residue. Accordingly, the nucleic acid of a protein 'reference' scaffold as described herein is subject to mutagenesis with the aim of generating a mutein which is capable of binding to CGRP.

Also, a mutein of the present disclosure can comprise a heterologous amino acid sequence at its N- or C-terminus, preferably C-terminus, such as a Strep-tag, e.g., Strep II tag without affecting the biological activity (binding to its target e.g. CGRP) of the mutein.

Specifically, in order to determine whether an amino acid residue of the amino acid sequence of a mutein different from wild-type hNGAL corresponds to a certain position in the amino acid sequence of wild-type hNGAL, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, wild-type hNGAL can serve as "subject sequence" or "reference sequence", while the amino acid sequence of a mutein different from the wild-type hNGAL described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the mutein retains its capability to bind CGRP, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

a. Alanine (Ala), Glycine (Gly);
b. Aspartic acid (Asp), Glutamic acid (Glu);
c. Asparagine (Asn), Glutamine (Gln);
d. Arginine (Arg), Lysine (Lys);
e. Isoleucine (Ile), Leucine (Leu), Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of hNGAL are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: aspartic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of hNGAL also may be substituted, generally with serine, to improve the oxidative stability of the molecule and prevent aberrant crosslinking. Conversely, cysteine bond (s) may be added to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of hNGAL as long as these deletions or insertion result in a stable folded/functional mutein.

Modifications of the amino acid sequence include directed mutagenesis of single amino acid positions in order to simplify sub-cloning of the mutated hNGAL gene or its parts by incorporating cleavage sites for certain restriction enzymes. In addition, these mutations can also be incorporated to further improve the affinity of a mutein for a given target such as CGRP. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective mutein.

It is also possible to mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages.

In some embodiments, if one of the above moieties is conjugated to a mutein of the disclosure, conjugation to an amino acid side chain can be advantageous. Suitable amino acid side chains may occur naturally in the amino acid sequence of hNGAL or may be introduced by mutagenesis. In case a suitable binding site is introduced via mutagenesis, one possibility is the replacement of an amino acid at the appropriate position by a cysteine residue.

With respect to a mutein of human lipocalin 2, exemplary possibilities of such a mutation to introduce a cysteine residue into the amino acid sequence of a lipocalin including human lipocalin 2 mutein to include the introduction of a cysteine (Cys) residue at least at one of the sequence positions that correspond to sequence positions 14, 21, 60, 84, 88, 116, 141, 145, 143, 146 or 158 of the wild type sequence of human NGAL. In some embodiments where a human lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No. P80188 (SEQ ID NO: 1). The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human lipocalin 2 mutein.

In another embodiment, in order to provide suitable amino acid side chains for conjugating one of the above compounds to a mutein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

In some embodiments, a mutein of the disclosure may be fused at its N-terminus or its C-terminus to a protein, a protein domain or a peptide, for instance, a signal sequence and/or an affinity tag.

Affinity tags such as the Strep-Tag® or Strep-Tag® II (Schmidt, T. G. M. et al. (1996) *J. Mol. Biol* 255, 753-766), the myc-tag, the FLAG-tag, the $His_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for muteins of the disclosure as well.

In general, it is possible to label the muteins of the disclosure with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the disclosure. The muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The muteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a mutein of the disclosure may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a mutein with binding activity for albumin. Accordingly, suitable conjugation partners for extending the half-life of a mutein of the disclosure include an albumin binding protein, for example, a bacterial albumin binding domain, such as the one of streptococcal protein G (König, T., & Skerra, A. (1998) *J. Immunol. Methods* 218, 73-83). Other examples of albumin binding peptides that can be used as conjugation partner are, for instance, those comprising a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in U.S. Patent Application 2003/0069395 (incorporated herein by reference in its entirety) or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself (Osborn, B. L. et al., 2002, *J. Pharmacol. Exp. Ther.* 303, 540-548), or a biological active fragment of albumin can be used as conjugation partner of a mutein of the disclosure. The term "albumin" includes all mammal albumins such as human serum albumin or bovine serum albumin or rat albumin. The albumin or fragment thereof can be recombinantly produced as described in U.S. Pat. No. 5,728,553 or European Patent Applications EP 0 330 451 and EP 0 361 991 (incorporated herein by reference in their entirety). Recombinant human albumin (Recombumin®) Novozymes Delta Ltd. (Nottingham, UK) can be conjugated or fused to a mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the disclosure, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the muteins of the disclosure is to fuse to the N- or C-terminus of the muteins long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the disclosure for the purpose of serum half-life extension.

In addition, a mutein disclosed herein may be fused to a moiety may confer new characteristics to the muteins of the disclosure such as enzymatic activity or binding affinity for other molecules. Examples of suitable fusion partners are alkaline phosphatase, horseradish peroxidase, gluthation-S-transferase, the albumin-binding domain of protein G, protein A, antibody fragments, oligomerization domains or toxins.

In particular, it may be possible to fuse a mutein disclosed herein with a separate enzyme active site such that both "components" of the resulting fusion protein together act on a given therapeutic target. The binding domain of the mutein attaches to the disease-causing target, allowing the enzyme domain to abolish the biological function of the target.

The present disclosure also relates to nucleic acid molecules (DNA and RNA) that include nucleotide sequences encoding the muteins of the disclosure. Since the degeneracy of the genetic code permits substitutions of certain codons by other codons specifying the same amino acid, the disclosure is not limited to a specific nucleic acid molecule encoding a mutein as described herein but encompasses all nucleic acid molecules that include nucleotide sequences encoding a functional mutein. In this regard, the present disclosure provides nucleotide sequences, as shown in SEQ ID NOs: 41-79, 94-100, encoding some muteins of the disclosure.

In one embodiment of the disclosure, the method includes subjecting the nucleic acid molecule to mutagenesis at nucleotide triplets coding for at least one, or even more amino acids, of the sequence positions corresponding to the sequence positions 8, 9, 28, 36, 38, 40, 41, 42, 44, 46, 47, 49, 52, 54, 62, 65, 66, 68, 70, 71, 72, 73, 75, 76, 77, 79, 80, 81, 83, 87, 96, 97, 98, 100, 103, 105, 106, 108, 111, 112, 114, 123, 125, 126, 127, 129, 132, 134, 135, 136, 145, 146, 175, 176, 177 and 178 of the linear polypeptide sequence of human NGAL (SEQ ID NO: 1).

The disclosure also includes nucleic acid molecules encoding the muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a mutein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g., HeLa cells or CHO cells) or primary mammalian cells.

The disclosure also relates to a method for the production of a mutein as described herein, wherein the mutein or polypeptide, a fragment of the mutein or a fusion protein of the mutein is produced starting from the nucleic acid coding for the mutein or polypeptide by means of genetic engineering methods. The method can be carried out in vivo, the mutein or polypeptide can for example be produced in a bacterial or eucaryotic host organism and then isolated from this host organism or its culture. It is also possible to produce a protein in vitro, for example by use of an in vitro translation system.

When producing the mutein in vivo a nucleic acid encoding such mutein or polypeptide is introduced into a suitable bacterial or eukaryotic host organism by means of recombinant DNA technology (as already outlined above). For this purpose, the host cell is first transformed with a cloning vector that includes a nucleic acid molecule encoding a mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in hNGAL muteins of the disclosure. Accordingly, such muteins can be produced in a cell compartment having a reducing redox milieu, for example, in the cytoplasma of Gram-negative bacteria.

In case a mutein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the disclosure in the cytosol of a host cell, preferably *E. coli*. In this case, the mutein or polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8).

However, the mutein or polypeptide as described herein may not necessarily be generated or produced only by use of genetic engineering. Rather, such mutein or polypeptide can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for CGRP. Methods for the solid phase and/or solution phase synthesis of proteins are well known in the art (see e.g. Bruckdorfer, T. et al. (2004) *Curr Pharm. Biotechnol.* 5, 29-43).

In another embodiment, the mutein or polypeptide of the disclosure may be produced by in vitro transcription/translation employing well-established methods known to those skilled in the art.

The skilled worker will appreciate methods useful to prepare muteins or polypeptides thereof contemplated by the present disclosure but whose protein or nucleic acid sequences are not explicity disclosed herein. As an overview, such modifications of the amino acid sequence include, e.g., directed mutagenesis of single amino acid positions in order to simplify sub-cloning of a mutated hNGAL gene or its parts by incorporating cleavage sites for certain restriction enzymes. In addition, these mutations can also be incorporated to further improve the affinity of a mutein for its target (e.g. CGRP). Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

The muteins or polypeptides thereof disclosed herein and their derivatives can be used in many fields similar to antibodies or fragments thereof. For example, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, muteins or polypeptides thereof of the disclosure can serve to detect chemical structures by means of established analytical methods (e.g., ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1: Peptide Synthesis and Biotinylation of Calcitonin Gene-Related Peptides Calcitonin gene-related peptide (CGRP) is a neuroactive peptide. It occurs in two different isoforms, alpha and beta CGRP, and both isoforms from human and rat were generated by peptide synthesis (SEQ ID NOs: 80 to 83). Peptide solution was aliquoted in siliconized 1.5-mL tube (ThermoFisher, No. 02-681-320) and lyophilized by speed vacuum concentration system in siliconized 1.5-mL tubes (Thermo Fisher, No. 02-681-320). To re-dissolve the peptide 0.5% AcOH were added, and mixed thoroughly by tapping or pipetting.

For selection and screening of muteins of interest, the CGRP peptides may be biotinylated. In this regard, a Biotin group was directly coupled to the NH2 group of the N-terminal amino acid of the peptides during synthesis.

Example 2: Selection and Identification of Muteins Specifically Binding to CGRP Using Phage Display and High-Throughput ELISA Screening hNGAL-based libraries, generated by random mutagenesis of mature hNGAL, were used for selection of muteins specifically binding to the different CGRP targets. The four biotinylated human and rat CGRP a and 3 forms were used in independent phage display and selection processes either as single agents over the entire four rounds of selection or were applied alternatingly.

$2\times10^{12}$ phagemids from these libraries were incubated with 200 or 500 nM biotinylated target. Paramagnetic beads coated with neutravidin or streptavidin were used to capture target/phagemid complexes which were subsequently isolated with a magnet. Unbound phagemids were removed by washing the beads with PBST or PBS. Bound phagemids were first eluted with 300 μl 70 mM triethylamine for 10 min followed by immediate neutralization of the supernatant with 100 μl 1M Tris-Cl pH 6.0. After one intermediate wash cycle remaining phagemids were eluted with 100 mM glycine pH 2.2 for 10 min followed by immediate neutralization with 50 μl 0.5 M Tris-base. Both elution fractions were pooled and used to infect 4 mL of *E. coli* XL1-blue culture ($OD_{550}$ 0.45-0.6) for reamplification. After incubation for 30 min under agitation bacteria were collected by centrifugation at 5000×g for 2 min, resuspended in 1 mL 2×YT medium and plated on three big LB/Amp agar plates (10 g/l bacto tryptone, 5 g/l yeast extract, 5 g/l NaCl, pH 7.5, 15 g/l agar, 100 μg/mL ampicillin). Plates were incubated overnight at 32° C. Infected cells were scraped from the agar plates using 50 mL 2×YT medium supplemented with 100 μg/mL ampicillin (2×YT/Amp). 50 mL 2×YT/Amp medium were inoculated with the appropriate volume of bacterial suspension to reach an $OD_{550}$ of 0.08. The culture was incubated at 37° C. on a shaker (160 rpm) until an $OD_{550}$ of 0.5 was reached and then infected with helperphages ($1.5\times10^{11}$ pfu) by incubation for 15 min with gentle agitation and for 45 min on a shaker at 37° C. Subsequently, kanamycin was added to a final concentration of 70 μg/mL to select bacteria infected by helperphages. Finally, expression of the pIII-hNGAL muteins was induced by addition of 25 ng/mL anhydrotetracyclin.

After 15 h incubation at 24° C. the supernatant of the culture was cleared by centrifugation (5000×g for 20 min). Subsequently, 20 mL supernatant were passed through a polyethersulfone membrane with a pore size of 0.22 μm. To the filtrate 5 mL of a solution containing 20% (w/v) PEG-8000 and 15% (w/v) NaCl in water was added and gently mixed. The solution was incubated for 30 min on ice before centrifugation for 20 min at 4° C. & 5000×g. The pellet containing the phagemids was dissolved in 1 mL buffer containing 200 mM boric acid, 160 mM NaCl and 1 mM EDTA. Unsoluble particles were removed by centrifugation (5000×g for 5 min). The supernatant was transferred to a fresh tube and mixed with 200 μl of a solution containing 20% (w/v) PEG-8000 and 15% (w/v) NaCl in water. The solution was incubated 30 min on ice and precipitated phagemids were subsequently collected by centrifugation (5000×g for 5 min). Phagemids were resuspended in PBS supplemented with 50 mM benzamidine and used for the next round of phagemid selection. Four consecutive rounds of selection were performed.

Phagemid DNA was prepared from *E. coli* cells infected with the output of the fourth selection round and the hNGAL mutein cassette was isolated by digestion of the DNA with BstX1 and subsequent purification via agarose gel electrophoresis using standard methods (Sambrook et al., (1989) Molecular cloning: a laboratory manual). The hNGAL mutein cassette was inserted into the likewise cut vector, which allows bacterial production of the hNGAL muteins under the control of a tetracyclin promoter. $CaCl_2$-competent TG1-F-cells were transformed with the ligation mixture and plated on LB/Amp plates.

For optimization of CGRP-specific muteins, libraries were generated based on mutein SEQ ID NO: 4, and SEQ ID NO: 5 using either a biased randomization of selected positions or error prone polymerase chain reaction (PCR) based methods. The biased design was made such that for each of the selected positions the amino acid encoded corresponds to the amino acid found in the respective mother clone with a probability of 50-70%, while it can be a different amino acid with a 50-30% probability. With N the number of targeted positions and B as bias, the most probable number of exchanges per clone is $N\times(1-B)$. In order to facilitate expression in eukaryotic cells, the hNGAL-derived natural N-glycosylation site N65 was removed by the mutation N65D; and as for other potential N-glycosylation sites (Asn-X-Ser/Thr), the likelyhood to occur was reduced by setting a bias at those library positions.

Phage display was employed to select for optimized muteins with improved heat stability and binding affinity. The phagemid selection was conducted with increased stringency compared to the initial mutein selections and involved preincubation steps at elevated temperature and limiting target concentration.

To further optimize binding affinities of CGRP-specific muteins, additional libraries were generated based on mutein SEQ ID NO: 14, and SEQ ID NO: 11 using an error prone polymerase chain reaction (PCR) based method for SEQ ID NO: 14 and a biased randomization of selected positions for SEQ ID NO: 11. The biased design was made exactly as described before.

Phage display was employed to select for optimized muteins with improved heat stability and binding affinity. The phagemid selection was conducted with increased stringency compared to the initial mutein selections and involved preincubation steps at elevated temperature and limiting target concentration.

In order to facilitate expression in *E. coli*, the endogenous disulfide bond was removed. Libraries were generated based on mutein SEQ ID NO: 17, and SEQ ID NO: 27 using a biased randomization of positions Cysteine 76 and Cysteine 175 by employing TRIM oligonucleotides. Selection of muteins was performed as described but with increased stringency.

Individual colonies, which were obtained through the each selection process described above, were used to inoculate 2×YT/Amp medium and grown overnight (14-18 h) to stationary phase. Subsequently, 50 μl 2×YT/Amp were inoculated from the stationary phase cultures and incubated for 3 h at 37° C. and then shifted to 22° C. until an $OD_{595}$ of 0.6-0.8 was reached. Production of muteins was induced by addition of 10 μl 2×YT/Amp supplemented with 1.2 μg/mL anhydrotetracyclin. Cultures were incubated at 22°

C. until the next day. After addition of 40 μl of 5% (w/v) BSA in PBS/T and incubation for 1 h at 25° C. cultures were ready for use in screening assays. While 20 μl of the cultures were directly applied to the screening ELISA plate, the residual volume was incubated at 65° C. for 1 h.

Binding of the isolated muteins to CGRP was tested by coating a 1:1 mixture of neutravidin and streptavidin (5 μg/mL in PBS) overnight at 4° C. on microtiterplates. After blocking the plate with 2% BSA in PBST biotinylated CGRP was captured on the coated microtiterplates at a concentration of 1 μg/mL in PBS/T. Subsequently, 20 μl of BSA-blocked cultures (with or without previous heat incubation) were added to the microtiter plates and incubated for 1 h at 25° C. Bound muteins were detected with anti-Streptag antibody conjugated with horseradish peroxidase (1 h incubation; IBA, Boettingen). For quantification, 20 μl of QuantaBlu fluorogenic peroxidase substrate was added and the fluorescence was determined at an excitation wavelength of 330 nm and an emission wavelength of 420 nm.

In addition, reverse screening formats were applied, where the muteins were captured via the strep-tag on microtiter plates coated with anti-Streptag antibody and different concentrations of biotinylated target were added and detected via Extravidin-HRP (E2886; Sigma).

To select for muteins with increased affinity and stability screening was performed with i) reduced antigen concentration and/or ii) competition with unbiotinylated target and/or iii) incubation of the screening supernatant at 65° C. or 70° C. before addition to the target plate and/or iv) using reverse screening formats were the muteins were captured via the Streptag on microtiter plates coated with anti-Streptag antibody and different concentrations of biotinylated target was added and detected via extravidin-HRP (Sigma Aldrich, St. Louis, Mo.).

Clones which showed positive signals in ELISA screening described above were then sequenced and muteins were selected for further characterization. Amino acid sequences of selected muteins are shown in SEQ ID NOs: 2-40.

Example 3: Expression and Purification of Muteins

Muteins obtained from Example 2 (SEQ ID NOs: 2-40), for which nucleotide sequences coding are shown in SEQ ID NOs: 41-79, were expressed with C-terminal tag SAWSHPQFEK (SEQ ID NO: 84); including the SA linker and the Strep-Tag® II, WSHPQFEK (SEQ ID NO: 85) in *E. coli* in 2YT-Amp medium to purify the muteins after expression using Streptactin affinity chromatography and preparative size exclusion chromatography.

Example 4: Affinity of Muteins to Soluble Human and Rat CGRP Determined in an ELISA Based Setting Binding of lipocalin muteins to alpha and beta CGRP from human and rat in solution was tested in vitro using a competition ELISA assay format (FIG. 1). In this experiment, a constant concentration of non-biotinylated CGRP (0.5 μM) was incubated for 1 h with variable concentrations of lipocalin muteins SEQ ID NO: 2, SEQ ID NO: 3, SEQ ID NO: 4; SEQ ID NO: 5, and SEQ ID NO: 6. After this pre-incubation in solution, an aliquot of the lipocalin mutein/CGRP mixture was transferred to an ELISA plate coated with Neutravidin-captured human alpha CGRP-bio to measure the concentration of lipocalin muteins that was not blocked by non-biotinylated human alpha CGRP (SEQ ID NO: 80) and therefore could still be bound by the immobilized human alpha CGRP-bio (FIG. 1). This procedure was performed on another relevant CGRP species (human beta CGRP (SEQ ID NO: 81), rat alpha CGRP (SEQ ID NO: 82), rat beta CGRP (SEQ ID NO: 83)). All incubation steps were performed with shaking at 300 rpm, and the plate was washed after each incubation step with 80 μL PBS-T buffer (PBS, 0.05% Tween 20) for five times using a Biotek ELx405 select CW washer. In the first step, a 384-well ELISA plate was coated with 20 μL of Neutravidin at a concentration of 5 μg/mL in PBS over night at 4° C. After washing, the plate was blocked with 60 μL PBS-T/BSA (2% BSA in PBS containing 0.05% Tween 20) for 1 h at room temperature.

To allow for detection and quantification of plate-bound lipocalin muteins, the residual supernatants were discarded and 20 μL HRP-labeled anti-hNGAL antibody was added at a predetermined optimal concentration in PBS-T/BSA and incubated for 1 h at RT. The anti-hNGAL antibody had been obtained by immunization of rabbits with a mixture of muteins, and was subsequently coupled to HRP using a kit (EZ-link Plus Activated Peroxidase, Thermo Scientific) according to the manufacturer's instructions, to obtain the antibody-HRP conjugate. After washing, 20 μl fluorogenic HRP substrate (QuantaBlu, Thermo) was added to each well, and the reaction was allowed to proceed for 15 to 60 minutes. The fluorescence intensity of every well on the plate was read using a fluorescence microplate reader (Tecan or Molecular Devices). To evaluate the data, free mutein concentration, $c(\text{mutein})_{free}$, was calculated based on the standard curve results, and plotted versus ligand concentration, c(Ligand). To obtain the ligand concentration at which formation the ligand/mutein complex was blocked by 50% (IC50), the curves were fitted by nonlinear regression with a single-sites binding model according to $c(\text{mutein})_{free}=c(\text{mutein})_{tot}/(1+c(\text{Ligand})/\text{IC50}))$, with the total tracer concentration $c(\text{mutein})_{tot}$ and the IC50 value as free parameters. Curve fitting was performed using GraphPad Prism 4 software.

The resulting $IC_{50}$ values are summarized in Table 1. Muteins selected bind to all subtypes of the respective CGRP species as shown in FIG. 1.

TABLE 1

$IC_{50}$ values in a competition ELISA assay

| SEQ ID NO | Human alpha CGRP IC50 [nM] | Human beta CGRP IC50 [nM] | Rat alpha CGRP IC50 [nM] | Rat beta CGRP IC50 [nM] |
|---|---|---|---|---|
| SEQ ID NO: 2 | 55 | 46 | 35 | 47 |
| SEQ ID NO: 3 | 7.5 | 14 | >1000 | 12 |
| SEQ ID NO: 4 | 2.1 | 1.8 | 2.6 | 3 |
| SEQ ID NO: 5 | 36 | 28 | 21 | 27 |
| SEQ ID NO: 6 | 3.1 | >1000 | 0.77 | 1.6 |

Example 5: Affinity of Optimized Muteins Binding to CGRP Determined by SPR

SPR was used to measure binding kinetics and affinity of the optimized lipocalin muteins disclosed herein.

SPR analysis of the binding of the hNGAL muteins to human and rat CGRP alpha and beta was performed at 37° C. on a Biacore T200 instrument (GE Healthcare) using HBS-EP+ (1×; BR-1006-69; GE Healthcare) as running buffer.

The Biotin CAPture Kit (GE Healthcare) was used to immobilize biotinylated lipocalin muteins to a chip surface.

Muteins were biotinylated using standard NHS chemistry. Undiluted Biotin CAPture Reagent (streptavidin conjugated with ss-DNA oligo) was captured on a Sensor Chip CAP with the pre-immobilized complementary ss-DNA oligo. Thereafter, biotinylated muteins at 1 μg/mL were applied for 300 s at a flow rate of 5 μL/min.

CGRP species were applied in three concentrations of 30 nM, 3 nM and 0.3 nM at a flow rate of 30 μL/min or in a single concentration of 25 nM per cycle as shown in FIG. 2. The dilutions were injected with association times of 180 s and dissociation times of 5400 sec to obtain ka and kd information. Regeneration of the chip surface was achieved by injecting 6 M Guanidinium-HCl+0.25 M NaOH (120 s) with a flow rate of 10 μL/min. Injection of regeneration solutions was followed by an extra wash step with HBS-EP+(1×; BR-1006-69; GE Healthcare) running buffer and a stabilization period of 120 s.

The data were double-referenced by subtraction of the corresponding signals measured for the control channel (loaded with Biotin CAPture reagent only) and by subtraction of buffer injections from the binding responses. Association rate constant ka and dissociation rate constant kd for the binding reaction were determined using Biacore T200 Evaluation Software V2.0 for data processing and kinetic fitting. The data were globally fit with 1:1 binding model.

The values determined for ka, kd and the resulting equilibrium dissociation constant KD for SEQ ID NO: 4, SEQ ID NOs: 7 to 17, and SEQ ID NOs: 19 to 28 are summarized in Table 2. A graphical representation of the results is shown in FIG. 2A to 2D, for human and rat alpha and beta CGRP, respectively. Optimized CGRP specific lipocalin muteins bind both isoforms of human and rat CGRP with picomolar to low nanomolar affinity and affinities are up to 120-fold improved after optimization, while no significant binding of hNGAL wildtype (SEQ ID NO:1) as a control is detected.

Example 6: Functional Testing of Muteins Binding to CGRP in a cAMP Assay

The ability of the lipocalin muteins of SEQ ID NO: 11, SEQ ID NO: 14, SEQ ID NOs: 17 to 20, and SEQ ID NOs: 23 to 27 to neutralize the biological activity of human and rat CGRP was assessed by measuring cAMP, a second messenger, production in human SK-N-MC (Human brain neuroepithelioma) and in rat L6 (Rat skeletal muscle myoblasts), respectively, in response to CGPR treatment using HitHunter® c-AMP XS+ Kit (DiscoverX).

In this experiment, a constant concentration of human or rat CGRP was incubated with variable concentrations of lipocalin muteins for 90 minutes. After this pre-incubation in solution, an aliquot of the lipocalin mutein/CGRP mixture was incubated with SK-N-MC or L6 cells, respectively, to measure the residual CGRP induced cAMP production.

SK-N-MC cells were maintained in EMEM, supplement with 10% fetal calf serum and were cultured in cell culture flasks under standard conditions according to manufacturer's instruction (ATCC, 37° C., 5% $CO_2$ atmosphere).

L6 cells were maintained in DMEM, supplement with 10% fetal calf serum and were cultured in cell culture flasks under standard conditions according to manufacturer's instruction (ATCC, 37° C., 5% $CO_2$ atmosphere).

The detailed procedure of setting up the assay is hereby described as follows.

A fixed concentration of human or rat CGRP was incubated in solution with varying concentrations of SEQ ID NO: 11, SEQ ID NO: 14, SEQ ID NOs: 17 to 20, and SEQ ID NOs: 23 to 27 using a suitable starting concentration which was serially diluted at a 1:3 ratio down to the picomolar range in serum free culture media containing 0.5 mM IBMX and 0.1% BSA (Working Buffer). After 90 min incubation at room temperature, 5 μl of the reaction mixture was transferred in a white 384 well plate, which subsequently was preheated for 10 min at 37° C., 5% $CO_2$ directly before cell addition.

TABLE 2

Affinities, association rate constants ka and dissociation rate constants kd of optimized muteins for human and rat CGRP species as determined by SPR.

| | human αCGRP | | | human βCGRP | | | rat αCGRP | | | rat βCGRP | | |
|---|---|---|---|---|---|---|---|---|---|---|---|---|
| SEQ ID NO: | ka $[M^{-1} \cdot s^{-1}]$ | kd $[s^{-1}]$ | KD [nM] | ka $[M^{-1} \cdot s^{-1}]$ | kd $[s^{-1}]$ | KD [nM] | ka $[M^{-1} \cdot s^{-1}]$ | kd $[s^{-1}]$ | KD [nM] | ka $[M^{-1} \cdot s^{-1}]$ | kd $[s^{-1}]$ | KD [nM] |
| 4 | 1.66E+06 | 3.02E−03 | 1.82 | 5.24E+06 | 3.95E−03 | 0.753 | 1.24E+06 | 6.21E−03 | 5.00 | 1.66E+06 | 3.65E−03 | 2.19 |
| 7 | 3.74E+06 | 2.49E−04 | 0.067 | 5.21E+06 | 1.88E−04 | 0.036 | 1.04E+06 | 3.13E−04 | 0.30 | 3.04E+06 | 2.76E−04 | 0.091 |
| 8 | 2.07E+06 | 5.95E−04 | 0.288 | 3.70E+06 | 5.29E−04 | 0.143 | 7.34E+05 | 8.37E−04 | 1.14 | 1.82E+06 | 6.36E−04 | 0.349 |
| 9 | 5.88E+06 | 2.57E−04 | 0.044 | 6.80E+06 | 1.81E−04 | 0.027 | 1.22E+06 | 3.18E−04 | 0.26 | 3.68E+06 | 2.75E−04 | 0.075 |
| 10 | 1.26E+06 | 2.05E−04 | 0.163 | 2.14E+06 | 1.62E−04 | 0.076 | 5.59E+05 | 3.07E−04 | 0.55 | 1.08E+06 | 2.24E−04 | 0.206 |
| 11 | 3.08E+06 | 4.55E−05 | 0.015 | 7.91E+06 | 5.63E−05 | 0.007 | 9.84E+05 | 7.60E−05 | 0.08 | 1.74E+06 | 7.30E−05 | 0.042 |
| 12 | 1.08E+06 | 1.62E−04 | 0.15 | 1.10E+06 | 1.04E−04 | 0.095 | 6.61E+05 | 2.99E−04 | 0.45 | 1.17E+06 | 2.05E−04 | 0.176 |
| 13 | 5.82E+06 | 4.36E−04 | 0.075 | 1.18E+07 | 3.66E−04 | 0.031 | 1.85E+06 | 5.25E−04 | 0.28 | 3.16E+06 | 3.50E−04 | 0.111 |
| 14 | 2.56E+06 | 1.41E−04 | 0.055 | 4.56E+06 | 1.41E−04 | 0.031 | 1.19E+06 | 3.39E−04 | 0.29 | 1.69E+06 | 1.81E−04 | 0.107 |
| 15 | 6.32E+06 | 2.38E−04 | 0.038 | 1.53E+07 | 2.73E−04 | 0.018 | 1.59E+06 | 2.74E−04 | 0.17 | 4.98E+06 | 1.93E−04 | 0.039 |
| 16 | 5.02E+06 | 2.59E−04 | 0.052 | 1.01E+07 | 3.64E−04 | 0.036 | 1.41E+06 | 3.98E−04 | 0.28 | 2.37E+06 | 2.29E−04 | 0.097 |
| 25 | 2.68E+06 | 1.65E−05 | 0.006 | 2.02E+06 | 1.01E−05 | 0.005 | 1.30E+06 | 2.12E−05 | 0.016 | 1.64E+06 | 1.33E−05 | 0.008 |
| 24 | 1.60E+06 | 1.40E−05 | 0.009 | 2.52E+06 | 9.01E−06 | 0.004 | 1.43E+06 | 2.08E−05 | 0.015 | 1.69E+06 | 1.22E−05 | 0.007 |
| 23 | 1.64E+06 | 1.84E−05 | 0.011 | 2.84E+06 | 4.11E−06 | 0.001 | 1.39E+06 | 1.30E−05 | 0.009 | 1.74E+06 | 1.34E−05 | 0.008 |
| 26 | 1.50E+06 | 1.99E−05 | 0.013 | 2.44E+06 | 7.60E−06 | 0.003 | 1.31E+06 | 2.01E−05 | 0.015 | 1.56E+06 | 9.98E−06 | 0.006 |
| 27 | 1.43E+06 | 2.59E−05 | 0.018 | 2.04E+06 | 2.26E−05 | 0.011 | 8.07E+05 | 3.10E−05 | 0.038 | 1.50E+06 | 2.64E−05 | 0.018 |
| 28 | 1.59E+06 | 4.99E−05 | 0.031 | 2.52E+06 | 3.41E−05 | 0.014 | 1.41E+06 | 6.88E−05 | 0.049 | 1.72E+06 | 5.48E−05 | 0.032 |
| 19 | 2.26E+06 | 1.07E−05 | 0.005 | 4.56E+06 | 6.67E−06 | 0.001 | 1.25E+06 | 3.02E−05 | 0.024 | 2.01E+06 | 1.21E−05 | 0.006 |
| 22 | 1.76E+06 | 1.56E−05 | 0.009 | 2.70E+06 | 9.32E−06 | 0.003 | 9.31E+05 | 3.05E−05 | 0.033 | 1.60E+06 | 2.02E−05 | 0.013 |
| 17 | 3.34E+06 | 3.66E−05 | 0.011 | 1.36E+07 | 1.44E−05 | 0.001 | 2.75E+06 | 8.44E−05 | 0.031 | 5.18E+06 | 5.99E−05 | 0.012 |
| 20 | 1.45E+06 | 1.75E−05 | 0.012 | 2.18E+06 | 7.89E−06 | 0.004 | 8.67E+05 | 2.41E−05 | 0.028 | 1.38E+06 | 1.84E−05 | 0.013 |
| 21 | 1.21E+06 | 1.71E−05 | 0.014 | 2.36E+06 | 8.74E−06 | 0.004 | 7.03E+05 | 3.70E−05 | 0.053 | 1.34E+06 | 2.36E−05 | 0.018 |

The adherent cells, human SK-N-MC or rat L6, cells were dissociated from their substrate with accutase and resuspended in PBS. Subsequently, cells were centrifuged down for 5 minutes at 300 g, and cell number was adjusted to $3\times10^6$ cells/mL in Antibody Working Solution (2/3 Working Buffer, 1/3 HitHunter® Antibody Solution) according to manufacturer's instruction.

30.000 cells/well (10 µl) were added to the plate and covered with gas permeable adhesive seal.

cAMP production was then allowed 30 min at 37° C., 5% CO2.

Subsequently, 20 µl ED/Lysis/CL Working Solution (19 parts Lysis Buffer, 1 part Galacton Star, 5 parts Emerald, 25 parts cAMP XS+ED Reagent) were added and the plate and incubated for 1 h protected from light at room temperature.

20 µl EA reagent were added to the cells in each of the wells, and luminescence was measured after 1-18 h using the PheraStar.

Evaluation and curve fitting was performed using GraphPad Prism 4 software. A graphical representation of the results is shown in FIG. 3A to 3D, for human and rat alpha and beta CGRP, respectively. The resulting IC50 values are summarized in Table 3 below.

TABLE 3

IC50 values of muteins from a functional cAMP assay using human and rat CGRP species.

| SEQ ID NO | human αCGRP IC50 [nm] | human βCGRP IC50 [nM] | rat αCGRP IC50 [nM] | rat βCGRP IC50 [nM] |
|---|---|---|---|---|
| 11 | 0.11 | 0.22 | 0.08 | 0.06 |
| 27 | 0.1 | 0.12 | — | — |
| 25 | 0.15 | 0.19 | 0.06 | 0.16 |
| 24 | 0.12 | 0.19 | 0.07 | 0.16 |
| 23 | 0.18 | 0.2 | 0.07 | 0.17 |
| 26 | 0.16 | 0.26 | 0.05 | 0.16 |
| 14 | 0.15 | 1.5 | 0.12 | 0.09 |
| 19 | 0.14 | 0.21 | 0.07 | 0.17 |
| 20 | 0.14 | 0.17 | 0.08 | 0.11 |
| 18 | 0.19 | 0.29 | 0.06 | 0.14 |
| 17 | 0.11 | 0.23 | 0.06 | 0.11 |

Example 7: Characterization of Cysteine-Free Lipocalin Muteins Specific for CGRP Biacore affinities of CGRP-specific muteins (SEQ ID NO: 17, SEQ ID NO: 27, and cysteine-free muteins SEQ ID NOs: 29 to 40) towards human alpha and beta CGRP were determined by using SPR method as identically described in Example 5. The resulting KD values are listed in Table 4.

A cAMP assay was employed in the same way as described in Example 6 to determine the functional potency of CGRP-specific muteins SEQ ID NO: 17, SEQ ID NO: 27, and cysteine-free muteins SEQ ID NOs: 29 to 40 (see FIGS. 4A and 4B). The resulting IC50 values for human alpha and beta CGRP species are summarized in Table 4.

A fluorescence-based thermal denaturation assay (commonly referred to as Thermal shift assay of differential scanning fluorometry) was employed to measure the thermal stability of CGRP-specific muteins (SEQ ID NO: 17, SEQ ID NO: 27, and cysteine-free muteins SEQ ID NOs: 29 to 40) using Mx3005P qPCR System (Agilent Technologies).

Therefore lipocalin mutein solutions were diluted to a concentration of 10 µM in phosphate-buffered saline (PBS; pH 7.4; 10010; Life Technologies) and a 15-fold stock solution in PBS of the fluorescent dye SYPRO Orange (5000× concentrate in DMSO; S-6650; Life technologies) was prepared. 20 µl of protein dilution was mixed with 5 µl of SYPRO Orange stock in a qPCR plate (FrameStar 96 non skirted; Cat No 4ti-0711; 4titude) and the plate was sealed with caps (Flat Optically Clear Caps; Cat No 4Ti-0751; 4titude). Using an Mx3005P qPCR System the plate was gradually heated from 25° C. to 100° C. (45 s/step) while the fluorescence signal was recorded at an excitation wavelength of 492 nm and an emission wavelength of 610 nm.

An increase in fluorescence indicates protein unfolding, as SYPRO Orange binds nonspecifically to hydrophobic surfaces and water strongly quenches the fluorescence of Sypro Orange (James K. Kranz. Celine Schalk-Hihi (2011); "Protein thermal shifts to identify low molecular weight fragments"; Methods Enzymol. 493: 277-298; doi: 10.1016B978-0-12-381274-2.00011-X; PMID 21371595).

Savitzky-golay smoothing (5× savitzky golay filter) was applied to the raw data (fluorescence signal over temperature) and the first derivative was calculated. For determination of the melting temperature Tm the maximum of the first derivative (corresponding to the inflection point of the fluorescence-over-temperature curve) was read out and matched with the corresponding temperature (=Tm). The complete evaluation was performed in Microsoft Excel.

The melting temperatures (Tm) of the lipocalin muteins as determined in the thermal shift assay described above are compiled in Table 4.

TABLE 4

SPR affinities (KD), functional potencies (IC50) and melting temperatures (Tm) of cysteine-free muteins are summarized in the following table.

| | SPR KD [nM] | | cAMP assay IC50 [nM] | | |
|---|---|---|---|---|---|
| SEQ ID NO: | hαCGRP | hβCGRP | hαCGRP | hβCGRP | Tm [° C.] |
| 17 | 0.020 | 0.003 | 0.09 | 0.13 | 75 |
| 29 | 0.065 | 0.050 | 0.14 | 0.91 | 69 |
| 30 | 0.109 | 0.075 | 0.22 | 1.32 | 69 |
| 27 | 0.038 | 0.007 | 0.1 | 0.12 | 80 |
| 31 | 0.033 | 0.043 | 0.19 | 1.64 | 73 |
| 32 | 0.034 | 0.021 | 0.17 | 0.26 | 76 |
| 33 | 0.034 | 0.018 | 0.14 | 0.24 | 76 |
| 34 | 0.041 | 0.025 | 0.12 | 0.29 | 79 |
| 35 | 0.045 | 0.017 | 0.15 | 0.27 | 77 |
| 36 | 0.046 | 0.022 | 0.25 | 0.81 | 73 |
| 37 | 0.055 | 0.023 | 0.16 | 0.77 | 72 |
| 38 | 0.059 | 0.026 | 0.21 | 3.16 | 74 |
| 39 | 0.062 | 0.034 | 0.21 | 1.03 | 76 |
| 40 | 0.070 | 0.023 | 0.18 | 0.42 | 78 |

Example 8: Preparation of Tag-Free Lipocalin Muteins

With reference to the amino acid sequences of lipocalin muteins (SEQ ID NOs: 34 and 17), tag-free lipocalin muteins were designed as shown in SEQ ID NOs: 87 and 88, respectively. N-terminal Gly was attached in order to avoid the formation of pyroglutamic acid from Gln, which is originally N-terminal amino acid of the mature hNGAL (SEQ ID NO: 1). To produce them, nucleotide sequences (SEQ ID NOs: 94 and 95) corresponding to the amino acid sequences of tag-free lipocalin muteins (SEQ ID NOs: 87 and 88) were subcloned into *E. coli* expression vectors. Furthermore, based on the nucleotide sequence (SEQ ID NO: 95), two or more bases were substituted by PCR-based site-directed mutagenesis. The resulting nucleotide sequences (SEQ ID NOs: 96-100), which encode lipocalin muteins (SEQ ID NOs: 89-93), were also subcloned into *E. coli* expression vectors.

Using the above-described vectors, *E. coli* expression was performed using the medium (MagicMedia™ (Life Technologies)). To facilitate purification, lipocalin muteins, of which N-terminal amino acid is Gly (SEQ ID NOs: 87-93), were expressed with N-terminal tag MRGSHHHHHHGSENLYFQ (SEQ ID NO: 86) including $His_6$-tag and a part of the TEV protease-recognition motif which is an amino acid sequence consisting of E(Glu) 13 to Q(Gln) 18 of SEQ ID NO: 86, so that each expression product could be cleaved by TEV protease of which amino acid sequence and the corresponding nucleotide sequence are shown in SEQ ID NOs: 101 and 102, respectively. The expression products were purified by immobilized-metal affinity chromatography using TALON CellThru Resin (Clontech), followed by the removal of the tag using TEV protease. TEV protease cleaved between Q(Gln) and G(Gly), and as a result, purified tag-free lipocalin muteins had N-terminal Gly (SEQ ID NOs: 87-93). Further purification was performed by anion exchange chromatography using HiTrap Q FF columns (GE Healthcare) and size exclusion chromatography using HiLoad 16/600 Superdex 75 pg column (GE Healthcare).

Example 9: Characterization of Tag-Free Lipocalin Muteins

SPR analysis of the binding of the tag-free muteins to human alpha CGRP was performed at 37° C. on a Biacore T200 instrument (GE Healthcare) using HBS-EP+ as running buffer.

The Biotin CAPture Kit (GE Healthcare) was used to immobilized biotinylated lipocalin muteins to a chip surface. Muteins were biotinylated using standard NHS chemistry. Fifty-fold diluted Biotin CAPture Reagent (streptavidin conjugated with ss-DNA oligo) was captured on a Sensor Chip CAP with the pre-immobilized complementary ss-DNA oligo. Thereafter, biotinylated muteins at 200 nM were applied for 60 s at a flow rate of 10 μL/min.

Human alpha CGRP was applied in concentrations ranging from 0.0256 nM to 5 nM at a flow rate of 30 μL/min. The dilutions were injected with association times of 600 s and dissociation times of 1800 s. Regeneration of the chip surface was achieved by injecting 6 M Guanidinium-HCl+0.25 M NaOH (120 s) with a flow rate of 10 μL/min, followed by injecting 30% acetonitrile+0.25 M NaOH (120 s) with a flow rate of 10 μL/min. Injection of regeneration solutions was followed by an extra wash step with HBS-EP+ running buffer and a stabilization period of 60 s.

The data were double-referenced by subtraction of the corresponding signals measured for the control channel (loaded with Biotin CAPture reagent only) and by subtraction of buffer injections from the binding responses. Association rate constant ka and dissociation rate constant kd for the binding reaction were determined using Biacore T200 Evaluation Software version 1.0 for data processing and kinetic fitting. The data were globally fit with 1:1 binding model.

Resulting KD values for tag-free muteins (SEQ ID NOs: 87-93) are shown in Table 5. A graphical representation of the results is shown in FIG. 5.

To determine the functional potency of tag-free muteins SEQ ID NOs: 87 to 93, cAMP assay was employed in the same way as described in Example 6 with minor modifications as follows: (1) 5,000 cells/well were added to the plate. (2) Luminescence was measured using EnSpire (Perkin Elmer).

The resulting IC50 values for human alpha CGRP are summarized in Table 5.

TABLE 5

SPR affinity (KD) and functional potency (IC50) of tag-free muteins.

| SEQ ID NO: | SPR KD [nM] | cAMP assay IC50 [nM] |
|---|---|---|
| 87 | 0.081 | 0.66 |
| 88 | 0.008 | 0.17 |
| 89 | 0.006 | 0.17 |
| 90 | 0.012 | 0.16 |
| 91 | 0.010 | 0.16 |
| 92 | 0.010 | 0.18 |
| 93 | 0.011 | 0.13 |

Example 10: Effect of Lipocalin Muteins on Rat Skin Vasodilatation Induced by Electrical Stimulation of Saphenous Nerve To test antagonist activity of CGRP specific lipocalin muteins (SEQ ID NOs: 11, 17, 18, 23, 25, 27, 87 and 89), effect of the muteins on skin vasodilatation by stimulation of rat saphenous nerve was tested using a rat model (Br J Pharmacol., 1993, 110(2):772-6) with the following modifications. Sprague Dawley rats were pre-treated with guanethidine sulfate (20 mg/kg, sc) a day before experiments to block sympathetic activity. Rats were anaesthetized with thiobutabarbital (100 mg/kg, ip) and maintained with 0.5-1% isoflurane. The saphenous nerve of the hind limb was exposed surgically, cut proximally and placed over platinum bipolar electrodes for stimulation. During experiment, the nerve was covered with surgical cotton dipped in liquid paraffin to prevent it from drying. Skin blood flow was measured on the mediodorsal side of the hind paw using a skin probe connected to a laser Doppler flow metre. After a stable baseline flux (less than 5% variation) had been established, the distal end of the saphenous nerve was electrically stimulated with 30 pulses (2 Hz, 10V, 1 ms, for 15 sec) 125 minutes after administration. All muteins and vehicle were administrated subcutaneously.

All data were recorded using chart software (LabChart 7, ADInstruments Pty. Ltd.). Cumulative change in skin blood flow was estimated by the area under the flux-time curve (AUC) for each flux response to electrical pulse stimulation. Inhibitory effect of muteins on blood flow increase (AUC) by electrical stimulation was calculated in comparison with vehicle treatment group as blood flow inhibition. (shown in Table 6)

TABLE 6 rat skin blood flow assay

| SEQ ID NO: | Dose (mg/kg, sc) | Time after administration (min) | Blood flow inhibition (% of vehicle) |
|---|---|---|---|
| 11 | 3 | 125 | 79.7 |
| 17 | 3 | 125 | 81.9 |
| 18 | 0.3 | 125 | 39.1 |
| 23 | 0.3 | 125 | 49.9 |
| 25 | 0.3 | 125 | 40 |
| 27 | 3 | 125 | 81.6 |

TABLE 6-continued

| rat skin blood flow assay | | | |
|---|---|---|---|
| SEQ ID NO: | Dose (mg/kg, sc) | Time after administration (min) | Blood flow inhibition (% of vehicle) |
| 87 | 3 | 125 | 69.4 |
| 89 | 2.5 | 125 | 64.4 |

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

EQUIVALENTS

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A method of treating, preventing, or ameliorating a disease or disorder associated with deregulated protein plasma extravasation in a subject, comprising administering to the subject a human neutrophil gelatinase associated lipocalin (hNGAL) mutein that is capable of binding CGRP with detectable affinity.

2. The method of claim 1, wherein the disease or disorder is selected from the group consisting of migraine, temporomandibular joint disorder, cardiac failure, hypertension and sepsis.

3. The method of claim 1, wherein the disease or disorder is migraine.

4. The method of claim 1, wherein the hNGAL mutein is capable of binding CGRP with a KD of about 5 nM or lower.

5. The method of claim 1, wherein the hNGAL mutein is crossreactive with both human CGRP and rat CGRP.

6. The method of claim 1, wherein the hNGAL mutein is capable of inhibiting or reducing CGRP-induced cAMP production with an IC50 value of about 5 nM or lower.

7. The method of claim 1, wherein the hNGAL mutein comprises eleven or more of the following mutated amino acid residues in comparison with the linear polypeptide sequence of mature hNGAL (SEQ ID NO: 1): Leu 36→Ile, Phe, Trp, Arg or Glu; Ala 40→Asp, Glu, Met, Trp or Thr; Ile 41→Ala, Arg, Val, Thr, Leu, Trp, Gly or Glu; Gln 49→Ile, Pro, Leu, Phe, Lys, Glu or Thr; Tyr 52→Ala, Gly, Glu or Gln; Ser 68→Trp, His or Asp; Leu 70→Met, Trp, Tyr, Gly or Gln; Arg 72→Val, Ala, Met, Ile, Trp, Glu or Ser; Lys 73→Arg, Asp, Ala, Glu, Thr or Gln; Asp 77→Met, Arg, Ile or Asn; Trp 79→Val, Gly, His or Thr; Arg 81→Gly, His, Glu or Asn; Asn 96→Leu, Ala, Gly or Thr; Tyr 100→His, Ile, Pro or Glu; Leu 103→Val, Met, Glu, Thr or Gln; Tyr 106→Gly, Leu, Ile, Ala, His or Asn; Lys 125→Leu, Val, Phe, Gly or Glu; Ser 127→Asn, Gly, Lys, Phe, Trp or Arg; Tyr 132→Ser, Leu, Ile or Trp; and Lys 134→Trp, His or Glu, and wherein the hNGAL mutein has at least 85% sequence identity to an amino acid sequence selected from the group consisting of SEQ ID NOs: 2-40 and 87-93.

8. The method of claim 1, wherein the hNGAL mutein comprises one of the following sets of mutated amino acid residues in comparison with the linear polypeptide sequence of mature hNGAL (SEQ ID NO: 1):

(a) Gln 28→His; Leu 36→Trp; Ala 40→Thr; Ile 41→Leu; Gln 49→Ile; Tyr 52→Gln; Ser 68→Trp; Leu 70→Tyr; Arg 72→Ser; Lys 73→Glu; Lys 75→Arg; Asp 77→Asn; Trp 79→His; Arg 81→Glu; Phe 83→Ser; Cys 87→Ser; Asn 96→Thr; Leu 103→Glu; Tyr 106→Ile; Lys 125→Gly; Tyr 132→Ile; Lys 134→Glu;

(b) Gln 28→His; Leu 36→Trp; Ala 40→Thr; Ile 41→Leu; Leu 42→Arg; Asp 47→Asn; Gln 49→Thr; Tyr 52→Gln; Ser 68→Trp; Leu 70→Tyr; Arg 72→Ser; Lys 73→Glu; Asp 77→Asn; Trp 79→His; Arg 81→Glu; Phe 83→Ser; Cys 87→Ser; Asn 96→Thr; Leu 103→Glu; Tyr 106→Ile; Lys 125→Gly; Tyr 132→Ile; Lys 134→Glu;

(c) Gln 28→His; Leu 36→Trp; Ala 40→Thr; Ile 41→Leu; Gln 49→Ile; Tyr 52→Gln; Asn 65→Asp; Ser 68→Trp; Leu 70→Tyr; Phe 71→Leu; Arg 72→Ser; Lys 73→Glu; Asp 77→Asn; Trp 79→His; Arg 81→Glu; Phe 83→Ser; Cys 87→Ser; Asn 96→Thr; Leu 103→Glu; Tyr 106→Ile; Lys 125→Gly; Val 126→Met; Tyr 132→Ile; Lys 134→Glu; Thr 145→Ala;

(d) Gln 28→His; Leu 36→Trp; Ala 40→Thr; Ile 41→Leu; Asp 47→Asn; Gln 49→Thr; Tyr 52→Gln; Val 66→Ala; Ser 68→Trp; Leu 70→Tyr; Phe 71→Leu; Arg 72→Ser; Lys 73→Glu; Asp 77→Asn; Trp 79→His; Arg 81→Glu; Phe 83→Ser; Cys 87→Ser; Asn 96→Thr; Ile 97→Thr; Leu 103→Glu; Ser 105→Pro; Tyr 106→Ile; Lys 125→Gly; Tyr 132→Ile; Lys 134→Glu;

(e) Gln 28→His; Leu 36→Trp; Ala 40→Thr; Ile 41→Leu; Gln 49→Ile; Tyr 52→Gln; Thr 54→Ile; Lys 62→Arg; Ser 68→Trp; Leu 70→Tyr; Arg 72→Ser; Lys 73→Glu; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(f) Gln 28→His; Leu 36→Trp; Ala 40→Thr; Ile 41→Leu; Gln 49→Pro; Tyr 52→Gln; Lys 62→Arg; Ser 68→Trp; Leu 70→Tyr; Arg 72→Ser; Lys 73→Glu; Asp 77→Asn; Trp 79→His; Arg 81→Glu; Phe 83→Ser; Cys 87→Ser; Asn 96→Thr; Lys 98→Gln; Tyr 100→His; Leu 103→Glu; Ser 105→Pro; Tyr 106→Ile; Lys 125→Gly; Val 126→Met; Ser 127→Gly; Tyr 132→Ile; Lys 134→Glu;

(g) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Asp; Asp 77→Asn; Trp 79→His; Arg 81→Glu; Cys 87→Ser; Asn 96→Leu; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(h) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Glu; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(i) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Asp; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(j) Gln 28→His; Leu 36→Trp; Ala 40→Thr; Ile 41→Leu; Gln 49→Ile; Tyr 52→Gln; Thr 54→Lys; Lys 62→Arg; Ser 68→Trp; Leu 70→Tyr; Arg 72→Ala; Lys 73→Asp; Asp 77→Arg; Trp 79→His; Arg 81→Glu; Cys 87→Ser; Asn 96→Thr; Tyr 100→His; Leu 103→Glu; Ser 105→Pro; Tyr 106→Ile; Lys 125→Gly; Ser 127→Asn; Tyr 132→Ile; Lys 134→Glu; Thr 136→Ile; Ser 146→Asn;

(k) Gln 28→His; Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn;

(l) Gln 28→His; Leu 36→Trp; Ala 40→Thr; Ile 41→Leu; Gln 49→Ile; Tyr 52→Gln; Thr 54→Ile; Lys 62→Arg; Ser 68→Trp; Leu 70→Tyr; Arg 72→Ser; Lys 73→Glu; Asp 77→Asn; Trp 79→His; Arg 81→Glu; Cys 87→Ser; Asn 96→Thr; Leu 103→Glu; Ser 105→Pro; Tyr 106→Ile; Val 111→Met; Lys 125→Gly; Ser 127→Asn; Tyr 132→Ile; Lys 134→Glu; Thr 136→Ile; Ser 146→Asn;

(m) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Arg; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Phe;

(n) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Met; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Tyr;

(o) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Leu; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Trp;

(p) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Ile; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Glu;

(q) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Val; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Tyr;

(r) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Arg; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Trp;

(s) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Asn; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Leu;

(t) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Arg; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Val;

(u) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Lys; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Asp; and (v) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Phe; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Asp.

9. The method of claim 1, wherein the hNGAL mutein comprises one of the following sets of mutated amino acid residues in comparison with the linear polypeptide sequence of mature hNGAL (SEQ ID NO: 1):

(a) Gln 28→His; Leu 36→Arg; Ala 40→Glu; Ile 41→Glu; Tyr 52→Glu; Ser 68→Asp; Leu 70→Gly; Arg 72→Ser; Lys 73→Glu; Asp 77→Ile; Trp 79→Val; Arg 81→His; Cys 87→Ser; Leu 103→Val; Tyr 106→Ala; Lys 125→Val; Ser 127→Lys; Tyr 132→Leu; Lys 134→Glu;

(b) Gln 28→His; Leu 36→Arg; Ala 40→Asp; Ile 41→Ala; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Ala; Lys 125→Leu; Ser 127→Lys; Tyr 132→Leu; Lys 134→Glu;

(c) Gln 28→His; Leu 36→Arg; Gly 38→Ala; Ala 40→Asp; Ile 41→Arg; Gln 49→Glu; Tyr 52→Glu; Ser 68→Asp; Leu 70→Gly; Arg 72→Ser; Lys 73→Arg; Asp 77→Ile; Trp 79→Val; Arg 81→His; Cys 87→Ser; Leu 103→Thr; Tyr 106→Gly; Lys 125→Val; Ser 127→Gly; Tyr 132→Ser; Lys 134→Glu;

(d) Gln 28→His; Leu 36→Arg; Ala 40→Asp; Ile 41→Glu; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Gly; Lys 125→Val; Ser 127→Arg; Tyr 132→Leu; Lys 134→Glu;

(e) Gln 28→His; Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu;

(f) Gln 28→His; Leu 36→Arg; Gly 38→Ala; Ala 40→Asp; Ile 41→Val; Glu 44→Asp; Lys 46→Asn; Gln 49→Glu; Tyr 52→Glu; Ser 68→Asp; Leu 70→Gly; Arg 72→Val; Lys 73→Gln; Asp 77→Met; Trp 79→Val; Ile 80→Val; Arg 81→His; Cys 87→Ser; Leu 103→Val; Tyr 106→Ala; Lys 125→Leu; Ser 127→Lys; Tyr 132→Leu; Lys 134→Glu; Ile 135→Val;

(g) Gln 28→His; Leu 36→Arg; Ala 40→Asp; Ile 41→Thr; Gln 49→Glu; Tyr 52→Glu; Ser 68→Asp; Leu 70→Gly; Phe 71→Leu; Arg 72→Val; Lys 73→Gln; Asp 77→Met; Trp 79→Val; Arg 81→His; Cys 87→Ser; Leu 103→Val; Tyr 106→Ala; Phe 123→Val; Lys 125→Leu; Ser 127→Lys; Asn 129→Ser; Tyr 132→Leu; Lys 134→Glu;

(h) Gln 28→His; Leu 36→Arg; Ala 40→Asp; Ile 41→Thr; Glu 44→Lys; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Ala; Phe 123→Val; Lys 125→Leu; Ser 127→Lys; Tyr 132→Leu; Lys 134→Glu;

(i) Gln 28→His; Leu 36→Arg; Ala 40→Asp; Ile 41→Ala; Gln 49→Glu; Tyr 52→Glu; Ser 68→Asp; Leu 70→Gly; Arg 72→Val; Lys 73→Gln; Asp 77→Met; Trp 79→Val; Arg 81→His; Cys 87→Ser; Leu 103→Val; Tyr 106→Ala; Val 108→Ile; Ser 112→Asn; Phe 123→Val; Lys 125→Leu; Ser 127→Lys; Tyr 132→Leu; Lys 134→Glu;

(j) Gln 28→His; Leu 36→Arg; Ala 40→Asp; Ile 41→Ala; Gln 49→Glu; Tyr 52→Glu; Ser 68→Asp; Leu 70→Gly; Phe 71→Leu; Arg 72→Val; Lys 73→Gln; Asp 77→Met; Trp 79→Val; Arg 81→His; Cys 87→Gly; Leu 103→Val; Tyr 106→Ala; Phe 123→Val; Lys 125→Leu; Ser 127→Lys; Tyr 132→Leu; Lys 134→Glu;

(k) Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Cys 76→Leu; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Cys 175→Ile; Ile 176→Asp; Asp 177→Gly;

(l) Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Cys 76→Tyr; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys

125→Leu; Ser 127→Lys; Tyr 132→Leu; Lys 134→Glu; Cys 175→Ile; Ile 176→Asp; Asp 177→Gly;

(m) Leu 36→Trp; Ala 40→Thr; Ile 41→Leu; Gln 49→Ile; Tyr 52→Gln; Thr 54→Met; Ser 68→Trp; Leu 70→Tyr; Arg 72→Ala; Lys 73→Asp; Cys 76→Ile; Asp 77→Asn; Trp 79→His; Arg 81→Glu; Cys 87→Ser; Asn 96→Thr; Leu 103→Glu; Ser 105→Pro; Tyr 106→Ile; Lys 125→Gly; Ser 127→Asn; Tyr 132→Ile; Lys 134→Glu; Thr 136→Val; Ser 146→Asn; Cys 175→Glu; a Gly is added to the N-terminal of Gln 1;

(n) Gln 28→His; Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; a Gly is added to N-terminal of Gln 1;

(o) Gln 28→His; Leu 36→Arg; Ala 40→Asp; Ile 41→Val; Gln 49→Glu; Tyr 52→Glu; Asn 65→Gln; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Gly 178→Asp; a Gly is added to the N-terminal of Gln 1;

(p) Ile 8→Lys; Gln 28→His; Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; a Gly is added to the N-terminal of Gln 1;

(q) Pro 9→His; Gln 28→His, Leu 36→Arg; Ala 40→Asp; Ile 41→Val; Gln 49→Glu; Tyr 52→Glu; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; a Gly is added to the N-terminal of Gln 1;

(r) Ile 8→Lys; Gln 28→His; Leu 36→Arg; Ala 40→Asp; Ile 41→Val; Gln 49→Glu; Tyr 52→Glu; Asn 65→Gln; Ser 68→Asp; Leu 70→Gly; Arg 72→Val; Lys 73 Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Gly 178→Asp; a Gly is added to the N-terminal of Gln 1; and (s) Pro 9→His; Gln 28→His; Leu 36→Arg; Ala 40→Asp; Ile 41→Val; Gln 49→Glu; Tyr 52→Glu; Asn 65→Gln; Ser 68→Asp; Leu 70→Gly; Arg 72→Val; Lys 73→Gln; Lys 75→Arg; Asp 77→Met; Trp 79→Val; Ile 80→Thr; Arg 81→His; Cys 87→Ser; Lys 98→Glu; Leu 103→Val; Tyr 106→Ala; Asn 114→Asp; Phe 123→Val; Lys 125→Leu; Ser 127→Lys; Tyr 132→Leu; Lys 134→Glu; Gly 178→Asp; a Gly is added to the N-terminal of Gln 1.

10. The method of claim 1, wherein the hNGAL mutein has at least 95% sequence identity to an amino acid sequence selected from the group consisting of SEQ ID NOs: 2-40 and 87-93.

11. The method of claim 1, wherein the hNGAL mutein comprises an amino acid sequence selected from the group consisting of SEQ ID NOs: 2-40 and 87-93.

12. The method of claim 1, wherein the hNGAL mutein comprises the amino acid sequence of SEQ ID NO: 17.

13. The method of claim 1, wherein the hNGAL mutein comprises the amino acid sequence of SEQ ID NO: 88.

14. The method of claim 1, wherein the hNGAL mutein comprises the amino acid sequence of SEQ ID NO: 89.

15. The method of claim 1, wherein the hNGAL mutein is fused at its N-terminus and/or its C-terminus to a fusion partner which is a protein, or a protein domain or a peptide.

16. The method of claim 1, wherein the hNGAL mutein is conjugated to a compound that extends the serum half-life of said mutein selected from a polyethylene glycol molecule, hydroxyethyl starch, an Fc part of an immunoglobulin, a CH3 domain of an immunoglobulin, a CH4 domain of an immunoglobulin, an albumin binding peptide, and an albumin binding protein.

17. A method of treating, preventing, or ameliorating migraine in a subject, comprising administering to the subject a human neutrophil gelatinase associated lipocalin (hNGAL) mutein that is capable of binding CGRP with detectable affinity, wherein the hNGAL mutein comprises the amino acid sequence of SEQ ID NO: 89.

* * * * *

SEQUENCE LISTING

```
<160> NUMBER OF SEQ ID NOS: 102

<210> SEQ ID NO 1
<211> LENGTH: 178
<212> TYPE: PRT
<213> ORGANISM: human

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

```
                165                 170                 175

Asp Gly


<210> SEQ ID NO 2
<211> LENGTH: 178
<212> TYPE: PRT
<213> ORGANISM: Artificial Sequence
<220> FEATURE:
<223> OTHER INFORMATION: lipocalin mutein

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Trp Gly Leu Arg Glu Asp Lys Asp Pro
        35                  40                  45

Lys Lys Met Ala Ala Thr Ile Tyr Glu Leu Lys Glu Asp Lys Ser Tyr
    50                  55                  60

Asn Val Thr Asp Val Gln Phe Ile Glu Lys Lys Cys Asp Tyr Trp Ile
65                  70                  75                  80

Gly Thr Phe Val Pro Gly Ser Gln Pro Gly Glu Phe Thr Leu Gly Ala
                85                  90                  95

Ile Lys Ser Glu Pro Gly Gln Thr Ser Asn Leu Val Arg Val Val Ser
            100                 105                 110

Thr Asn Tyr Asn Gln His Ala Met Val Phe Phe Lys Glu Val Trp Gln
        115                 120                 125

Asn Arg Glu Leu Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 3
<211> LENGTH: 178
<212> TYPE: PRT
<213> ORGANISM: Artificial Sequence
<220> FEATURE:
<223> OTHER INFORMATION: lipocalin mutein

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Met Trp Leu Arg Glu Asp Lys Asp Pro
        35                  40                  45

Phe Lys Met Gly Ala Thr Ile Tyr Glu Leu Lys Glu Asp Lys Ser Tyr
    50                  55                  60

Asn Val Thr Trp Val Trp Phe Glu Ala Lys Lys Cys Asp Tyr Gly Ile
65                  70                  75                  80

Asn Thr Phe Val Pro Gly Ser Gln Pro Gly Glu Phe Thr Leu Gly Gly
                85                  90                  95

Ile Lys Ser Pro Pro Gly Met Thr Ser His Leu Val Arg Val Val Ser
            100                 105                 110
```

```
Thr Asn Tyr Asn Gln His Ala Met Val Phe Phe Lys Glu Val Phe Gln
        115                 120                 125

Asn Arg Glu Trp Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 4
<211> LENGTH: 178
<212> TYPE: PRT
<213> ORGANISM: Artificial Sequence
<220> FEATURE:
<223> OTHER INFORMATION: lipocalin mutein

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Thr Lys Met Gln Ala Thr Ile Tyr Glu Leu Lys Glu Asp Lys Ser Tyr
    50                  55                  60

Asn Val Thr Trp Val Tyr Phe Ser Glu Lys Lys Cys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Ser Ile Leu Val Arg Val Val Ser
            100                 105                 110

Thr Asn Tyr Asn Gln His Ala Met Val Phe Phe Lys Gly Val Ser Gln
        115                 120                 125

Asn Arg Glu Ile Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 5
<211> LENGTH: 178
<212> TYPE: PRT
<213> ORGANISM: Artificial Sequence
<220> FEATURE:
<223> OTHER INFORMATION: lipocalin mutein

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Ala Glu Leu Arg Glu Asp Lys Asp Pro
        35                  40                  45
```

```
Glu Lys Met Glu Ala Thr Ile Tyr Glu Leu Lys Glu Asp Lys Ser Tyr
    50                  55                  60

Asn Val Thr Asp Val Gly Phe Trp Gln Lys Lys Cys Ile Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Thr Thr Ser Ala Leu Val Arg Val Val Ser
            100                 105                 110

Thr Asn Tyr Asn Gln His Ala Met Val Phe Phe Lys Val Val Arg Gln
        115                 120                 125

Asn Arg Glu Trp Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 6
<211> LENGTH: 178
<212> TYPE: PRT
<213> ORGANISM: Artificial Sequence
<220> FEATURE:
<223> OTHER INFORMATION: lipocalin mutein

<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Trp Trp Leu Arg Glu Asp Lys Asp Pro
        35                  40                  45

Leu Lys Met Tyr Ala Thr Ile Tyr Glu Leu Lys Glu Asp Lys Ser Tyr
    50                  55                  60

Asn Val Thr His Val Met Phe Met Thr Lys Lys Cys Asp Tyr Thr Ile
65                  70                  75                  80

Arg Thr Phe Val Pro Gly Ser Gln Pro Gly Glu Phe Thr Leu Gly Asn
                85                  90                  95

Ile Lys Ser Ile Pro Gly Met Thr Ser Leu Leu Val Arg Val Val Ser
            100                 105                 110

Thr Asn Tyr Asn Gln His Ala Met Val Phe Phe Lys Phe Val Trp Gln
        115                 120                 125

Asn Arg Glu Trp Phe His Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 7
<211> LENGTH: 178
<212> TYPE: PRT
<213> ORGANISM: Artificial Sequence
<220> FEATURE:
<223> OTHER INFORMATION: lipocalin mutein
```

```
<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Thr Ile Tyr Glu Leu Lys Glu Asp Lys Ser Tyr
    50                  55                  60

Asn Val Thr Trp Val Tyr Phe Ser Glu Lys Arg Cys Asn Tyr His Ile
65                  70                  75                  80

Glu Thr Ser Val Pro Gly Ser Gln Pro Gly Glu Phe Thr Leu Gly Thr
                85                  90                  95

Ile Lys Ser Tyr Pro Gly Glu Thr Ser Ile Leu Val Arg Val Val Ser
            100                 105                 110

Thr Asn Tyr Asn Gln His Ala Met Val Phe Phe Lys Gly Val Ser Gln
        115                 120                 125

Asn Arg Glu Ile Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 8
<211> LENGTH: 178
<212> TYPE: PRT
<213> ORGANISM: Artificial Sequence
<220> FEATURE:
<223> OTHER INFORMATION: lipocalin mutein

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Arg Arg Glu Asp Lys Asn Pro
        35                  40                  45

Thr Lys Met Gln Ala Thr Ile Tyr Glu Leu Lys Glu Asp Lys Ser Tyr
    50                  55                  60

Asn Val Thr Trp Val Tyr Phe Ser Glu Lys Lys Cys Asn Tyr His Ile
65                  70                  75                  80

Glu Thr Ser Val Pro Gly Ser Gln Pro Gly Glu Phe Thr Leu Gly Thr
                85                  90                  95

Ile Lys Ser Tyr Pro Gly Glu Thr Ser Ile Leu Val Arg Val Val Ser
            100                 105                 110

Thr Asn Tyr Asn Gln His Ala Met Val Phe Phe Lys Gly Val Ser Gln
        115                 120                 125

Asn Arg Glu Ile Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

```
Asp Gly


<210> SEQ ID NO 9
<211> LENGTH: 178
<212> TYPE: PRT
<213> ORGANISM: Artificial Sequence
<220> FEATURE:
<223> OTHER INFORMATION: lipocalin mutein

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Thr Ile Tyr Glu Leu Lys Glu Asp Lys Ser Tyr
    50                  55                  60

Asp Val Thr Trp Val Tyr Leu Ser Glu Lys Lys Cys Asn Tyr His Ile
65                  70                  75                  80

Glu Thr Ser Val Pro Gly Ser Gln Pro Gly Glu Phe Thr Leu Gly Thr
                85                  90                  95

Ile Lys Ser Tyr Pro Gly Glu Thr Ser Ile Leu Val Arg Val Val Ser
            100                 105                 110

Thr Asn Tyr Asn Gln His Ala Met Val Phe Phe Lys Gly Met Ser Gln
        115                 120                 125

Asn Arg Glu Ile Phe Glu Ile Thr Leu Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 10
<211> LENGTH: 178
<212> TYPE: PRT
<213> ORGANISM: Artificial Sequence
<220> FEATURE:
<223> OTHER INFORMATION: lipocalin mutein

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asn Pro
        35                  40                  45

Thr Lys Met Gln Ala Thr Ile Tyr Glu Leu Lys Glu Asp Lys Ser Tyr
    50                  55                  60

Asn Ala Thr Trp Val Tyr Leu Ser Glu Lys Lys Cys Asn Tyr His Ile
65                  70                  75                  80

Glu Thr Ser Val Pro Gly Ser Gln Pro Gly Glu Phe Thr Leu Gly Thr
                85                  90                  95

Thr Lys Ser Tyr Pro Gly Glu Thr Pro Ile Leu Val Arg Val Val Ser
            100                 105                 110
```

```
Thr Asn Tyr Asn Gln His Ala Met Val Phe Phe Lys Gly Val Ser Gln
        115                 120                 125

Asn Arg Glu Ile Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 11
<211> LENGTH: 178
<212> TYPE: PRT
<213> ORGANISM: Artificial Sequence
<220> FEATURE:
<223> OTHER INFORMATION: lipocalin mutein

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Ile Ile Tyr Glu Leu Lys Glu Asp Arg Ser Tyr
    50                  55                  60

Asn Val Thr Trp Val Tyr Phe Ser Glu Lys Lys Cys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Ile Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 12
<211> LENGTH: 178
<212> TYPE: PRT
<213> ORGANISM: Artificial Sequence
<220> FEATURE:
<223> OTHER INFORMATION: lipocalin mutein

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Pro Lys Met Gln Ala Thr Ile Tyr Glu Leu Lys Glu Asp Arg Ser Tyr
```

```
    50                  55                  60

Asn Val Thr Trp Val Tyr Phe Ser Glu Lys Lys Cys Asn Tyr His Ile
65                  70                  75                  80

Glu Thr Ser Val Pro Gly Ser Gln Pro Gly Glu Phe Thr Leu Gly Thr
                85                  90                  95

Ile Gln Ser His Pro Gly Glu Thr Pro Ile Leu Val Arg Val Val Ser
            100                 105                 110

Thr Asn Tyr Asn Gln His Ala Met Val Phe Phe Lys Gly Met Gly Gln
        115                 120                 125

Asn Arg Glu Ile Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 13
<211> LENGTH: 178
<212> TYPE: PRT
<213> ORGANISM: Artificial Sequence
<220> FEATURE:
<223> OTHER INFORMATION: lipocalin mutein

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Glu Glu Leu Arg Glu Asp Lys Asp Pro
        35                  40                  45

Gln Lys Met Glu Ala Thr Ile Tyr Glu Leu Lys Glu Asp Lys Ser Tyr
    50                  55                  60

Asn Val Thr Asp Val Gly Phe Ser Glu Lys Lys Cys Ile Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Ala Leu Val Arg Val Val Ser
            100                 105                 110

Thr Asn Tyr Asn Gln His Ala Met Val Phe Phe Lys Val Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 14
<211> LENGTH: 178
<212> TYPE: PRT
<213> ORGANISM: Artificial Sequence
<220> FEATURE:
<223> OTHER INFORMATION: lipocalin mutein

<400> SEQUENCE: 14
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Ala Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Lys Cys Met Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Ala Leu Val Arg Val Val Ser
            100                 105                 110

Thr Asn Tyr Asn Gln His Ala Met Val Phe Phe Lys Leu Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 15
<211> LENGTH: 178
<212> TYPE: PRT
<213> ORGANISM: Artificial Sequence
<220> FEATURE:
<223> OTHER INFORMATION: lipocalin mutein

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Ala Asn Asp Arg Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Ser Arg Lys Lys Cys Ile Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Thr Thr Ser Gly Leu Val Arg Val Val Ser
            100                 105                 110

Thr Asn Tyr Asn Gln His Ala Met Val Phe Phe Lys Val Val Gly Gln
        115                 120                 125

Asn Arg Glu Ser Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

```
Asp Gly


<210> SEQ ID NO 16
<211> LENGTH: 178
<212> TYPE: PRT
<213> ORGANISM: Artificial Sequence
<220> FEATURE:
<223> OTHER INFORMATION: lipocalin mutein

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Glu Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Lys Cys Met Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Gly Leu Val Arg Val Val Ser
            100                 105                 110

Thr Asn Tyr Asn Gln His Ala Met Val Phe Phe Lys Val Val Arg Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 17
<211> LENGTH: 178
<212> TYPE: PRT
<213> ORGANISM: Artificial Sequence
<220> FEATURE:
<223> OTHER INFORMATION: lipocalin mutein

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Val Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Arg Cys Met Tyr Val Thr
65                  70                  75                  80

His Thr Phe Val Pro Gly Ser Gln Pro Gly Glu Phe Thr Leu Gly Asn
                85                  90                  95

Ile Glu Ser Tyr Pro Gly Val Thr Ser Ala Leu Val Arg Val Val Ser
            100                 105                 110

Thr Asp Tyr Asn Gln His Ala Met Val Phe Val Lys Leu Val Lys Gln
```

```
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 18
<211> LENGTH: 178
<212> TYPE: PRT
<213> ORGANISM: Artificial Sequence
<220> FEATURE:
<223> OTHER INFORMATION: lipocalin mutein

<400> SEQUENCE: 18

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Ala Asn Asp Val Leu Arg Asp Asp Asn Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Lys Cys Met Tyr Val Val
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Ala Leu Val Arg Val Val Ser
            100                 105                 110

Thr Asn Tyr Asn Gln His Ala Met Val Phe Phe Lys Leu Val Lys Gln
        115                 120                 125

Asn Arg Glu Leu Phe Glu Val Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 19
<211> LENGTH: 178
<212> TYPE: PRT
<213> ORGANISM: Artificial Sequence
<220> FEATURE:
<223> OTHER INFORMATION: lipocalin mutein

<400> SEQUENCE: 19

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Thr Leu Arg Glu Asp Lys Asp Pro
        35                  40                  45

Glu Lys Met Glu Ala Thr Ile Tyr Glu Leu Lys Glu Asp Lys Ser Tyr
    50                  55                  60
```

```
Asn Val Thr Asp Val Gly Leu Val Gln Lys Lys Cys Met Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Ala Leu Val Arg Val Val Ser
            100                 105                 110

Thr Asn Tyr Asn Gln His Ala Met Val Phe Val Lys Leu Val Lys Gln
        115                 120                 125

Ser Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 20
<211> LENGTH: 178
<212> TYPE: PRT
<213> ORGANISM: Artificial Sequence
<220> FEATURE:
<223> OTHER INFORMATION: lipocalin mutein

<400> SEQUENCE: 20

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Thr Leu Arg Lys Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Lys Cys Met Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Ala Leu Val Arg Val Val Ser
            100                 105                 110

Thr Asn Tyr Asn Gln His Ala Met Val Phe Val Lys Leu Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 21
<211> LENGTH: 178
<212> TYPE: PRT
<213> ORGANISM: Artificial Sequence
<220> FEATURE:
<223> OTHER INFORMATION: lipocalin mutein

<400> SEQUENCE: 21
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Ala Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Lys Cys Met Tyr Val Ile
65                  70                  75                  80

His Thr Phe Val Pro Gly Ser Gln Pro Gly Glu Phe Thr Leu Gly Asn
                85                  90                  95

Ile Lys Ser Tyr Pro Gly Val Thr Ser Ala Leu Ile Arg Val Val Asn
            100                 105                 110

Thr Asn Tyr Asn Gln His Ala Met Val Phe Val Lys Leu Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 22
<211> LENGTH: 178
<212> TYPE: PRT
<213> ORGANISM: Artificial Sequence
<220> FEATURE:
<223> OTHER INFORMATION: lipocalin mutein

<400> SEQUENCE: 22

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Asp Ala Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Leu Val Gln Lys Lys Cys Met Tyr Val Ile
65                  70                  75                  80

His Thr Phe Val Pro Gly Gly Gln Pro Gly Glu Phe Thr Leu Gly Asn
                85                  90                  95

Ile Lys Ser Tyr Pro Gly Val Thr Ser Ala Leu Val Arg Val Val Ser
            100                 105                 110

Thr Asn Tyr Asn Gln His Ala Met Val Phe Val Lys Leu Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 23
<211> LENGTH: 178
<212> TYPE: PRT
<213> ORGANISM: Artificial Sequence
<220> FEATURE:
<223> OTHER INFORMATION: lipocalin mutein

<400> SEQUENCE: 23

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Lys Ile Tyr Glu Leu Lys Glu Asp Arg Ser Tyr
    50                  55                  60

Asn Val Thr Trp Val Tyr Phe Ala Asp Lys Lys Cys Asn Tyr His Ile
65                  70                  75                  80

Glu Thr Phe Val Pro Gly Ser Gln Pro Gly Glu Phe Thr Leu Gly Leu
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Ile Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 24
<211> LENGTH: 178
<212> TYPE: PRT
<213> ORGANISM: Artificial Sequence
<220> FEATURE:
<223> OTHER INFORMATION: lipocalin mutein

<400> SEQUENCE: 24

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Lys Ile Tyr Glu Leu Lys Glu Asp Arg Ser Tyr
    50                  55                  60

Asn Val Thr Trp Val Tyr Phe Ala Glu Lys Lys Cys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125
```

```
Asn Arg Glu Ile Phe Glu Ile Ile Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 25
<211> LENGTH: 178
<212> TYPE: PRT
<213> ORGANISM: Artificial Sequence
<220> FEATURE:
<223> OTHER INFORMATION: lipocalin mutein

<400> SEQUENCE: 25

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Lys Ile Tyr Glu Leu Lys Glu Asp Arg Ser Tyr
    50                  55                  60

Asn Val Thr Trp Val Tyr Phe Ala Asp Lys Lys Cys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Ile Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 26
<211> LENGTH: 178
<212> TYPE: PRT
<213> ORGANISM: Artificial Sequence
<220> FEATURE:
<223> OTHER INFORMATION: lipocalin mutein

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Lys Ile Tyr Glu Leu Lys Glu Asp Arg Ser Tyr
    50                  55                  60
```

```
Asn Val Thr Trp Val Tyr Phe Ala Asp Lys Lys Cys Arg Tyr His Ile
65                  70                  75                  80

Glu Thr Phe Val Pro Gly Ser Gln Pro Gly Glu Phe Thr Leu Gly Thr
                85                  90                  95

Ile Lys Ser His Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Ile Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 27
<211> LENGTH: 178
<212> TYPE: PRT
<213> ORGANISM: Artificial Sequence
<220> FEATURE:
<223> OTHER INFORMATION: lipocalin mutein

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Cys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 28
<211> LENGTH: 178
<212> TYPE: PRT
<213> ORGANISM: Artificial Sequence
<220> FEATURE:
<223> OTHER INFORMATION: lipocalin mutein

<400> SEQUENCE: 28

Gln Asp Ser Thr Ser Asp Leu Ile Pro Ala Pro Pro Leu Ser Lys Val
```

```
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Ile Ile Tyr Glu Leu Lys Glu Asp Arg Ser Tyr
    50                  55                  60

Asn Val Thr Trp Val Tyr Phe Ser Glu Lys Lys Cys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Met Ser
            100                 105                 110

Thr Asn Tyr Asn Gln His Ala Met Val Phe Phe Lys Gly Val Asn Gln
        115                 120                 125

Asn Arg Glu Ile Phe Glu Ile Ile Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 29
<211> LENGTH: 177
<212> TYPE: PRT
<213> ORGANISM: Artificial Sequence
<220> FEATURE:
<223> OTHER INFORMATION: lipocalin mutein

<400> SEQUENCE: 29

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Asp Val Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Arg Leu Met Tyr Val Thr
65                  70                  75                  80

His Thr Phe Val Pro Gly Ser Gln Pro Gly Glu Phe Thr Leu Gly Asn
                85                  90                  95

Ile Glu Ser Tyr Pro Gly Val Thr Ser Ala Leu Val Arg Val Val Ser
            100                 105                 110

Thr Asp Tyr Asn Gln His Ala Met Val Phe Val Lys Leu Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ile Asp
                165                 170                 175

Gly
```

```
<210> SEQ ID NO 30
<211> LENGTH: 177
<212> TYPE: PRT
<213> ORGANISM: Artificial Sequence
<220> FEATURE:
<223> OTHER INFORMATION: lipocalin mutein

<400> SEQUENCE: 30

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Asp Val Leu Arg Glu Asp Lys Asp Pro
        35                  40                  45

Glu Lys Met Glu Ala Thr Ile Tyr Glu Leu Lys Glu Asp Lys Ser Tyr
    50                  55                  60

Asn Val Thr Asp Val Gly Phe Val Gln Lys Arg Tyr Met Tyr Val Thr
65                  70                  75                  80

His Thr Phe Val Pro Gly Ser Gln Pro Gly Glu Phe Thr Leu Gly Asn
                85                  90                  95

Ile Glu Ser Tyr Pro Gly Val Thr Ser Ala Leu Val Arg Val Val Ser
            100                 105                 110

Thr Asp Tyr Asn Gln His Ala Met Val Phe Val Lys Leu Val Lys Gln
        115                 120                 125

Asn Arg Glu Leu Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ile Asp
                165                 170                 175

Gly


<210> SEQ ID NO 31
<211> LENGTH: 178
<212> TYPE: PRT
<213> ORGANISM: Artificial Sequence
<220> FEATURE:
<223> OTHER INFORMATION: lipocalin mutein

<400> SEQUENCE: 31

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Arg Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125
```

```
Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Phe Ile
                165                 170                 175

Asp Gly


<210> SEQ ID NO 32
<211> LENGTH: 178
<212> TYPE: PRT
<213> ORGANISM: Artificial Sequence
<220> FEATURE:
<223> OTHER INFORMATION: lipocalin mutein

<400> SEQUENCE: 32

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Met Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Tyr Ile
                165                 170                 175

Asp Gly


<210> SEQ ID NO 33
<211> LENGTH: 178
<212> TYPE: PRT
<213> ORGANISM: Artificial Sequence
<220> FEATURE:
<223> OTHER INFORMATION: lipocalin mutein

<400> SEQUENCE: 33

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Leu Asn Tyr His Ile
```

```
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Trp Ile
                165                 170                 175

Asp Gly


<210> SEQ ID NO 34
<211> LENGTH: 178
<212> TYPE: PRT
<213> ORGANISM: Artificial Sequence
<220> FEATURE:
<223> OTHER INFORMATION: lipocalin mutein

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Ile Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Glu Ile
                165                 170                 175

Asp Gly


<210> SEQ ID NO 35
<211> LENGTH: 178
<212> TYPE: PRT
<213> ORGANISM: Artificial Sequence
<220> FEATURE:
<223> OTHER INFORMATION: lipocalin mutein

<400> SEQUENCE: 35

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Val Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Tyr Ile
                165                 170                 175

Asp Gly


<210> SEQ ID NO 36
<211> LENGTH: 178
<212> TYPE: PRT
<213> ORGANISM: Artificial Sequence
<220> FEATURE:
<223> OTHER INFORMATION: lipocalin mutein

<400> SEQUENCE: 36

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Arg Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Trp Ile
                165                 170                 175

Asp Gly
```

<210> SEQ ID NO 37
<211> LENGTH: 178
<212> TYPE: PRT
<213> ORGANISM: Artificial Sequence
<220> FEATURE:
<223> OTHER INFORMATION: lipocalin mutein

<400> SEQUENCE: 37

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Asn Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Leu Ile
                165                 170                 175

Asp Gly
```

<210> SEQ ID NO 38
<211> LENGTH: 178
<212> TYPE: PRT
<213> ORGANISM: Artificial Sequence
<220> FEATURE:
<223> OTHER INFORMATION: lipocalin mutein

<400> SEQUENCE: 38

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Arg Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
```

```
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Val Ile
                165                 170                 175

Asp Gly


<210> SEQ ID NO 39
<211> LENGTH: 178
<212> TYPE: PRT
<213> ORGANISM: Artificial Sequence
<220> FEATURE:
<223> OTHER INFORMATION: lipocalin mutein

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Lys Asn Tyr His Ile
65                  70                  75                  80

Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Asp Ile
                165                 170                 175

Asp Gly


<210> SEQ ID NO 40
<211> LENGTH: 178
<212> TYPE: PRT
<213> ORGANISM: Artificial Sequence
<220> FEATURE:
<223> OTHER INFORMATION: lipocalin mutein

<400> SEQUENCE: 40

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Leu Leu Arg Glu Asp Lys Asp Pro
        35                  40                  45

Ile Lys Met Gln Ala Met Ile Tyr Glu Leu Lys Glu Asp Lys Ser Tyr
    50                  55                  60

Asn Val Thr Trp Val Tyr Phe Ala Asp Lys Lys Phe Asn Tyr His Ile
65                  70                  75                  80
```

```
Glu Thr Phe Val Pro Gly Ser Gln Pro Gly Glu Phe Thr Leu Gly Thr
                85                  90                  95

Ile Lys Ser Tyr Pro Gly Glu Thr Pro Ile Leu Val Arg Val Val Ser
            100                 105                 110

Thr Asn Tyr Asn Gln His Ala Met Val Phe Phe Lys Gly Val Asn Gln
        115                 120                 125

Asn Arg Glu Ile Phe Glu Ile Val Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Asp Ile
                165                 170                 175

Asp Gly


<210> SEQ ID NO 41
<211> LENGTH: 534
<212> TYPE: DNA
<213> ORGANISM: Artificial Sequence
<220> FEATURE:
<223> OTHER INFORMATION: nucleotide sequence of the mutein shown in SEQ
      ID NO: 2

<400> SEQUENCE: 41

caggactcca cctcagacct gatcccagcc ccacctctga gcaaggtccc tctgcagcag     60

aacttccagg acaaccaatt ccatgggaaa tggtatgtcg tgggcgaggc cggaaattgg    120

ggactgcgtg aggataagga tccgaaaaaa atggcagcga ccatttacga gttgaaagaa    180

gataaatcat ataacgtcac cgacgtgcaa tttatcgaga agaaatgcga ctactggatt    240

ggaacctttg tgccggggag ccagccgggc gagtttactt taggcgcaat taaaagtgag    300

ccgggccaaa catcaaattt ggtccgcgtc gtgagcacca actacaacca gcatgccatg    360

gtgttcttca aggaggtgtg gcagaaccgc gagctgtttt ggatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534


<210> SEQ ID NO 42
<211> LENGTH: 534
<212> TYPE: DNA
<213> ORGANISM: Artificial Sequence
<220> FEATURE:
<223> OTHER INFORMATION: nucleotide sequence of the mutein shown in SEQ
      ID NO: 3

<400> SEQUENCE: 42

caggactcca cctcagacct gatcccagcc ccacctctga gcaaggtccc tctgcagcag     60

aacttccagg acaaccaatt ccatgggaaa tggtatgtcg tgggcttcgc cggaaatatg    120

tggctgcgtg aggataagga tccgttcaaa atgggagcga ccatttacga gttgaaagaa    180

gataaatcat ataacgtcac ctgggtgtgg tttgaggcaa agaaatgcga ctacggaatt    240

aatacctttg tgccggggag ccagccgggc gagtttactt taggcggaat taaaagtcct    300

ccgggcatga catcacactt ggtccgcgtc gtgagcacca actacaacca gcatgccatg    360

gtgttcttca aggaggtgtt ccagaaccgc gagtggtttt ggatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 43
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 4

<400> SEQUENCE: 43

```
caggactcca cctcagacct gatcccagcc ccacctctga gcaaggtccc tctgcagcag     60

aacttccagg acaaccaatt ccatgggaaa tggtatgtcg tgggctgggc cggaaatacc    120

ctgctgcgtg aggataagga tccgaccaaa atgcaagcga ccatttacga gttgaaagaa    180

gataaatcat ataacgtcac ctgggtgtac tttagcgaga agaaatgcaa ttaccacatt    240

gagacctttg tgccggggag ccagccgggc gagtttactt taggcaccat taaaagttac    300

ccgggcgaga catcaatctt ggtccgcgtc gtgagcacca actacaacca gcatgccatg    360

gtgttcttca agggagtgag ccagaaccgc gagatctttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 44
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 5

<400> SEQUENCE: 44

```
caggactcca cctcagacct gatcccagcc ccacctctga gcaaggtccc tctgcagcag     60

aacttccagg acaaccaatt ccatgggaaa tggtatgtcg tgggccgtgc cggaaatgca    120

gagctgcgtg aggataagga tccggagaaa atggaggcga ccatttacga gttgaaagaa    180

gataaatcat ataacgtcac cgacgtggga ttttggcaaa agaaatgcat ctacgttatt    240

cacacctttg tgccggggag ccagccgggc gagtttactt taggcaatat taaaagttac    300

ccgggcacca catcagcatt ggtccgcgtc gtgagcacca actacaacca gcatgccatg    360

gtgttcttca aggttgtgcg tcagaaccgc gagtggtttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 45
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 6

<400> SEQUENCE: 45

```
caggactcca cctcagacct gatcccagcc ccacctctga gcaaggtccc tctgcagcag     60

aacttccagg acaaccaatt ccatgggaaa tggtatgtcg tgggcatcgc cggaaattgg    120

tggctgcgtg aggataagga tccgctgaaa atgtacgcga ccatttacga gttgaaagaa    180

gataaatcat ataacgtcac ccacgtgatg tttatgacta agaaatgcga ctacaccatt    240

cgtacctttg tgccggggag ccagccgggc gagtttactt taggcaatat taaaagtatc    300
```

```
ccgggcatga catcactgtt ggtccgcgtc gtgagcacca actacaacca gcatgccatg    360

gtgttcttca agttcgtgtg gcagaaccgc gagtggtttc acatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 46
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 7

<400> SEQUENCE: 46

```
caggactcca cctcagacct gatcccagcc ccacctctga gcaaggtccc tctgcagcag     60

aacttccagg acaaccaatt ccatgggaaa tggtatgtcg tgggctgggc cggaaatacc    120

ctgctgcgcg aggataagga tccgatcaaa atgcaagcga ccatttacga gttgaaggaa    180

gataaatcat ataacgtcac ctgggtgtac tttagcgaga agagatgcaa ttaccacatt    240

gagacctctg tgccggggag ccagccgggc gagtttactt taggcaccat taaaagttac    300

ccgggcgaga catcaatctt ggtccgcgtc gtgagcacca actacaacca gcatgccatg    360

gtgttcttca agggagtgag ccagaaccgc gagatctttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 47
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO:8

<400> SEQUENCE: 47

```
caggactcca cctcagacct gatcccagcc ccacctctga gcaaggtccc tctgcagcag     60

aacttccagg acaaccaatt ccatgggaaa tggtatgtcg tgggctgggc cggaaatacc    120

ctgcggcgtg aggataagaa tccgaccaaa atgcaagcga ccatttacga gttgaaagaa    180

gataaatcat ataacgtcac ctgggtgtac tttagcgaga agaaatgcaa ttaccacatt    240

gagacctctg tgccggggag ccagccgggc gagtttactt taggcaccat taaaagttac    300

ccgggcgaga catcaatctt ggtccgcgtc gtgagcacca actacaacca gcatgccatg    360

gtgttcttca agggagtgag ccagaaccgc gagatctttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 48
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 9

<400> SEQUENCE: 48

```
caggactcca cctcagacct gatcccagcc ccacctctga gcaaggtccc tctgcagcag     60
```

aacttccagg acaaccaatt ccatgggaaa tggtatgtcg tgggctgggc cggaaatacc 120
ctgctgcgtg aggataagga tccgatcaaa atgcaagcga ccatttacga gttgaaagaa 180
gataagtcat atgacgtcac ctgggtgtac cttagcgaga agaaatgcaa ttaccacatt 240
gagacctctg tgccggggag ccagccgggc gagtttactt taggcaccat taaaagttac 300
ccgggcgaga catcaatctt ggtccgcgtc gtgagtacca actacaacca gcatgccatg 360
gtgttcttca agggaatgag ccagaaccgc gagatctttg agatcacact gtacgggcgc 420
acgaaagaac tggcaagcga gctgaaggaa aattttatcc gcttttccaa atctctgggc 480
ctccctgaaa accacatcgt cttccctgtc ccaatcgacc agtgtatcga cggc 534

<210> SEQ ID NO 49
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 10

<400> SEQUENCE: 49
caggactcca cctcagacct gatcccagcc ccacctctga gcaaggtccc tctgcagcag 60
aacttccagg acaaccaatt ccatgggaaa tggtatgtcg tgggctgggc cggaaatacc 120
ctgctgcgtg aggataagaa tccgaccaaa atgcaagcga ccatttacga gttgaaagaa 180
gataaatcat ataacgccac ctgggtgtac cttagcgaga agaaatgcaa ttaccacatt 240
gagacctctg tgccggggag ccagccgggc gagtttacct taggcaccac taaaagttac 300
ccgggcgaga caccaatcct ggtccgcgtc gtgagcacca actacaacca gcatgccatg 360
gtgttcttca agggagtgag ccagaaccgc gagatctttg agatcacact gtacgggcgc 420
acgaaagaac tgacaagcga gttgaaggaa aattttatcc gcttttccaa atctctgggc 480
ctccctgaaa accacatcgt cttccctgtc ccaatcgacc agtgtatcga cggc 534

<210> SEQ ID NO 50
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 11

<400> SEQUENCE: 50
caggactcca cctcagacct gatcccagcc ccacctctga gcaaggtccc tctgcagcag 60
aacttccagg acaaccaatt ccatgggaaa tggtatgtcg tgggctgggc cggaaatacc 120
ctgctgcgtg aggataagga tccgatcaaa atgcaagcga tcatttacga gttgaaagaa 180
gatagatcat ataacgtcac ctgggtgtac tttagcgaaa agaaatgcaa ttaccacatt 240
gagacctttg tgccggggag ccagccgggc gagtttactt taggcaccat taaaagttac 300
ccgggcgaga caccaatctt ggtccgcgtc gtgagcacca actacaacca gcatgccatg 360
gtgttcttca agggagtgaa ccagaaccgc gagatctttg agatcatact gtacgggcgc 420
acgaaagaac tgacaaacga actgaaggaa aattttatcc gcttttccaa atctctgggc 480
ctccctgaaa accacatcgt cttccctgtc ccaatcgacc agtgtatcga cggc 534

<210> SEQ ID NO 51
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 12

<400> SEQUENCE: 51

```
caggactcca cctcagacct gatcccagcc ccacctctga gcaaggtccc tctgcagcag     60

aacttccagg acaaccaatt ccatgggaaa tggtatgtcg tgggctgggc cggaaatacc    120

ctgctgcgtg aggataagga tccgcccaaa atgcaagcga ccatttacga gttgaaagaa    180

gatagatcgt ataacgtcac ctgggtgtac tttagcgaga agaaatgcaa ttaccacatt    240

gagacctctg tgccggggag ccagccgggc gagtttactt taggcaccat tcaaagtcac    300

ccgggcgaga caccaatctt agtccgcgtc gtgagcacca actacaacca gcatgccatg    360

gtgttcttca agggaatggg ccagaaccgc gagatctttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 52
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 13

<400> SEQUENCE: 52

```
caggactcca cctcagacct gatcccagcc ccacctctga gcaaggtccc tctgcagcag     60

aacttccagg acaaccaatt ccatgggaaa tggtacgtgg tagggagggc cggaaatgag    120

gagctgcgtg aggataagga tccgcagaaa atggaggcga ccatttacga gttgaaagaa    180

gataaatcat ataacgtcac cgatgtgggg ttttcggaga agaaatgcat ttacgttatt    240

catacctttg tgccggggag ccagccgggc gagtttactt taggcaatat taaaagttat    300

ccgggcgtga catcagcgtt ggtccgcgtc gtgagcacca actacaacca gcatgccatg    360

gtgttcttca aggtggtgaa gcagaaccgc gagttgtttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 53
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 14

<400> SEQUENCE: 53

```
caggactcca cctcagacct gatcccagcc ccacctctga gcaaggtccc tctgcagcag     60

aacttccagg acaaccaatt ccatgggaaa tggtacgtgg tagggagggc cggaaatgat    120

gcgctgcgtg aggataagga tccggagaaa atggaggcga ccatttacga gttgaaagaa    180

gataaatcat ataacgtcac cgatgtgggg tttgtgcaga agaaatgcat gtacgtgatt    240

catacctttg tgccggggag ccagccgggc gagtttactt taggcaatat taaaagttat    300

ccgggcgtga catcagcttt ggtccgcgtc gtgagcacca actacaacca gcatgccatg    360

gtgttcttca agctggtgaa gcagaaccgc gagttgtttg agatcacact gtacgggcgc    420

acgaaagaac tgacaagcga gctgaaggaa aattttatcc gcttttccaa atctctgggc    480
```

ctccctgaaa accacatcgt cttccctgtc ccaatcgacc agtgtatcga cggc 534

<210> SEQ ID NO 54
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 15

<400> SEQUENCE: 54
caggactcca cctcagacct gatcccagcc ccacctctga gcaaggtccc tctgcagcag 60
aacttccagg acaaccaatt ccatgggaaa tggtacgtgg tagggagggc cgcaaatgat 120
aggctgcgtg aggataagga tccggagaaa atggaggcga ccatttacga gttgaaagaa 180
gataaatcat ataacgtcac cgatgtgggg ttttcgcgga agaaatgcat ttacgttatt 240
catacctttg tgccggggag ccagccgggc gagtttactt taggcaatat taaaagttat 300
ccgggcacga catcaggttt ggtccgcgtc gtgagcacca actacaacca gcatgccatg 360
gtgttcttca aggtggtggg gcagaaccgc gagtcgtttg agatcacact gtacgggcgc 420
acgaaagaac tgacaagcga gctgaaggaa aattttatcc gcttttccaa atctctgggc 480
ctccctgaaa accacatcgt cttccctgtc ccaatcgacc agtgtatcga cggc 534

<210> SEQ ID NO 55
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 16

<400> SEQUENCE: 55
caggactcca cctcagacct gatcccagcc ccacctctga gcaaggtccc tctgcagcag 60
aacttccagg acaaccaatt ccatgggaaa tggtacgtgg tagggagggc cggaaatgat 120
gagctgcgtg aggataagga tccggagaaa atggaggcga ccatttacga gttgaaagaa 180
gataaatcat ataacgtcac cgatgtgggt tttgtgcaga agaaatgcat gtacgttatt 240
catacctttg tgccggggag ccagccgggc gagtttactt taggcaatat taaaagttat 300
ccgggcgtga catcaggttt ggtccgcgtc gtgagcacca actacaacca gcatgccatg 360
gtgttcttca aggttgtgag gcagaaccgc gagttgtttg agatcacact gtacgggcgc 420
acgaaagaac tgacaagcga gctgaaggaa aattttatcc gcttttccaa atctctgggc 480
ctccctgaaa accacatcgt cttccctgtc ccaatcgacc agtgtatcga cggc 534

<210> SEQ ID NO 56
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 17

<400> SEQUENCE: 56
caggactcca cctcagacct gatcccagcc ccacctctga gcaaggtccc tctgcagcag 60
aacttccagg acaaccaatt ccatgggaaa tggtacgtgg tagggagggc cggaaatgat 120
gtgctgcgtg aggataagga cccggagaaa atggaggcga ccatttacga gttgaaagaa 180
gataaatcat ataacgtcac cgatgtgggg tttgtgcaga agagatgcat gtacgtgact 240
catacctttg tgccggggag ccagccgggc gagtttactt taggcaacat tgaaagttat 300
ccgggcgtga catcagcttt ggtccgcgtc gtgagcaccg actacaacca gcatgccatg 360
gtgttcgtca agctggtgaa gcagaaccgc gagttgtttg agatcacact gtacgggcgc 420
acgaaagagc tgacaagcga gctgaaggaa aattttatcc gcttttccaa atctctgggc 480
ctccctgaaa accacatcgt cttccctgtc ccaatcgacc agtgtatcga cggc 534

<210> SEQ ID NO 57
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 18

<400> SEQUENCE: 57
caggactcca cctcagacct gatcccagcc ccacctctga gcaaggtccc tctgcagcag 60
aacttccagg acaaccaatt ccatgggaaa tggtacgtgg tagggagggc tgcaaatgat 120
gtgctacgtg atgataatga tccggagaaa atggaggcga ccatttacga gttgaaagaa 180
gataaatcat ataacgtcac cgatgtgggg tttgtgcaga agaaatgcat gtatgtggtt 240
catacctttg tgccggggag ccagccgggc gagtttactt taggcaatat taaaagttat 300
ccgggcgtga catcagcttt ggtccgcgtc gtgagcacca actacaacca gcatgctatg 360
gtgttcttca agctggtgaa gcagaaccgc gagttgtttg aggtcacact gtacgggcgc 420
acgaaagaac tgacaagcga gctgaaggaa aattttatcc gcttttccaa atctctgggc 480
ctccctgaaa accacatcgt cttccctgtc ccaatcgacc agtgtatcga cggc 534

<210> SEQ ID NO 58
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 19

<400> SEQUENCE: 58
caggactcca cctcagacct gatcccagcc ccacctctga gcaaggtccc tctgcagcag 60
aacttccagg acaaccaatt ccatgggaaa tggtacgtgg tagggagggc cggaaatgat 120
acgctgcgtg aggataagga tccggagaaa atggaggcga ccatttacga gttgaaagaa 180
gataaatcat ataacgtcac cgatgtgggg cttgtgcaga agaaatgcat gtacgtgatt 240
catacctttg tgccggggag ccagccgggc gagtttactt taggcaatat taagagttat 300
ccgggcgtga catcagcttt ggtccgcgtc gtgagcacca actacaacca gcatgccatg 360
gtgttcgtca agctggtgaa gcagagccgc gagttgtttg agatcacact gtacgggcgc 420
acgaaagaac tgacaagcga gctgaaggaa aattttatcc gcttttccaa atctctgggc 480
ctccctgaaa accacatcgt cttccctgtc ccaatcgacc agtgtatcga cggc 534

<210> SEQ ID NO 59
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 20

<400> SEQUENCE: 59

```
caggactcca cctcagacct gatcccagcc ccacctctga gcaaggtccc tctgcagcag     60

aacttccagg acaaccaatt ccatgggaaa tggtacgtgg tagggagggc cggaaatgat    120

acgctgcgta aggataagga tccggagaag atggaggcga ccatatacga gttgaaagaa    180

gataaatcat ataacgtcac cgatgtgggg tttgtgcaga agaaatgcat gtacgtgatt    240

catacctttg taccggggag ccagccgggc gagtttactt taggcaatat taaaagttat    300

ccgggcgtaa catcagcttt ggtccgcgtc gtgagcacca actacaacca gcatgccatg    360

gtgttcgtca agctggtgaa gcagaaccgc gagttgtttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 60
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 21

<400> SEQUENCE: 60

```
caggactcca cctcagacct gatcccagcc ccacctctga gcaaggtccc tctgcagcag     60

aacttccagg acaaccaatt ccatgggaaa tggtacgtgg tagggagggc cggaaatgat    120

gcgctgcgtg aggataagga tccggagaaa atggaggcga ccatttacga gttgaaagaa    180

gataaatcat ataacgtcac cgatgtgggg tttgtgcaga agaaatgcat gtacgtgatt    240

catacctttg tgccggggag ccagccgggc gagtttactt taggcaatat taaaagttat    300

ccgggcgtga catcagcttt gatccgcgtc gtgaacacca actacaacca gcatgccatg    360

gtgttcgtca agctggtgaa gcagaaccgc gagttgtttg agatcacact gtacgggcgc    420

acgaaagaac tgacgagcga gctgaaggaa aattttatcc gcttttccaa atctctgggc    480

ctccctgaaa accacatcgt cttccctgtc ccaatcgacc agtgtatcga cggc          534
```

<210> SEQ ID NO 61
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 22

<400> SEQUENCE: 61

```
caggactcca cctcagacct gatcccagcc ccacctctga gcaaggtccc tctgcagcag     60

aacttccagg acaaccaatt ccatgggaaa tggtacgtgg tagggagggc cggaaatgat    120

gcgctgcgtg aggataagga tccggagaaa atggaggcga ccatttacga gttgaaagaa    180

gataaatcat ataacgtcac cgatgtgggg cttgtgcaga agaaatgcat gtacgtgatt    240

catacctttg tgccgggggg ccagccgggc gagtttactt taggcaatat taaaagttat    300

ccgggcgtga catcagctct ggtccgcgtc gtgagcacca actacaacca gcatgccatg    360

gtgttcgtca agctggtgaa gcagaaccgc gagttgtttg agatcacact gtacgggcgc    420

acgaaagaac tgacaagcga gctgaaggaa aattttatcc gcttttccaa atctctgggc    480

ctccctgaaa accacatcgt cttccctgtc ccaatcgacc agtgtatcga cggc          534
```

<210> SEQ ID NO 62

<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 23

<400> SEQUENCE: 62

```
caggactcca cctcagacct gatcccagcc ccacctctga gcaaggtccc tctgcagcag      60

aacttccagg acaaccaatt ccatgggaaa tggtacgttg tcgggtgggc cggaaatacg     120

ctgctgcgtg aggataagga tccgattaaa atgcaggcga agatttacga gttgaaagaa     180

gataggtcat ataacgtcac ctgggtgtat tttgcggata agaaatgcaa ttaccatatt     240

gagacctttg tgccggggag ccagccgggc gagtttactt taggcttgat taaaagttat     300

ccgggcgaga caccgatttt ggtccgcgtc gtgagcacca actacaacca gcatgccatg     360

gtgttcttca agggggtgaa tcagaaccgc gagatttttg agatcattct gtacgggcgc     420

acgaaagaac tgacaaacga actgaaggaa aattttatcc gcttttccaa atctctgggc     480

ctccctgaaa accacatcgt cttccctgtc ccaatcgacc agtgtatcga cggc           534
```

<210> SEQ ID NO 63
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 24

<400> SEQUENCE: 63

```
caggactcca cctcagacct gatcccagcc ccacctctga gcaaggtccc tctgcagcag      60

aacttccagg acaaccaatt ccatgggaaa tggtacgttg tcgggtgggc cggaaatacg     120

cttctgcgtg aggataagga tccgattaaa atgcaggcga agatttacga gttgaaagaa     180

gataggtcat ataacgtcac ctgggtgtat tttgctgaga agaaatgcaa ttaccatatt     240

gagacctttg tgccggggag ccagccgggc gagtttactt taggcacgat taaaagttat     300

ccgggcgaga cacctatttt ggtccgcgtc gtgagcacca actacaacca gcatgccatg     360

gtgttcttca agggtgtgaa tcagaaccgc gagatttttg agatcattct gtacgggcgc     420

acgaaagaac tgacaaacga actgaaggaa aattttatcc gcttttccaa atctctgggc     480

ctccctgaaa accacatcgt cttccctgtc ccaatcgacc agtgtatcga cggc           534
```

<210> SEQ ID NO 64
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 25

<400> SEQUENCE: 64

```
caggactcca cctcagacct gatcccagcc ccacctctga gcaaggtccc tctgcagcag      60

aacttccagg acaaccaatt ccatgggaaa tggtacgttg tcgggtgggc cggaaatacg     120

cttctgcgtg aggataagga tccgattaaa atgcaggcga agatttacga gttgaaagaa     180

gataggtcat ataacgtcac ctgggtgtat tttgcggata agaaatgcaa ttaccatatt     240

gagacctttg tgccggggag ccagccgggc gagtttactt taggcacgat taaaagttat     300

ccgggcgaga cacctatttt ggtccgcgtc gtgagcacca actacaacca gcatgccatg     360
```

```
gtgttcttca agggggtgaa tcagaaccgc gagatttttg agatcattct gtacgggcgc    420

acgaaagaac tgacaaacga actgaaggaa aattttatcc gcttttccaa atctctgggc    480

ctccctgaaa accacatcgt cttccctgtc ccaatcgacc agtgtatcga cggc          534


<210> SEQ ID NO 65
<211> LENGTH: 534
<212> TYPE: DNA
<213> ORGANISM: Artificial Sequence
<220> FEATURE:
<223> OTHER INFORMATION: nucleotide sequence of the mutein shown in SEQ
      ID NO: 26

<400> SEQUENCE: 65

caggactcca cctcagacct gatcccagcc ccacctctga gcaaggtccc tctgcagcag     60

aacttccagg acaaccaatt ccatgggaaa tggtacgttg tcgggtgggc cggaaatacg    120

cttctgcgtg aggataagga tccgattaaa atgcaggcga agatttacga gttgaaagaa    180

gataggtcat ataacgtcac ctgggtgtat tttgcggata agaaatgcag gtaccatatt    240

gagacctttg tgccggggag ccagccgggc gagtttactt taggcacgat taaaagtcat    300

ccgggcgaga cacctatttt ggtccgcgtc gtgagcacca actacaacca gcatgccatg    360

gtgttcttca agggtgtgaa tcagaaccgc gagatttttg agatcattct gtacgggcgc    420

acgaaagaac tgacaaacga actgaaggaa aattttatcc gcttttccaa atctctgggc    480

ctccctgaaa accacatcgt cttccctgtc ccaatcgacc agtgtatcga cggc          534


<210> SEQ ID NO 66
<211> LENGTH: 534
<212> TYPE: DNA
<213> ORGANISM: Artificial Sequence
<220> FEATURE:
<223> OTHER INFORMATION: nucleotide sequence of the mutein shown in SEQ
      ID NO: 27

<400> SEQUENCE: 66

caggactcca cctcagacct gatcccagcc ccacctctga gcaaggtccc tctgcagcag     60

aacttccagg acaaccaatt ccatgggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaatgcaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc agtgtatcga cggc          534


<210> SEQ ID NO 67
<211> LENGTH: 534
<212> TYPE: DNA
<213> ORGANISM: Artificial Sequence
<220> FEATURE:
<223> OTHER INFORMATION: nucleotide sequence of the mutein shown in SEQ
      ID NO: 28

<400> SEQUENCE: 67

caggactcca cctcagacct gatcccagcc ccacctctga gcaaggtccc tctgcagcag     60

aacttccagg acaaccaatt ccatgggaaa tggtatgtcg tgggctgggc cggaaatacc    120
```

```
ctgctgcgtg aggataagga tccgatcaaa atgcaagcga tcatttacga gttgaaagaa    180

gatagatcat ataacgtcac ctgggtgtac tttagcgaaa agaaatgcaa ttaccacatt    240

gagacctttg tgccggggag ccagccgggc gagtttactt taggcaccat taaaagttac    300

ccgggcgaga caccaatctt ggtccgcgtc atgagcacca actacaacca gcatgccatg    360

gtgttcttca agggagtgaa ccagaaccgc gagatctttg agatcatact gtacgggcgc    420

acgaaagaac tgacaaacga actgaaggaa aattttatcc gcttttccaa atctctgggc    480

ctccctgaaa accacatcgt cttccctgtc ccaatcgacc agtgtatcga cggc          534


<210> SEQ ID NO 68
<211> LENGTH: 531
<212> TYPE: DNA
<213> ORGANISM: Artificial Sequence
<220> FEATURE:
<223> OTHER INFORMATION: nucleotide sequence of the mutein shown in SEQ
      ID NO: 29

<400> SEQUENCE: 68

caggactcca cctcagacct gatcccagcc ccacctctga gcaaggtccc tctgcagcag     60

aacttccagg acaaccaatt ccaagggaaa tggtacgtgg tagggagggc cggaaatgat    120

gtgctgcgtg aggataagga cccggagaaa atggaggcga ccatttacga gttgaaagaa    180

gataaatcat ataacgtcac cgatgtgggg tttgtgcaga agagactgat gtacgtgact    240

catacctttg tgccggggag ccagccgggc gagtttactt taggcaacat tgaaagttat    300

ccgggcgtga catcagcttt ggtccgcgtc gtgagcaccg actacaacca gcatgccatg    360

gtgttcgtca agctggtgaa gcagaaccgc gagttgtttg agatcacact gtacgggcgc    420

acgaaagagc tgacaagcga gctgaaggaa aattttatcc gcttttccaa atctctgggc    480

ctccctgaaa accacatcgt cttccctgtc ccaatcgacc agatcgacgg c             531


<210> SEQ ID NO 69
<211> LENGTH: 531
<212> TYPE: DNA
<213> ORGANISM: Artificial Sequence
<220> FEATURE:
<223> OTHER INFORMATION: nucleotide sequence of the mutein shown in SEQ
      ID NO: 30

<400> SEQUENCE: 69

caggactcca cctcagacct gatcccagcc ccacctctga gcaaggtccc tctgcagcag     60

aacttccagg acaaccaatt ccaagggaaa tggtacgtgg tagggagggc cggaaatgat    120

gtgctgcgtg aggataagga cccggagaaa atggaggcga ccatttacga gttgaaagaa    180

gataaatcat ataacgtcac cgatgtgggg tttgtgcaga agagatacat gtacgtgact    240

catacctttg tgccggggag ccagccgggc gagtttactt taggcaacat tgaaagttat    300

ccgggcgtga catcagcttt ggtccgcgtc gtgagcaccg actacaacca gcatgccatg    360

gtgttcgtca agctggtgaa gcagaaccgc gagttgtttg agatcacact gtacgggcgc    420

acgaaagagc tgacaagcga gctgaaggaa aattttatcc gcttttccaa atctctgggc    480

ctccctgaaa accacatcgt cttccctgtc ccaatcgacc agatcgacgg c             531


<210> SEQ ID NO 70
<211> LENGTH: 534
<212> TYPE: DNA
<213> ORGANISM: Artificial Sequence
<220> FEATURE:
<223> OTHER INFORMATION: nucleotide sequence of the mutein shown in SEQ
```

ID NO: 31

<400> SEQUENCE: 70

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaacgtaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc agtttatcga cggc          534
```

<210> SEQ ID NO 71
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 32

<400> SEQUENCE: 71

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaaatgaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc agtatatcga cggc          534
```

<210> SEQ ID NO 72
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 33

<400> SEQUENCE: 72

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaactgaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc agtggatcga cggc          534
```

<210> SEQ ID NO 73
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 34

<400> SEQUENCE: 73

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaaatcaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc aggaaatcga cggc          534
```

<210> SEQ ID NO 74
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 35

<400> SEQUENCE: 74

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaagttaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc agtatatcga cggc          534
```

<210> SEQ ID NO 75
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 36

<400> SEQUENCE: 75

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaacgtaa ttaccatatt    240

gagacctttg tgccggggag ccagccgggc gagtttactt taggcacgat taaaagttat    300
```

ccgggcgaga cacctatttt ggtccgcgtc gtgagcacca actacaacca gcatgccatg 360
gtgttcttca agggggtgaa tcagaaccgc gagatttttg agatcgttct gtacgggcgc 420
acgaaagaac tgacaaacga actgaaggaa aattttatcc gcttttccaa atctctgggc 480
ctccctgaaa accacatcgt cttccctgtc ccaatcgacc agtggatcga cggc 534

<210> SEQ ID NO 76
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 37

<400> SEQUENCE: 76
caggactcca cctcagacct gatcccagcc ccacctctga gcaaggtccc tctgcagcag 60
aacttccagg acaaccaatt ccaagggaaa tggtacgttg tcgggtgggc cggaaatacg 120
ctgctgcgtg aggataagga tccgattaaa atgcaggcga tgatttacga gttgaaagaa 180
gataagtcat ataacgtcac ctgggtgtat tttgctgata agaaaaacaa ttaccatatt 240
gagacctttg tgccggggag ccagccgggc gagtttactt taggcacgat taaaagttat 300
ccgggcgaga cacctatttt ggtccgcgtc gtgagcacca actacaacca gcatgccatg 360
gtgttcttca agggggtgaa tcagaaccgc gagatttttg agatcgttct gtacgggcgc 420
acgaaagaac tgacaaacga actgaaggaa aattttatcc gcttttccaa atctctgggc 480
ctccctgaaa accacatcgt cttccctgtc ccaatcgacc agctgatcga cggc 534

<210> SEQ ID NO 77
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 38

<400> SEQUENCE: 77
caggactcca cctcagacct gatcccagcc ccacctctga gcaaggtccc tctgcagcag 60
aacttccagg acaaccaatt ccaagggaaa tggtacgttg tcgggtgggc cggaaatacg 120
ctgctgcgtg aggataagga tccgattaaa atgcaggcga tgatttacga gttgaaagaa 180
gataagtcat ataacgtcac ctgggtgtat tttgctgata agaaacgtaa ttaccatatt 240
gagacctttg tgccggggag ccagccgggc gagtttactt taggcacgat taaaagttat 300
ccgggcgaga cacctatttt ggtccgcgtc gtgagcacca actacaacca gcatgccatg 360
gtgttcttca agggggtgaa tcagaaccgc gagatttttg agatcgttct gtacgggcgc 420
acgaaagaac tgacaaacga actgaaggaa aattttatcc gcttttccaa atctctgggc 480
ctccctgaaa accacatcgt cttccctgtc ccaatcgacc aggttatcga cggc 534

<210> SEQ ID NO 78
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 39

<400> SEQUENCE: 78
caggactcca cctcagacct gatcccagcc ccacctctga gcaaggtccc tctgcagcag 60

```
aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaaaaaaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc aggatatcga cggc          534
```

<210> SEQ ID NO 79
<211> LENGTH: 534
<212> TYPE: DNA
<213> ORGANISM: Artificial Sequence
<220> FEATURE:
<223> OTHER INFORMATION: nucleotide sequence of the mutein shown in SEQ ID NO: 40

<400> SEQUENCE: 79

```
caggactcca cctcagacct gatcccagcc ccacctctga gcaaggtccc tctgcagcag     60

aacttccagg acaaccaatt ccaagggaaa tggtacgttg tcgggtgggc cggaaatacg    120

ctgctgcgtg aggataagga tccgattaaa atgcaggcga tgatttacga gttgaaagaa    180

gataagtcat ataacgtcac ctgggtgtat tttgctgata agaaattcaa ttaccatatt    240

gagacctttg tgccggggag ccagccgggc gagtttactt taggcacgat taaaagttat    300

ccgggcgaga cacctatttt ggtccgcgtc gtgagcacca actacaacca gcatgccatg    360

gtgttcttca agggggtgaa tcagaaccgc gagatttttg agatcgttct gtacgggcgc    420

acgaaagaac tgacaaacga actgaaggaa aattttatcc gcttttccaa atctctgggc    480

ctccctgaaa accacatcgt cttccctgtc ccaatcgacc aggatatcga cggc          534
```

<210> SEQ ID NO 80
<211> LENGTH: 37
<212> TYPE: PRT
<213> ORGANISM: human

<400> SEQUENCE: 80

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35
```

<210> SEQ ID NO 81
<211> LENGTH: 37
<212> TYPE: PRT
<213> ORGANISM: human

<400> SEQUENCE: 81

```
Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35
```

<210> SEQ ID NO 82
<211> LENGTH: 37
<212> TYPE: PRT
<213> ORGANISM: rat

<400> SEQUENCE: 82

```
Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
        35
```

<210> SEQ ID NO 83
<211> LENGTH: 37
<212> TYPE: PRT
<213> ORGANISM: rat

<400> SEQUENCE: 83

```
Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
        35
```

<210> SEQ ID NO 84
<211> LENGTH: 10
<212> TYPE: PRT
<213> ORGANISM: Artificial Sequence
<220> FEATURE:
<223> OTHER INFORMATION: C-terminal tag

<400> SEQUENCE: 84

```
Ser Ala Trp Ser His Pro Gln Phe Glu Lys
1               5                   10
```

<210> SEQ ID NO 85
<211> LENGTH: 8
<212> TYPE: PRT
<213> ORGANISM: Artificial Sequence
<220> FEATURE:
<223> OTHER INFORMATION: strep tag II

<400> SEQUENCE: 85

```
Trp Ser His Pro Gln Phe Glu Lys
1               5
```

<210> SEQ ID NO 86
<211> LENGTH: 18
<212> TYPE: PRT
<213> ORGANISM: Artificial Sequence
<220> FEATURE:
<223> OTHER INFORMATION: N-terminal tag

<400> SEQUENCE: 86

```
Met Arg Gly Ser His His His His His His Gly Ser Glu Asn Leu Tyr
1               5                   10                  15

Phe Gln
```

<210> SEQ ID NO 87
<211> LENGTH: 179

<212> TYPE: PRT
<213> ORGANISM: Artificial Sequence
<220> FEATURE:
<223> OTHER INFORMATION: lipocalin mutein

<400> SEQUENCE: 87

```
Gly Gln Asp Ser Thr Ser Asp Leu Ile Pro Ala Pro Pro Leu Ser Lys
1               5                   10                  15

Val Pro Leu Gln Gln Asn Phe Gln Asp Asn Gln Phe Gln Gly Lys Trp
            20                  25                  30

Tyr Val Val Gly Trp Ala Gly Asn Thr Leu Leu Arg Glu Asp Lys Asp
        35                  40                  45

Pro Ile Lys Met Gln Ala Met Ile Tyr Glu Leu Lys Glu Asp Lys Ser
    50                  55                  60

Tyr Asn Val Thr Trp Val Tyr Phe Ala Asp Lys Lys Ile Asn Tyr His
65                  70                  75                  80

Ile Glu Thr Phe Val Pro Gly Ser Gln Pro Gly Glu Phe Thr Leu Gly
                85                  90                  95

Thr Ile Lys Ser Tyr Pro Gly Glu Thr Pro Ile Leu Val Arg Val Val
            100                 105                 110

Ser Thr Asn Tyr Asn Gln His Ala Met Val Phe Phe Lys Gly Val Asn
        115                 120                 125

Gln Asn Arg Glu Ile Phe Glu Ile Val Leu Tyr Gly Arg Thr Lys Glu
    130                 135                 140

Leu Thr Asn Glu Leu Lys Glu Asn Phe Ile Arg Phe Ser Lys Ser Leu
145                 150                 155                 160

Gly Leu Pro Glu Asn His Ile Val Phe Pro Val Pro Ile Asp Gln Glu
                165                 170                 175

Ile Asp Gly
```

<210> SEQ ID NO 88
<211> LENGTH: 179
<212> TYPE: PRT
<213> ORGANISM: Artificial Sequence
<220> FEATURE:
<223> OTHER INFORMATION: lipocalin mutein

<400> SEQUENCE: 88

```
Gly Gln Asp Ser Thr Ser Asp Leu Ile Pro Ala Pro Pro Leu Ser Lys
1               5                   10                  15

Val Pro Leu Gln Gln Asn Phe Gln Asp Asn Gln Phe His Gly Lys Trp
            20                  25                  30

Tyr Val Val Gly Arg Ala Gly Asn Asp Val Leu Arg Glu Asp Lys Asp
        35                  40                  45

Pro Glu Lys Met Glu Ala Thr Ile Tyr Glu Leu Lys Glu Asp Lys Ser
    50                  55                  60

Tyr Asn Val Thr Asp Val Gly Phe Val Gln Lys Arg Cys Met Tyr Val
65                  70                  75                  80

Thr His Thr Phe Val Pro Gly Ser Gln Pro Gly Glu Phe Thr Leu Gly
                85                  90                  95

Asn Ile Glu Ser Tyr Pro Gly Val Thr Ser Ala Leu Val Arg Val Val
            100                 105                 110

Ser Thr Asp Tyr Asn Gln His Ala Met Val Phe Val Lys Leu Val Lys
        115                 120                 125

Gln Asn Arg Glu Leu Phe Glu Ile Thr Leu Tyr Gly Arg Thr Lys Glu
    130                 135                 140
```

```
Leu Thr Ser Glu Leu Lys Glu Asn Phe Ile Arg Phe Ser Lys Ser Leu
145                 150                 155                 160

Gly Leu Pro Glu Asn His Ile Val Phe Pro Val Pro Ile Asp Gln Cys
                165                 170                 175

Ile Asp Gly


<210> SEQ ID NO 89
<211> LENGTH: 179
<212> TYPE: PRT
<213> ORGANISM: Artificial Sequence
<220> FEATURE:
<223> OTHER INFORMATION: lipocalin mutein

<400> SEQUENCE: 89

Gly Gln Asp Ser Thr Ser Asp Leu Ile Pro Ala Pro Pro Leu Ser Lys
1               5                   10                  15

Val Pro Leu Gln Gln Asn Phe Gln Asp Asn Gln Phe His Gly Lys Trp
            20                  25                  30

Tyr Val Val Gly Arg Ala Gly Asn Asp Val Leu Arg Glu Asp Lys Asp
        35                  40                  45

Pro Glu Lys Met Glu Ala Thr Ile Tyr Glu Leu Lys Glu Asp Lys Ser
    50                  55                  60

Tyr Gln Val Thr Asp Val Gly Phe Val Gln Lys Arg Cys Met Tyr Val
65                  70                  75                  80

Thr His Thr Phe Val Pro Gly Ser Gln Pro Gly Glu Phe Thr Leu Gly
                85                  90                  95

Asn Ile Glu Ser Tyr Pro Gly Val Thr Ser Ala Leu Val Arg Val Val
            100                 105                 110

Ser Thr Asp Tyr Asn Gln His Ala Met Val Phe Val Lys Leu Val Lys
        115                 120                 125

Gln Asn Arg Glu Leu Phe Glu Ile Thr Leu Tyr Gly Arg Thr Lys Glu
    130                 135                 140

Leu Thr Ser Glu Leu Lys Glu Asn Phe Ile Arg Phe Ser Lys Ser Leu
145                 150                 155                 160

Gly Leu Pro Glu Asn His Ile Val Phe Pro Val Pro Ile Asp Gln Cys
                165                 170                 175

Ile Asp Asp


<210> SEQ ID NO 90
<211> LENGTH: 179
<212> TYPE: PRT
<213> ORGANISM: Artificial Sequence
<220> FEATURE:
<223> OTHER INFORMATION: lipocalin mutein

<400> SEQUENCE: 90

Gly Gln Asp Ser Thr Ser Asp Leu Lys Pro Ala Pro Pro Leu Ser Lys
1               5                   10                  15

Val Pro Leu Gln Gln Asn Phe Gln Asp Asn Gln Phe His Gly Lys Trp
            20                  25                  30

Tyr Val Val Gly Arg Ala Gly Asn Asp Val Leu Arg Glu Asp Lys Asp
        35                  40                  45

Pro Glu Lys Met Glu Ala Thr Ile Tyr Glu Leu Lys Glu Asp Lys Ser
    50                  55                  60

Tyr Asn Val Thr Asp Val Gly Phe Val Gln Lys Arg Cys Met Tyr Val
65                  70                  75                  80

Thr His Thr Phe Val Pro Gly Ser Gln Pro Gly Glu Phe Thr Leu Gly
```

```
                85                  90                  95

Asn Ile Glu Ser Tyr Pro Gly Val Thr Ser Ala Leu Val Arg Val Val
            100                 105                 110

Ser Thr Asp Tyr Asn Gln His Ala Met Val Phe Val Lys Leu Val Lys
        115                 120                 125

Gln Asn Arg Glu Leu Phe Glu Ile Thr Leu Tyr Gly Arg Thr Lys Glu
    130                 135                 140

Leu Thr Ser Glu Leu Lys Glu Asn Phe Ile Arg Phe Ser Lys Ser Leu
145                 150                 155                 160

Gly Leu Pro Glu Asn His Ile Val Phe Pro Val Pro Ile Asp Gln Cys
                165                 170                 175

Ile Asp Gly


<210> SEQ ID NO 91
<211> LENGTH: 179
<212> TYPE: PRT
<213> ORGANISM: Artificial Sequence
<220> FEATURE:
<223> OTHER INFORMATION: lipocalin mutein

<400> SEQUENCE: 91

Gly Gln Asp Ser Thr Ser Asp Leu Ile His Ala Pro Pro Leu Ser Lys
1               5                   10                  15

Val Pro Leu Gln Gln Asn Phe Gln Asp Asn Gln Phe His Gly Lys Trp
            20                  25                  30

Tyr Val Val Gly Arg Ala Gly Asn Asp Val Leu Arg Glu Asp Lys Asp
        35                  40                  45

Pro Glu Lys Met Glu Ala Thr Ile Tyr Glu Leu Lys Glu Asp Lys Ser
    50                  55                  60

Tyr Asn Val Thr Asp Val Gly Phe Val Gln Lys Arg Cys Met Tyr Val
65                  70                  75                  80

Thr His Thr Phe Val Pro Gly Ser Gln Pro Gly Glu Phe Thr Leu Gly
                85                  90                  95

Asn Ile Glu Ser Tyr Pro Gly Val Thr Ser Ala Leu Val Arg Val Val
            100                 105                 110

Ser Thr Asp Tyr Asn Gln His Ala Met Val Phe Val Lys Leu Val Lys
        115                 120                 125

Gln Asn Arg Glu Leu Phe Glu Ile Thr Leu Tyr Gly Arg Thr Lys Glu
    130                 135                 140

Leu Thr Ser Glu Leu Lys Glu Asn Phe Ile Arg Phe Ser Lys Ser Leu
145                 150                 155                 160

Gly Leu Pro Glu Asn His Ile Val Phe Pro Val Pro Ile Asp Gln Cys
                165                 170                 175

Ile Asp Gly


<210> SEQ ID NO 92
<211> LENGTH: 179
<212> TYPE: PRT
<213> ORGANISM: Artificial Sequence
<220> FEATURE:
<223> OTHER INFORMATION: lipocalin mutein

<400> SEQUENCE: 92

Gly Gln Asp Ser Thr Ser Asp Leu Lys Pro Ala Pro Pro Leu Ser Lys
1               5                   10                  15

Val Pro Leu Gln Gln Asn Phe Gln Asp Asn Gln Phe His Gly Lys Trp
            20                  25                  30
```

Tyr Val Val Gly Arg Ala Gly Asn Asp Val Leu Arg Glu Asp Lys Asp
35 40 45

Pro Glu Lys Met Glu Ala Thr Ile Tyr Glu Leu Lys Glu Asp Lys Ser
50 55 60

Tyr Gln Val Thr Asp Val Gly Phe Val Gln Lys Arg Cys Met Tyr Val
65 70 75 80

Thr His Thr Phe Val Pro Gly Ser Gln Pro Gly Glu Phe Thr Leu Gly
85 90 95

Asn Ile Glu Ser Tyr Pro Gly Val Thr Ser Ala Leu Val Arg Val Val
100 105 110

Ser Thr Asp Tyr Asn Gln His Ala Met Val Phe Val Lys Leu Val Lys
115 120 125

Gln Asn Arg Glu Leu Phe Glu Ile Thr Leu Tyr Gly Arg Thr Lys Glu
130 135 140

Leu Thr Ser Glu Leu Lys Glu Asn Phe Ile Arg Phe Ser Lys Ser Leu
145 150 155 160

Gly Leu Pro Glu Asn His Ile Val Phe Pro Val Pro Ile Asp Gln Cys
165 170 175

Ile Asp Asp

<210> SEQ ID NO 93
<211> LENGTH: 179
<212> TYPE: PRT
<213> ORGANISM: Artificial Sequence
<220> FEATURE:
<223> OTHER INFORMATION: lipocalin mutein

<400> SEQUENCE: 93

Gly Gln Asp Ser Thr Ser Asp Leu Ile His Ala Pro Pro Leu Ser Lys
1 5 10 15

Val Pro Leu Gln Gln Asn Phe Gln Asp Asn Gln Phe His Gly Lys Trp
20 25 30

Tyr Val Val Gly Arg Ala Gly Asn Asp Val Leu Arg Glu Asp Lys Asp
35 40 45

Pro Glu Lys Met Glu Ala Thr Ile Tyr Glu Leu Lys Glu Asp Lys Ser
50 55 60

Tyr Gln Val Thr Asp Val Gly Phe Val Gln Lys Arg Cys Met Tyr Val
65 70 75 80

Thr His Thr Phe Val Pro Gly Ser Gln Pro Gly Glu Phe Thr Leu Gly
85 90 95

Asn Ile Glu Ser Tyr Pro Gly Val Thr Ser Ala Leu Val Arg Val Val
100 105 110

Ser Thr Asp Tyr Asn Gln His Ala Met Val Phe Val Lys Leu Val Lys
115 120 125

Gln Asn Arg Glu Leu Phe Glu Ile Thr Leu Tyr Gly Arg Thr Lys Glu
130 135 140

Leu Thr Ser Glu Leu Lys Glu Asn Phe Ile Arg Phe Ser Lys Ser Leu
145 150 155 160

Gly Leu Pro Glu Asn His Ile Val Phe Pro Val Pro Ile Asp Gln Cys
165 170 175

Ile Asp Asp

<210> SEQ ID NO 94
<211> LENGTH: 537
<212> TYPE: DNA

```
<213> ORGANISM: Artificial Sequence
<220> FEATURE:
<223> OTHER INFORMATION: nucleotide sequence of the mutein shown in SEQ
      ID NO: 87

<400> SEQUENCE: 94

ggtcaggata gcaccagcga tctgattccg gcaccgcctc tgagcaaagt tccgctgcag     60

cagaattttc aggataatca gtttcagggc aaatggtatg ttgttggttg ggcaggtaat    120

accctgctgc gtgaagataa agatccgatt aaaatgcagg ccatgatcta tgaactgaaa    180

gaggataaaa gctacaacgt gacctgggtt tatttcgccg acaaaaaaat taactatcac    240

atcgaaacct ttgttccggg tagccagcct ggtgaattta ccctgggcac cattaaaagc    300

tatccgggtg aaaccccgat tctggttcgt gttgttagca ccaattataa ccagcatgcc    360

atggtgtttt tcaaaggcgt taatcagaac cgcgaaatct ttgaaattgt gctgtatggt    420

cgtaccaaag aactgaccaa tgagctgaaa gaaaacttta tccgctttag caaaagcctg    480

ggtctgccgg aaaatcatat tgtgtttccg gttccgattg atcaggaaat tgatggt       537


<210> SEQ ID NO 95
<211> LENGTH: 537
<212> TYPE: DNA
<213> ORGANISM: Artificial Sequence
<220> FEATURE:
<223> OTHER INFORMATION: nucleotide sequence of the mutein shown in SEQ
      ID NO: 88

<400> SEQUENCE: 95

ggtcaggata gcaccagcga tctgattccg gcaccgcctc tgagcaaagt tccgctgcag     60

cagaattttc aggataatca gtttcacggc aaatggtatg ttgttggtcg tgcaggtaat    120

gatgttctgc gtgaagataa agatccggaa aaaatggaag ccaccatcta tgaactgaaa    180

gaggataaaa gctacaacgt taccgatgtt ggttttgttc agaaacgttg catgtatgtg    240

acccatacct ttgttccggg tagccagcct ggtgaattta ccctgggtaa tattgaaagc    300

tatccgggtg ttaccagcgc actggttcgt gttgttagca ccgattataa ccagcatgca    360

atggtttttg tgaaactggt gaaacagaat cgcgaactgt ttgaaattac cctgtatggt    420

cgtaccaaag aactgaccag cgagctgaaa gaaaacttta ttcgttttag caaaagcctg    480

ggtctgccgg aaaatcatat tgtgtttccg gttccgattg atcagtgtat tgatggt       537


<210> SEQ ID NO 96
<211> LENGTH: 537
<212> TYPE: DNA
<213> ORGANISM: Artificial Sequence
<220> FEATURE:
<223> OTHER INFORMATION: nucleotide sequence of the mutein shown in SEQ
      ID NO: 89

<400> SEQUENCE: 96

ggtcaggata gcaccagcga tctgattccg gcaccgcctc tgagcaaagt tccgctgcag     60

cagaattttc aggataatca gtttcacggc aaatggtatg ttgttggtcg tgcaggtaat    120

gatgttctgc gtgaagataa agatccggaa aaaatggaag ccaccatcta tgaactgaaa    180

gaggataaaa gctaccaggt taccgatgtt ggttttgttc agaaacgttg catgtatgtg    240

acccatacct ttgttccggg tagccagcct ggtgaattta ccctgggtaa tattgaaagc    300

tatccgggtg ttaccagcgc actggttcgt gttgttagca ccgattataa ccagcatgca    360

atggtttttg tgaaactggt gaaacagaat cgcgaactgt ttgaaattac cctgtatggt    420
```

```
cgtaccaaag aactgaccag cgagctgaaa gaaaacttta ttcgttttag caaaagcctg    480

ggtctgccgg aaaatcatat tgtgtttccg gttccgattg atcagtgtat tgatgat       537


<210> SEQ ID NO 97
<211> LENGTH: 537
<212> TYPE: DNA
<213> ORGANISM: Artificial Sequence
<220> FEATURE:
<223> OTHER INFORMATION: nucleotide sequence of the mutein shown in SEQ
      ID NO: 90

<400> SEQUENCE: 97

ggtcaggata gcaccagcga tctgaaaccg gcaccgcctc tgagcaaagt tccgctgcag     60

cagaattttc aggataatca gtttcacggc aaatggtatg ttgttggtcg tgcaggtaat    120

gatgttctgc gtgaagataa agatccggaa aaaatggaag ccaccatcta tgaactgaaa    180

gaggataaaa gctacaacgt taccgatgtt ggttttgttc agaaacgttg catgtatgtg    240

acccatacct ttgttccggg tagccagcct ggtgaattta ccctgggtaa tattgaaagc    300

tatccgggtg ttaccagcgc actggttcgt gttgttagca ccgattataa ccagcatgca    360

atggtttttg tgaaactggt gaaacagaat cgcgaactgt ttgaaattac cctgtatggt    420

cgtaccaaag aactgaccag cgagctgaaa gaaaacttta ttcgttttag caaaagcctg    480

ggtctgccgg aaaatcatat tgtgtttccg gttccgattg atcagtgtat tgatggt       537


<210> SEQ ID NO 98
<211> LENGTH: 537
<212> TYPE: DNA
<213> ORGANISM: Artificial Sequence
<220> FEATURE:
<223> OTHER INFORMATION: nucleotide sequence of the mutein shown in SEQ
      ID NO: 91

<400> SEQUENCE: 98

ggtcaggata gcaccagcga tctgattcat gcaccgcctc tgagcaaagt tccgctgcag     60

cagaattttc aggataatca gtttcacggc aaatggtatg ttgttggtcg tgcaggtaat    120

gatgttctgc gtgaagataa agatccggaa aaaatggaag ccaccatcta tgaactgaaa    180

gaggataaaa gctacaacgt taccgatgtt ggttttgttc agaaacgttg catgtatgtg    240

acccatacct ttgttccggg tagccagcct ggtgaattta ccctgggtaa tattgaaagc    300

tatccgggtg ttaccagcgc actggttcgt gttgttagca ccgattataa ccagcatgca    360

atggtttttg tgaaactggt gaaacagaat cgcgaactgt ttgaaattac cctgtatggt    420

cgtaccaaag aactgaccag cgagctgaaa gaaaacttta ttcgttttag caaaagcctg    480

ggtctgccgg aaaatcatat tgtgtttccg gttccgattg atcagtgtat tgatggt       537


<210> SEQ ID NO 99
<211> LENGTH: 537
<212> TYPE: DNA
<213> ORGANISM: Artificial Sequence
<220> FEATURE:
<223> OTHER INFORMATION: nucleotide sequence of the mutein shown in SEQ
      ID NO: 92

<400> SEQUENCE: 99

ggtcaggata gcaccagcga tctgaaaccg gcaccgcctc tgagcaaagt tccgctgcag     60

cagaattttc aggataatca gtttcacggc aaatggtatg ttgttggtcg tgcaggtaat    120

gatgttctgc gtgaagataa agatccggaa aaaatggaag ccaccatcta tgaactgaaa    180
```

```
gaggataaaa gctaccaggt taccgatgtt ggttttgttc agaaacgttg catgtatgtg    240

acccatacct ttgttccggg tagccagcct ggtgaattta ccctgggtaa tattgaaagc    300

tatccgggtg ttaccagcgc actggttcgt gttgttagca ccgattataa ccagcatgca    360

atggtttttg tgaaactggt gaaacagaat cgcgaactgt ttgaaattac cctgtatggt    420

cgtaccaaag aactgaccag cgagctgaaa gaaaacttta ttcgttttag caaaagcctg    480

ggtctgccgg aaaatcatat tgtgtttccg gttccgattg atcagtgtat tgatgat       537
```

```
<210> SEQ ID NO 100
<211> LENGTH: 537
<212> TYPE: DNA
<213> ORGANISM: Artificial Sequence
<220> FEATURE:
<223> OTHER INFORMATION: nucleotide sequence of the mutein shown in SEQ
      ID NO: 93

<400> SEQUENCE: 100

ggtcaggata gcaccagcga tctgattcat gcaccgcctc tgagcaaagt tccgctgcag     60

cagaattttc aggataatca gtttcacggc aaatggtatg ttgttggtcg tgcaggtaat    120

gatgttctgc gtgaagataa agatccggaa aaaatggaag ccaccatcta tgaactgaaa    180

gaggataaaa gctaccaggt taccgatgtt ggttttgttc agaaacgttg catgtatgtg    240

acccatacct ttgttccggg tagccagcct ggtgaattta ccctgggtaa tattgaaagc    300

tatccgggtg ttaccagcgc actggttcgt gttgttagca ccgattataa ccagcatgca    360

atggtttttg tgaaactggt gaaacagaat cgcgaactgt ttgaaattac cctgtatggt    420

cgtaccaaag aactgaccag cgagctgaaa gaaaacttta ttcgttttag caaaagcctg    480

ggtctgccgg aaaatcatat tgtgtttccg gttccgattg atcagtgtat tgatgat       537
```

```
<210> SEQ ID NO 101
<211> LENGTH: 249
<212> TYPE: PRT
<213> ORGANISM: Artificial Sequence
<220> FEATURE:
<223> OTHER INFORMATION: TEV protease variant

<400> SEQUENCE: 101

Gly His His His His His His His Gly Glu Ser Leu Phe Lys Gly Pro
1               5                   10                  15

Arg Asp Tyr Asn Pro Ile Ser Ser Thr Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Asn Lys His Leu Phe Arg Arg Asn Asn Gly Thr Leu Leu
    50                  55                  60

Val Gln Ser Leu His Gly Val Phe Lys Val Lys Asn Thr Thr Thr Leu
65                  70                  75                  80

Gln Gln His Leu Ile Asp Gly Arg Asp Met Ile Ile Ile Arg Met Pro
                85                  90                  95

Lys Asp Phe Pro Pro Phe Pro Gln Lys Leu Lys Phe Arg Glu Pro Gln
            100                 105                 110

Arg Glu Glu Arg Ile Cys Leu Val Thr Thr Asn Phe Gln Thr Lys Ser
        115                 120                 125

Met Ser Ser Met Val Ser Asp Thr Ser Cys Thr Phe Pro Ser Ser Asp
    130                 135                 140

Gly Ile Phe Trp Lys His Trp Ile Gln Thr Lys Asp Gly Gln Cys Gly
```

-continued

```
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
            180                 185                 190

Asn Phe Met Glu Leu Leu Thr Asn Gln Glu Ala Gln Gln Trp Val Ser
        195                 200                 205

Gly Trp Arg Leu Asn Ala Asp Ser Val Leu Trp Gly Gly His Lys Val
    210                 215                 220

Phe Met Val Lys Pro Glu Glu Pro Phe Gln Pro Val Lys Glu Ala Thr
225                 230                 235                 240

Gln Leu Met Asn Arg Arg Arg Arg Arg
                245


<210> SEQ ID NO 102
<211> LENGTH: 747
<212> TYPE: DNA
<213> ORGANISM: Artificial Sequence
<220> FEATURE:
<223> OTHER INFORMATION: nucleotide sequence of the mutein shown in SEQ
      ID NO: 101

<400> SEQUENCE: 102

ggtcatcatc atcatcatca tcatggagaa agcttgttta aggggccgcg tgattacaac     60

ccgatatcga gcaccatttg tcatttgacg aatgaatctg atgggcacac aacatcgttg    120

tatggtattg gatttggtcc cttcatcatt acaaacaagc acttgtttag aagaaataat    180

ggaacactgt tggtccaatc actacatggt gtattcaagg tcaagaacac cacgactttg    240

caacaacacc tcattgatgg gagggacatg ataattattc gcatgcctaa ggatttccca    300

ccatttcctc aaaagctgaa atttagagag ccacaaaggg aagagcgcat atgtcttgtg    360

acaaccaact tccaaactaa gagcatgtct agcatggtgt cagacactag ttgcacattc    420

ccttcatctg atggcatatt ctggaagcat tggattcaaa ccaaggatgg gcagtgtggc    480

agtccattag tatcaactag agatgggttc attgttggta tacactcagc atcgaatttc    540

accaacacaa acaattattt cacaagcgtg ccgaaaaact tcatggaatt gttgacaaat    600

caggaggcgc agcagtgggt tagtggttgg cgattaaatg ctgactcagt attgtggggg    660

ggccataaag ttttcatggt gaaacctgaa gagccttttc agccagttaa ggaagcgact    720

caactcatga atcgtcgtcg ccgtcgc                                         747
```